(12) United States Patent
Aono et al.

(10) Patent No.: US 6,765,096 B1
(45) Date of Patent: Jul. 20, 2004

(54) TRICYCLIC COMPOUND HAVING ACYLOXYMETHOXYCARBONYL SIDE CHAIN

(75) Inventors: Katsutoshi Aono, Amagasaki (JP); Teruhisa Ichinashi, Osaka (JP); Akira Kugimiya, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 180 days.

(21) Appl. No.: 09/980,474

(22) PCT Filed: Jul. 14, 2000

(86) PCT No.: PCT/JP00/04724

§ 371 (c)(1),
(2), (4) Date: Dec. 3, 2001

(87) PCT Pub. No.: WO01/05768

PCT Pub. Date: Jan. 25, 2001

(30) Foreign Application Priority Data

Jul. 19, 1999 (JP) ........................................... 11/204977
Jul. 27, 1999 (JP) ........................................... 11/211702
Mar. 24, 2000 (JP) ........................................... 2000/84052

(51) Int. Cl.[7] ..................... C07D 213/63; C07D 211/18; A61K 31/4412; A61K 31/4427
(52) U.S. Cl. ...................... 546/290; 546/257; 546/261; 546/300; 514/345; 514/336
(58) Field of Search ............................ 546/300, 271.4, 546/272.1, 272.4, 272.7, 275.4, 276.1, 261, 257; 514/345, 336, 233.8, 235.8, 236.5, 238.8, 252.02, 252.06, 252.19

(56) References Cited

U.S. PATENT DOCUMENTS

| | | | |
|---|---|---|---|
| 4,728,670 A | 3/1988 | Haslanger et al. | 514/187 |
| 4,760,057 A | 7/1988 | Alexander | 514/187 |
| 4,916,230 A | 4/1990 | Alexander | 546/318 |

FOREIGN PATENT DOCUMENTS

| | | | |
|---|---|---|---|
| EP | 895981 A1 | 2/1997 | |
| EP | 1206935 | * 2/2001 | .......... A61K/31/09 |
| JP | 60-023359 A | 2/1985 | |
| JP | 61-018747 A | 1/1986 | |
| JP | 5-503925 A | 6/1993 | |
| WO | 91/10639 | 7/1991 | |
| WO | 94/14771 | 7/1994 | |
| WO | 96/18605 | 6/1996 | |

OTHER PUBLICATIONS

Michael Folkman, et al., Synthesis., Dec. 1990, pp. 1159–1166.

* cited by examiner

*Primary Examiner*—Rita Desai
*Assistant Examiner*—Janet Coppins
(74) *Attorney, Agent, or Firm*—Birch, Stewart, Kolasch & Birch, LLP

(57) ABSTRACT

There are provided a compound represented by the formula (I):

$$Y'-X'-\underset{W^3}{C}-V^2-\underset{W^2}{B}-V^1-\underset{W^1}{A}-X-Y \quad (I)$$

wherein X and X' are —N(COOCR$^3$R$^2$OCOR$^1$)—, —O— or the like, R$^1$ is alkyl substituted with carbamoyl, lower alkylcarbamoyl, carbamoyloxy, lower alkylcarbamoyloxy, acetylamino or the like, R$^2$ and R$^3$ are hydrogen or the like, Y and Y' are lower alkyl, lower alkenyl or the like, ring A, ring B and ring C are optionally substituted aromatic carbocycle or optionally substituted heterocycle, W$^1$, W$^2$ and/or W$^3$ are a bond or the like, and V$^1$ and V$^2$ are a single bond or the like, or a pharmaceutically acceptable salt or a solvate thereof, as well as a pharmaceutical composition containing the present compound.

13 Claims, 2 Drawing Sheets

TRICYCLIC COMPOUND HAVING ACYLOXYMETHOXYCARBONYL SIDE CHAIN

TECHNICAL FIELD

The present invention relates to a novel compound which is useful as a prodrug, a pharmaceutical composition containing the same and an intermediate therefor. More particularly, the present invention relates to a novel tricyclic compound having an acyloxymethoxycarbonyl side chain, an immunosuppressant and an antiallergic agent containing the same as well as a novel tricyclic compound having the immunosuppressive activity and the antiallergic activity and an intermediate therefor.

BACKGROUND ART

Making of prodrugs for pharmaceutical active substances is studied in many cases for the purpose of improving the physical properties such as the crystallizability, the stability, the water-solubility and the like, the bioavailability, and duration of the pharmacological activity. In particular, although it is desirable to convert amine compounds into a prodrug for the purpose of enhancing the absorbability and the stability, simple amidated prodrugs can not be returned to amines in the living body and it is said that procedures for converting into a prodrug require elaboration.

In WO97/39999 and WO98/04508, it is disclosed that para-terphenyl derivatives are effective as an immunosuppressant and an antiallergic agent. In particular, WO98/04508 refers to prodrugs and, more particularly, describes conversion of hydroxy compounds into a prodrug.

In JP-A23359/1985, JP-A18747/1986 and WO96/18605, described is a method of making a prodrug by substituting primary or secondary amines with —COOCR$^1$R$^2$OCOR$^3$ (R$^3$=alkyl, carboxyalkyl, haloalkyl, carbamylalkyl etc.). In addition, in JP-A503925/1993 and Synthesis (December, 1990, 1159–1166), there are described R$^2$SCOOCH$_2$OCOR$^1$ (Compound A) and ClCOOCH$_2$OCOR$^1$ (Compound B) as an intermediate for synthesizing a prodrug. However, it is not clearly described therein that Compound B can not be synthesized from Compound A (wherein R$^1$ is hydroxyethyl or acetylaminomethyl, and R$^2$ is ethyl) according to those methods.

Compounds having the similar skeleton to that of the present compound and having the immunosuppressive activity or the antiallergic activity are described in WO94/27980, WO95/13067, WO96/15123, WO95/15318, WO96/40659, WO96/40143, WO96/38412, WO96/10012, WO97/24356, WO97/27181, WO97/24324, WO97/44333, WO97/46524, WO98/04508, WO98/24766, WO98/24782, WO98/56785, FR2301250, U.S. Pat. No. 5,593,991, JP-B7368/1972, JP-A91259/1976, JP-A3163/1996, JP-A124571/1997, JP-A71564/1997, JP-A124571/1997, JP-A79993/1999, Bioorganic & Medicinal Chemistry Letters, Vol.5, No.18, p2143–2146(1995), J. Med. Chem., 1974, Vol.17, NO.11, 1177–1181 and the like.

Additionally, liquid crystalline compounds having the similar skeleton to that of the present compound are disclosed in JP-A121225/1983, JP-A87253/1997, JP-A253065/1988, JP-A106864/1986, JP-A106871/1986, JP-A83346/1990, JP-A48760/1997, JP-A31063/1997, WO88/07992 and the like, compounds having the insecticidal or miticidal activity in JP-A193067/1996, compounds having the circulatory disease and psychosis-treating activity in EP0600717A1, and compounds having the central nervous disease-treating activity in WO95/15954.

DISCLOSURE OF INVENTION

An object of the present invention is to provide a novel prodrug of a compound having the immunosuppressive activity and/or the antiallergic activity.

The present invention provides the following compounds or pharmaceutically acceptable salts thereof or prodrugs thereof.

[1] A compound represented by the formula (I):

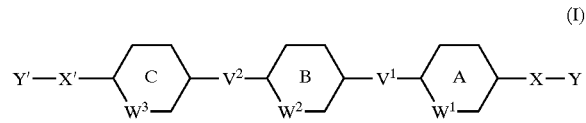

(hereinafter, referred to as compound (I))
wherein one of X and X' is —N(COOCR$^3$R$^2$OCOR$^1$)—, the other is —(CH$_2$)s- (wherein s is an integer of 0 to 2), —O—, —NR$^A$— (wherein R$^A$ is hydrogen, optionally substituted lower alkyl, lower alkenyl or lower alkylcarbonyl), —N(COOCR$^3$R$^2$OCOR$^1$)— or —S(O)p- (wherein p is an integer of 0 to 2), R$^1$ is lower alkyl substituted with 1 or 2 groups selected from the group consisting of —CONH$_2$, —CONHCH$_3$, —CONHC$_2$H$_5$, —OCONH$_2$, —OCONHCH$_3$, —OCONHC$_2$H$_5$, —(NHCOCRR')mNHCOCH$_3$, —(NHCOCRR')mNHCOC$_2$H$_5$, —CSNH$_2$, —(OCH$_2$CH$_2$)nOH, —OCH$_3$, —(OCH$_2$CH$_2$)nOCH$_3$, —COCH$_3$, —COC$_2$H$_5$, —OCOCH$_3$, —OCOC$_2$H$_5$, —NHOH, —NHCONH$_2$, —NHCSNH$_2$, —NHSO$_2$CH$_3$, —N(SO$_2$CH$_3$)$_2$, —O$_2$NH$_2$, —SOCH$_3$, —SO$_2$CH$_3$, —OCH$_2$CONH$_2$, —OCH$_2$CON(CH$_3$)$_2$, —SO$_2$N(CH$_3$)$_2$, —PO(OCH$_3$)$_2$, —NHCSNHC$_2$H$_5$, —CH=NNHCONH$_2$, —CH=NNHCSNH$_2$, —CH=NNHSO$_2$CH$_3$, triazolyl and tetrazolyl (wherein R and R' are each independently hydrogen or lower alkyl, m is an integer of 0 to 2, and n is an integer of 1 or 2), R$^2$ and R$^3$ are each independently hydrogen or lower alkyl, Y and Y' are each independently hydrogen, optionally substituted lower alkyl, optionally substituted lower alkenyl, optionally substituted lower alkynyl, optionally substituted cycloalkyl, optionally substituted cycloalkenyl, optionally substituted lower alkoxycarbonyl, optionally substituted sulfamoyl, optionally substituted amino, optionally substituted aryl or optionally substituted 5-membered or 6-membered heterocycle, when X is —CH$_2$—, Y may be optionally substituted lower alkoxy, when X' is —CH$_2$—, Y' may be optionally substituted lower alkoxy, when X is —O— or —NR$^A$—, Y may be optionally substituted lower alkylsulfonyl or optionally substituted arylsulfonyl, when X' is —O— or —NR$^A$—, Y' may be optionally substituted lower alkylsulfonyl or optionally substituted arylsulfonyl, ring A, ring B and ring C are each independently optionally substituted aromatic carbocycle or optionally substituted 5-membered or 6-membered heterocycle which may be fused with a benzene ring, when ring A, ring B and/or ring C are optionally substituted 5-membered-heterocycle, W$^1$, W$^2$ and/or W$^3$ represent a bond, one of V¹ and V² is a single bond, the other is a single bond, —O—, —NH—, —OCH₂—, —CH₂O—, —CH=CH—, —C≡C—, —CH(OR^B)— (wherein R^B is hydrogen or lower alkyl), —CO—, —NHCHR^C— or —CHR^CNH— (wherein R^C is hydrogen or hydroxy), when both V¹ and V² are a single bond, at least one of ring A, ring B and ring C is optionally substituted aromatic carbocycle, and at least one is optionally substituted 5-membered or 6-membered heterocycle which may be fused with a benzene ring,

[2] a compound represented by the formula (II):

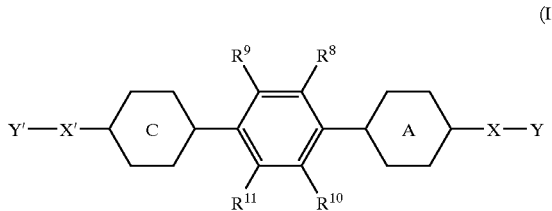

(II)

(hereinafter, referred to as compound (II))
wherein one of X and X' is —N(COOCR³R²OCOR¹)—, and the other is —O—, —NH— or —N(COOCR³R²OCOR¹)—, Y and Y' are each independently optionally substituted lower alkyl, optionally substituted lower alkenyl or optionally substituted lower alkynyl, R¹, R² and R³ have the same meanings as those for [1], ring A and ring C are each independently optionally substituted benzene ring or optionally substituted 6-membered heterocycle containing 1 or 2 heteroatoms, at least one of them being 6-membered heterocycle, R⁸, R⁹, R¹⁰ and R¹¹ are each independently hydrogen, halogen, hydroxy, optionally substituted lower alkyl, optionally substituted lower alkoxy, optionally substituted lower alkenyl, optionally substituted lower alkenyloxy, optionally substituted cycloalkyloxy, optionally substituted acyloxy, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsulfonyl or optionally substituted arylsulfonyloxy,

[3] a compound represented by the formula (III):

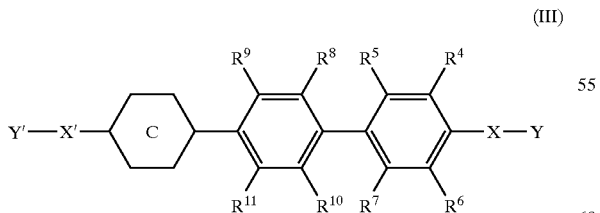

(III)

(hereinafter, referred to as compound (III))
wherein X is —NH— or —N(COOCR³R²OCOR¹)—, X' is —O—, —NH— or —N(COOCR³R²OCOR¹)—, at least one of X and X' being —N(COOCR³R²OCOR¹)—, Y and Y' are each independently optionally substituted lower alkyl or optionally substituted lower alkenyl, R¹, R² and R³ have the same meanings as those for [1], R⁴, R⁵, R⁶, R⁷, R⁸, R⁹, R¹⁰ and R¹¹ are each independently hydrogen, halogen, hydroxy, optionally substituted lower alkyl, optionally substituted lower alkoxy, optionally substituted lower alkenyl, optionally substituted lower alkenyloxy, carboxy, optionally substituted lower alkoxycarbonyl or optionally substituted amino, ring C is pyridine or pyrimidine, each being optionally substituted with lower alkyl,

[4] a compound described in any one of [1] to [3], wherein R¹ is C1 to C3 alkyl substituted with 1 or 2 groups selected from the group consisting of —CONH₂, —OCONH₂ and —(NHCOCRR')mNHCOCH₃,

[5] a compound described in [3], wherein R⁴ and R⁵ are each independently hydrogen or halogen,

[6] a compound described in [3], wherein R⁶ and R⁷ are both hydrogen,

[7] a compound described in [2] or [3], wherein R⁸ and R¹¹ are each independently hydrogen, hydroxy or lower alkyl,

[8] a compound described in [2] or [3], wherein R⁹ and R¹⁰ are each independently lower alkyl, lower alkoxy or lower alkoxycarbonyl,

[9] a compound described in any one of [1] to [3], wherein X' is —O—,

[10] a compound described in [3], wherein X is —NH— or —N(COOCR³R²OCOR¹)—, X' is —O—, —NH— or —N(COOCR³R²OCOR¹)—, at least one of X and X' being —N(COOCR³R²OCOR¹)—, R¹ is C1 to C3 alkyl substituted with 1 or 2 groups selected from the group consisting of —CONH₂, —OCONH₂ and —(NHCOCRR')mNHCOCH₃, R² and R³ are hydrogen or C1 to C3 alkyl, Y and Y' are each independently lower alkyl optionally substituted with halogen or lower alkenyl optionally substituted with halogen, R⁴ and R⁵ are each independently hydrogen or halogen, R⁶ and R⁷ are both hydrogen, R⁸ and R¹¹ are each independently hydrogen, hydroxy or lower alkyl, R⁹ and R¹⁰ are each independently lower alkyl, lower alkoxy or lower alkoxycarbonyl, and ring C is pyridine or pyrimidine, each being optionally substituted with lower alkyl,

[11] a compound described in any one of [1], [2], [3] and [10], wherein Y and Y' are both prenyl,

[12] a compound described in [3] or [4], wherein ring C is

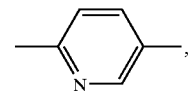

R⁴ and R⁵ are each independently hydrogen, halogen or lower alkoxy, R⁶ and R⁷ are each independently hydrogen, halogen or lower alkyl, R⁸ and R¹¹ are both lower alkyl, or one of them is lower alkyl and the other is hydrogen or lower alkoxy, R⁹ and R¹⁰ are both hydrogen, lower alkyl or lower alkoxy, and one of —X—Y and —X'—Y' is —N(COOCR³R²OCOR¹)-(optionally substituted lower alkyl or optionally substituted lower alkenyl), and the other is prenyloxy or prenylamino,

[13] a compound described in [3] or [4], wherein ring C is

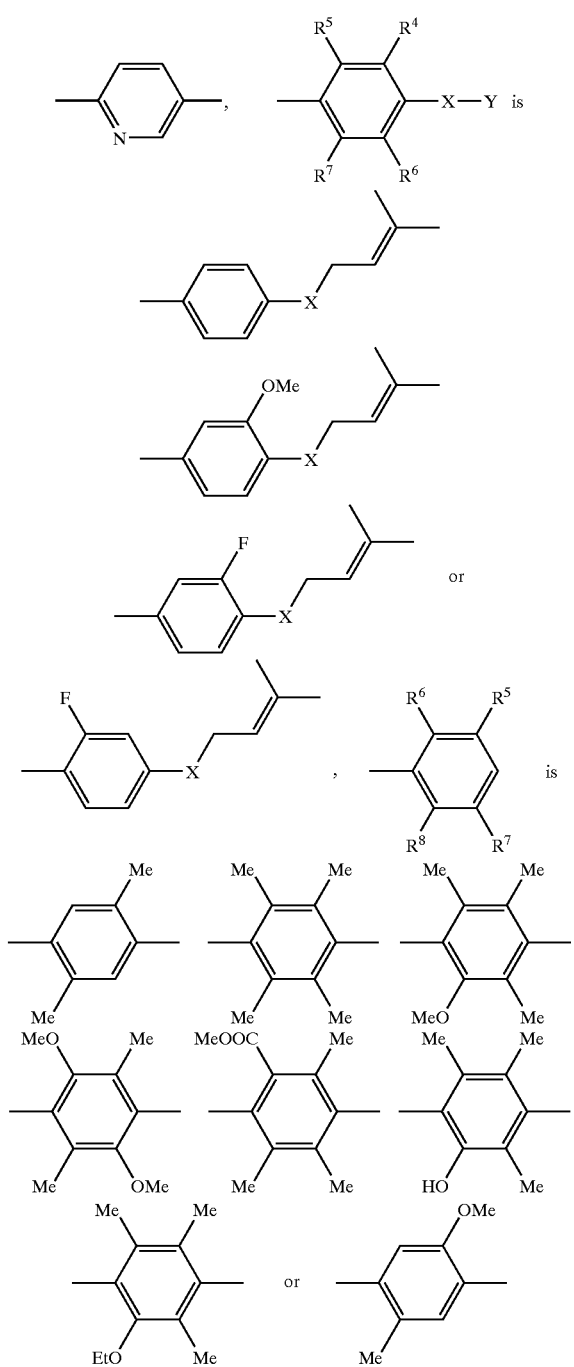

wherein X has the same meaning as that for [3], a salt or solvate thereof.

Another embodiment of the present invention provides a pharmaceutical composition containing a compound described in any one of [1] to [13] or a pharmaceutically acceptable salt or solvate thereof, more particularly, an immunosuppressive agent or an antiallergic agent. Furthermore, the present invention provides a method for inhibiting an immunoreaction, or a method for treating or preventing allergic diseases, which comprises administering a compound (I). Further, the present invention provides use of a compound for preparing a medicament for inhibiting an immunoreaction, or treating or preventing allergic diseases.

Another embodiment of the present invention provides the following compounds useful as an intermediate for compounds (I) and (II):

a compound represented by the formula (VIIb'):

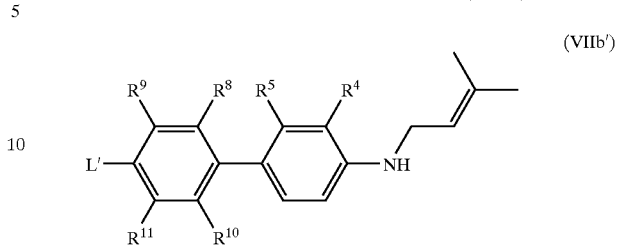

wherein one of $R^4$ and $R^5$ is hydrogen, the other is halogen, $R^8$ and $R^{11}$ are each independently hydrogen, hydroxy or lower alkyl, $R^9$ and $R^{10}$ are each independently lower alkyl, lower alkoxy or lower alkoxycarbonyl, L' is dihydroxyboryl, di-lower alkylboryl or di-lower alkoxyboryl, a pharmaceutically acceptable salt or solvate thereof, and a compound represented by the formula (VIb'):

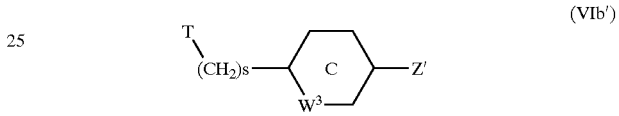

wherein ring C is pyridine ring optionally substituted with lower alkyl or pyrimidine ring optionally substituted with lower alkyl, T is protected hydroxy, lower alkylthio or arylthio, Z' is dihydroxyboryl, di-lower alkylboryl or di-lower alkoxyboryl, and s is an integer of 0 to 2, or pharmaceutically acceptable salt or solvate thereof.

BEST MODE FOR CARRYING OUT THE INVENTION

Figure 1:
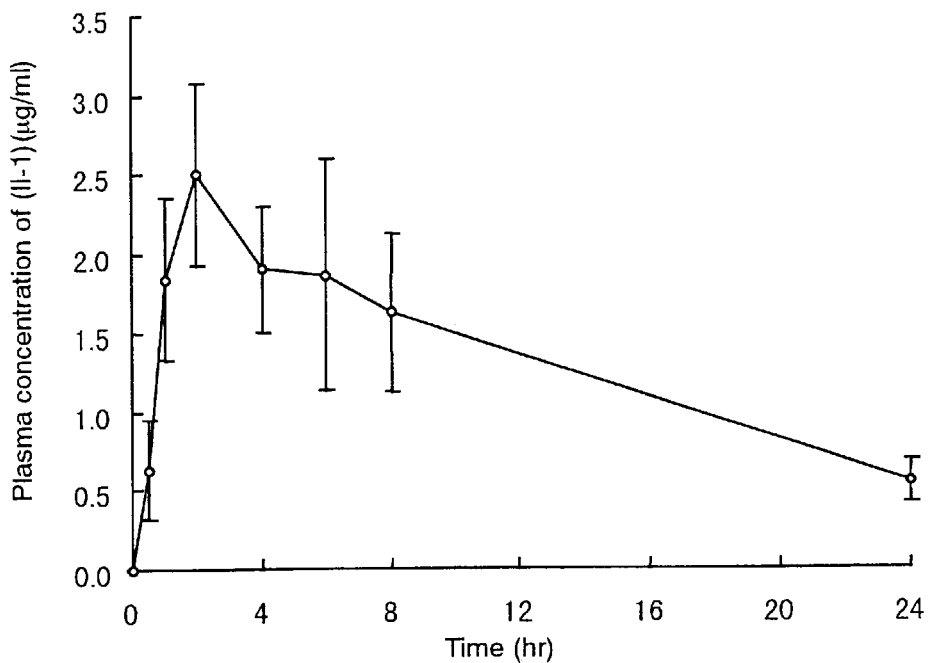
FIG. 1 is a view showing the concentration of a parent compound (II-1) in plasma when compound (I-1) is administered.

As used herein, the "halogen" includes fluorine, chlorine, bromine and iodine. In particular, fluorine and chlorine are preferable.

The "lower alkyl" includes a straight or branched C1 to C10, preferably C1 to C8, more preferably C1 to C5, and most preferably C1 to C3 alkyl. Examples thereof include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl. Most preferable is methyl.

The "C1 to C5 alkyl" includes a straight or branched alkyl, for example, methyl, ethyl, n-propyl, isopropyl, n-butyl, isobutyl, sec-butyl, tert-butyl, n-pentyl, isopentyl and neopentyl.

The "C1 to C3 alkyl" includes a straight or branched alkyl, for example, methyl, ethyl, n-propyl and isopropyl.

Examples of a substituent of the "optionally substituted lower alkyl" include halogen; hydroxy; lower alkoxy optionally substituted with lower alkoxy; acyl; acyloxy; carboxy; lower alkoxycarbonyl; mercapto; lower alkylthio; amino optionally substituted with hydroxy, lower alkyl or optionally substituted acyl, imino optionally substituted with hydroxy, lower alkoxy, carboxy-lower alkoxy, aryl-lower alkoxy or 5-membered or 6-membered heterocycle; hydrazono optionally substituted with carbamoyl or lower alkoxycarbonyl; carbamoyl optionally substituted with lower alkyl or amino; thiocarbamoyl optionally substituted with lower alkyl; cycloalkyl optionally substituted with lower alkyl or lower alkoxy; cycloalkenyl optionally substituted with lower alkyl; cyano; phenyl optionally substituted with 1 or more of hydroxy, lower alkyl, carboxy, lower alkoxycarbonyl and lower alkoxy; 5-membered or 6-membered heterocycle optionally substituted with lower alkyl and optionally fused with a benzene ring. In this case, any position may be substituted with 1 or more of these substituents. Preferable is a non-substituted lower alkyl.

A lower alkyl part of the "lower alkoxy" is the same as that for the above "lower alkyl".

Examples of a substituent of the "optionally substituted lower alkoxy" include halogen; hydroxy; lower alkoxy optionally substituted with acyloxy; acyl; acyloxy; carboxy; lower alkoxycarbonyl; lower alkylthio; amino optionally substituted with lower alkyl; phenyl optionally substituted with lower alkyl or lower alkoxy; heterocycle; heterocyclic carbonyloxy. Preferable is a non-substituted lower alkoxy.

A lower alkyl part for the "lower alkylthio", "lower alkoxycarbonyl", "lower alkylsulfonyl", "lower alkylsulfonyloxy", "lower alkylsulfinyl", "lower alkylcarbamoyl", "lower alkylcarbamoyloxy" and "lower alkylenedioxy" is the same as that for the above "lower alkyl".

A substituent for the "optionally substituted lower alkoxycarbonyl", "optionally substituted lower alkylsulfonyl", "optionally substituted lower alkylsulfonyloxy", "optionally substituted lower alkylsulfinyl" and "optionally substituted lower alkylthio" is the same as that for the above "optionally substituted lower alkoxy".

The "lower alkenyl" includes a straight or branched C2 to C10, preferably C2 to C8, more preferably C3 to C6 alkenyl having 1 or more double bonds at an arbitrary position. More particularly, examples thereof include vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl and decenyl. A substituent for the "optionally substituted lower alkenyl", is the same as that for the above "optionally substituted lower alkoxy".

A lower alkenyl part of the "lower alkenyloxy", "lower alkenyloxycarbonyl" and "lower alkenylthio" is the same as that for the above "lower alkenyl". A substituent of the "optionally substituted lower alkenyloxy", "optionally substituted lower alkenyloxycarbonyl" and "optionally substituted lower alkenylthio" is as same as that for the above "optionally substituted lower alkoxy".

The "lower alkynyl" includes a straight or branched C2 to C10, preferably C2 to C8, and more preferably C3 to C6 alkynyl, for example, ethynyl, propynyl (2-propynyl etc.), butynyl (2-butynyl etc.), pentynyl, hexynyl, heptynyl, octynyl, nonynyl and decynyl. These have 1 or more triple bonds at an arbitrary position and, further, may have a double bond.

A substituent of the "optionally substituted lower alkynyl" is the same as that for the above "optionally substituted lower alkoxy".

The "acyl" includes a straight or branched C1 to C10, more preferably C1 to C6, most preferably C1 to C4 alkylcarbonyl, a straight or branched C3 to C10, more preferably C3 to C6, most preferably C3 to C4 alkenylcarbonyl, and C4 to C9, preferably C4 to C7 cycloalkylcarbonyl and arylcarbonyl. More particularly, examples thereof include formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl and benzoyl. In particular, acetyl is preferable.

A substituent of the "optionally substituted acyl" is the same as that for the above "optionally substituted lower alkoxy", and cycloalkylcarbonyl and arylcarbonyl may further have lower alkyl as a substituent.

An acyl part of the "acyloxy" is the same as that for the above "acyl", and a substituent of the "optionally substituted acyloxy" is the same as that for the above "optionally substituted acyl".

The "cycloalkyl" is a C3 to C6 carbocycle and includes, for example, cyclopropyl, cyclobutyl, cyclopentyl, cyclohexyl and the like.

Examples of a substituent of the "optionally substituted cycloalkyl" include lower alkyl, halogen, hydroxy, carboxy, lower alkoxycarbonyl, lower alkoxy, lower alkylenedioxy, imino optionally substituted with lower alkoxy, aryl and 5-membered or 6-membered heterocycle. 1 or more arbitrary positions may be substituted.

The "cycloalkenyl" includes the above cycloalkyl having 1 or more double bonds at an arbitrary position in the ring, for example, cyclopropenyl, cyclobutenyl, cyclopentenyl, cyclohexenyl and cyclohexadienyl.

A substituent of the "optionally substituted cycloalkenyl" is the same as that for the above "cycloalkyl".

Examples of a substituent of the "optionally substituted amino" include optionally substituted lower alkyl {wherein the substituent is lower alkoxy, cycloalkyl, optionally substituted amino (the substituent is lower alkyl, phenyl etc.), optionally substituted aryl (the substituent is lower alkyl, lower alkoxy, carboxy, lower alkoxycarbonyl) or heterocycle}; lower alkylidene; lower alkenyl; lower alkynyl; cycloalkyl; aryl optionally substituted with lower alkyl, carboxy, acyl or lower alkoxycarbonyl; sulfamoyl optionally substituted with lower alkyl; lower alkoxycarbonyl; lower alkylsulfonyl; amino optionally substituted with lower alkyl or lower alkylidene and the like.

The "optionally substituted imino" includes substituted imino and non-substituted imino, and a substituent therefor is the same as that for the above "optionally substituted amino".

The "optionally substituted carbamoyl" includes carbamoyl optionally substituted with lower alkyl, lower alkenyl, lower alkynyl or the like.

The "optionally substituted sulfamoyl" includes sulfamoyl optionally substituted with lower alkyl, lower alkenyl, lower alkynyl or the like.

The "aromatic carbocycle" includes benzene ring, naphthalene ring, anthracene ring and phenanthrene ring. In particular, benzene ring is preferable.

In addition, the "aromatic carbocycle" may be fused with another carbocycle, and examples thereof include indane ring, indene ring and dihydronaphthalene ring.

The "aryl" includes phenyl, naphthyl, anthryl and phenanthryl. In particular, phenyl is preferable. In addition, the "aryl" may be fused with another carbocycle, wherein a bonding radical(s) may be located at any positions. Examples thereof include indanyl, indenyl, dihydronaphthyl and the like.

Examples of a substituent for the "optionally substituted aromatic carbocycle" and "optionally substituted aryl" include halogen; hydroxy; lower alkyl optionally substituted with halogen or carboxy; lower alkoxy optionally substituted with halogen, aryl, heteroaryl or lower alkoxy; lower alkenyl; lower alkynyl; cycloalkyl; lower alkenyloxy; lower alkynyloxy; cycloalkoxy; acyl; acyloxy; carboxy; lower alkoxycarbonyl; lower alkenyloxycarbonyl; lower alkylthio; lower alkynylthio; amino optionally substituted with lower alkyl, cycloalkyl-lower alkyl, heteroaryl-lower alkyl, lower alkenyl, cycloalkyl, acyl optionally substituted with halogen, lower alkoxycarbonyl, or lower alkylsulfonyl; guanidino; nitro; lower alkylsulfonyl; dihydroxyboryl; lower alkylsulfonyloxy optionally substituted with halogen; arylsulfonyl; arylsulfonyloxy; aryl; and 5-membered or 6-membered heterocycle. 1 or more arbitrary positions may be substituted with these substituents. Preferable are halogen; hydroxy; lower alkyl optionally substituted with halogen; lower alkoxy optionally substituted with aryl or lower alkoxy; lower alkenyloxy; acyloxy; lower alkylthio; amino optionally substituted with lower alkyl, lower alkenyl, acyl optionally substituted with halogen, or lower alkylsulfonyl; nitro; lower alkylsulfonyl; lower alkylsulfonyloxy optionally substituted with halogen; and arylsulfonyloxy.

An aryl part for the "arylsulfonyl" and "arylsulfonyloxy" is the same as that for the above "aryl". In particular, phenyl is preferable. A substituent of the "optionally substituted arylsulfonyl" is the same as that for the above "optionally substituted aryl". In particular, non-substituted is preferable.

The "5-membered or 6-membered heterocycle" includes 5-membered or 6-membered heterocycles containing 1 or more heteroatoms selected from O, S and N in the ring, for example, aromatic heterocycles such as pyrrole ring, imidazole ring, pyrazole ring, pyridine ring, pyridazine ring, pyrimidine ring, pyrazine ring, triazole ring, triazine ring, isoxazole ring, oxazole ring, oxadiazole ring, isothiazole ring, thiazole ring, thiadiazole ring, furan ring and thiophene ring, and non-aromatic heterocycles such as tetrahydropyrane ring, dihydropyridine ring, dihydropyridazine ring, dihydropyrazine ring, dioxane ring, oxathiolane ring, thiane ring, pyrrolidine ring, pyrroline ring, imidazolidine ring, imidazolidine ring, pyrazolidine ring, pyrazoline ring, piperidine ring, piperazine ring and morpholine ring.

The "5-membered or 6-membered heterocycle containing 1 or 2 heteroatoms" includes aromatic heterocycles such as pyrrole ring, imidazole ring, pyrazole ring, pyridine ring, pyridazine ring, pyrimidine ring, pyrazine ring, isoxazole ring, oxazole ring, isothiazole ring, thiazole ring, furan ring and thiophene ring, and non-aromatic heterocycles such as dioxane ring, oxathiolane ring, thiane ring, dihydropyridine ring, pyrrolidine ring, pyrroline ring, imidazolidine ring, imidazoline ring, pyrazolidine ring, pyrazoline ring, piperidine ring, piperazine ring and morpholine ring, among the above "5-membered or 6-membered heterocycle". In particular, aromatic heterocycles are preferable.

Examples of the "5-membered or 6-membered heterocycle" in ring A, ring B or ring C include preferably 2,5-pyridinediyl and 2,5-pyrimidinediyl.

Examples of the "5-membered or 6-membered heterocycle" in Y include preferably 4-pyridyl, 2-furyl, 3-furyl, 2-thienyl, 3-thienyl, 1,2-dihydropyridyl, 2,3-dihydropyridazinyl, 1,2-dihydropyrazinyl and the like.

Examples of the "5-membered or 6-membered heterocycle which may be fused with a benzene ring" include heterocycles exemplified for the above "5-membered or 6-membered heterocycle", as well as indole ring, isoindole ring, benzimidazole ring, indazole ring, cinnoline ring, phthalazine ring, quinazoline ring, benzisoxazole ring, benzoxazole ring, benzoxadiazole ring, benzothiazole ring, benzisothiazole ring, benzofuran ring, benzothiophene ring, benzotriazole ring, isobenzofuran ring, indoline ring, isoindoline ring and chromene ring.

Examples of a substituent for the "optionally substituted 5-membered or 6-memberdsheterocycle" and "optionally substituted 5-membered or 6-membered heterocycle which may be fused with a benzene ring" include halogen; hydroxy; lower alkyl optionally substituted with hydroxy or acyloxy; lower alkoxy optionally substituted with halogen, aryl or 5-membered or 6-membered heterocycle; lower alkenyl; lower alkenyloxy; lower alkynyl; lower alkynyloxy; acyloxy; carboxy; lower alkoxycarbonyl; mercapto; lower alkylthio; lower alkenylthio; amino optionally mono- or di-substituted with halogen, optionally substituted lower alkyl (the substituent is cycloalkyl or 5-membered or 6-membered heterocycle), acyl optionally substituted with halogen, lower alkenyl, cycloalkyl or lower alkylsulfonyl; imino optionally substituted with lower alkylsulfonyl; nitro; lower alkylsulfonyl; aryl; 5-membered or 6-membered heterocycle; oxo; and oxide. 1 or more arbitrary positions may be substituted.

A substituent for the "optionally substitute 5-membered. or 6-membered heterocycle containing 1 or 2 heteroatoms" is the same as that described above. In particular, heterocycle substituted with lower alkyl or non-substituted heterocycle is preferable.

"When ring A, ring B and/or ring C is (are) optionally substituted 5-membered heterocycle, $W^1$, $W^2$ and/or $W^3$ represents (or represent) a bond" means that when ring A is 5-membered heterocycle, $W^1$ represents a bond, and positions of $V^1$ and X binding to ring A are as follows:

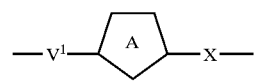

Similarly, when ring B or ring C is 5-membered heterocycle, $W^2$ or $W^3$ represents a bond, respectively and positions of $V^1$, $V^2$ and X' for binding are as follows:

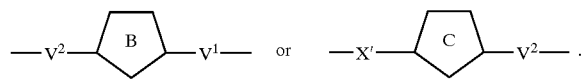

X, X', $V^1$ or $V^2$ may be connected to a heteroatom which is a constituent atom for ring A, ring B or ring C, respectively.

Examples of a pharmaceutically acceptable salt for a compound (I), a compound (II) and a compound (III) (hereinafter, referred to as present compound) in the present specification include salts of a mineral acid such as hydrochloric acid, sulfuric acid, nitric acid, phosphoric acid, hydrofluoric acid and hydrobromic acid; salts of an organic acid such as formic acid, acetic acid, tartaric acid, lactic acid, citric acid, fumaric acid, maleic acid and succinic acid; salts of an organic base such as ammonium, trimethylammonium and triethylammonium; salts of an alkali metal such as sodium, potassium and the like and salts of an alkaline earth metal such as calcium, magnesium and the like.

The present invention includes a solvate of the present compound. One molecule of the compound may be coordinated with an arbitrary number of suitable organic solvents or water molecules. Preferably, the solvate is a hydrate. In addition, the present invention includes all stereoisomers (such as atrop isomer) of the present compound.

The present compound has the great characteristic that it is converted into a prodrug by substituting an amino group of an amino-substituted tricyclic compound with an acyloxymethoxycarbonyl group substituted with a nonionic and hydrophilic group. The "nonionic and hydrophilic group" includes a group which is not dissociated into ions in a solution and can reduce the lipophilicity (hydrophobicity) of a parent compound to impart the hydrophilicity thereto. The hydrophilic group includes a group having a negative hydrophobic substituent constant n obtained by a method described in Journal of Medicinal Chemistry, 1973, vol. 16, No.11, 1207–1216 and Journal of Medicinal Chemistry, 1977, vol.20, No. 20, 304–306, preferably a group having $\pi$ of −0.5 or less. The hydrophobic substituent constant can be obtained by the following equation:

$$\pi = \log P_{X\text{-}C6H5} - \log P_{benzene}$$

wherein $P_{X\text{-}C6H5}$ is a distribution coefficient of benzene substituted with a substituent X for which $\pi$ is desired to be obtained, between water-octanol, and $P_{benzene}$ is a distribution coefficient of benzene between water-octanol ($\log P_{benzen}$=2.13).

Examples thereof include —$CONH_2$, —$CONHCH_3$, —$CONHC_2H_5$, —$OCONH_2$, —$OCONHCH_3$, —$OCONHC_2H_5$, —$(NHCOCRR')mNHCOCH_3$, —$(NHCOCRR')mNHCOC_2H_5$, —$CSNH_2$, —$(OCH_2CH_2)nOH$, —$OCH_3$, —$(OCH_2CH_2)nOCH_3$, —$COCH_3$, —$COC_2H_5$, —$OCOCH_3$, —$OCOC_2H_5$, —$NHOH$, —$NHCONH_2$, —$NHCSNH_2$, —$NHSO_2CH_3$, —$N(SO_2CH_3)_2$, —$SO_2NH_2$, —$SOCH_3$, —$SO_2CH_3$, —$OCH_2CONH_2$, —$OCH_2CON(CH_3)_2$, —$SO_2N(CH_3)_2$, —$PO(OCH_3)_2$, —$NHCSNHC_2H_5$, —$CH=NNHCONH_2$, —$CH=NNHCSNH_2$, —$CH=NNHSO_2CH_3$, triazolyl and tetrazolyl (R and R' are each independently hydrogen or lower alkyl, m is an integer of 0 to 2, and n is an integer of 1 or 2).

When an amino group of an amino-substituted tricyclic compound is substituted with a group outside a scope of the present invention, the sufficient effects as a prodrug can not be obtained.

For example, when the amino group is simply substituted with acyl or alkoxycarbonyl, the resulting compound is stable and is not returned to an active form in the living body. When the amino group is substituted with aminoacyl or carboxyacyl, the resulting compound has the reduced lipophilicity but is not returned to an active form in the living body.

In addition, when the amino group is substituted with non-substituted acyloxyalkoxycarbonyl, the resulting compound has the high lipophilicity and is difficult to be absorbed into the living body.

When the amino group is substituted with hydroxy-substituted acyloxymethoxycarbonyl, the resulting compound has a low melting point and is difficult to be formulated into preparations.

A compound wherein the amino group is substituted with acyloxymethoxycarbonyl substituted with an ionic hydrophilic group such as carboxy and dialkylamino can obtain improved effects such as the hydrophilicity but is hardly returned to an active form in the living body. In addition, every such the compound has problems that it has the low yield, is not crystallized, and is inferior in the chemical stability leading to difficulty in formulation into preparations and, thus, the compound can not be put into practice industrially.

A compound wherein the amino group is substituted with acyloxymethoxycarbonyl substituted with an ionic hydrophilic group such as phosphate group and sulfonate group is difficult to be synthesized, there remains a problem for industrial utilization.

Consequently, the present invention is characterized in a combination of an amino-substituted terphenyl compound and an acyloxymethoxycarbonyl group substituted with the aforementioned groups.

Every compound (I) is a prodrug for a compound having the immunosuppressive and/or antiallergic activity and, inter alia, the following compounds are particularly preferable.

1) a compound wherein one of X and X' is —$N(COOCR^3R^2OCOR^1)$— and the other is —O—, —NH— or —$N(COOCR^3R^2OCOR^1)$—, and $R^1$, $R^2$ and $R^3$ have the same meanings as those for [1] (hereinafter, X and X' are referred to as X1), a compound wherein X is —NH— or —$N(COOR^3R^2OCOR^1)$—, X' is —O— or —$N(COOR^3R^2OCOR^1)$—, at least one of them is —$N(COOR^3R^2OCOR^1)$—, and $R^1$, $R^2$ and $R^3$ have the same meanings as those for [1] (hereinafter, X and X' are referred to as X2), a compound wherein X is —$N(COOR^3R^2OCOR^1)$—, X' is —O— or —$N(COOR^3R^2OCOR^1)$—, $R^1$ is lower alkyl substituted with 1 or 2 groups selected from the group consisting of —$CONH_2$, —$CONHCH_3$, —$CONHC_2H_5$, —$OCONH_2$, —$OCONHCH_3$, —$OCONHC_2H_5$, —$NHCOCH_3$, —$NHCOCH_2NHCOCH_3$, —$(NHCOCH_2)_2NHCOCH_3$ and —$NHCOCH(Me)NHCOCH_3$, and $R^2$ and $R^3$ are each independently hydrogen or lower alkyl (hereinafter, X and X' are referred to as X3), a compound wherein X is —$N(COOR^3R^2OCOR^1)$—, X' is —O—, $R^1$ is lower alkyl substituted with 1 or 2 groups selected from the group consisting of —$CONH_2$, —$OCONH_2$, —$NHCOCH_3$ and —$NHCOCH_2NHCOCH_3$, and $R^2$ and $R^3$ are both hydrogen (hereinafter, X and R' are referred to as X4), a compound wherein X is —$N(COOCR^3R^2OCOR^1)$—, X' is —O—, $R^1$ is (i) C1 to C3 alkyl substituted with —$CONH_2$ and/or —$NHCOCH_3$, or (ii) C1 to C3 alkyl substituted with $NHCOCH_2NHCOCH_3$, and $R^2$ and $R^3$ are both hydrogen (hereinafter, X and X' are referred to as X5), 2) a compound wherein Y and Y' are each independently optionally substituted lower alkyl, optionally substituted lower alkenyl or optionally substituted lower alkynyl (hereinafter, Y and Y' are referred to as Y1), a compound wherein Y and Y' are each independently optionally substituted lower alkyl, optionally substituted lower alkenyl or optionally substituted lower alkynyl(wherein the substituent is halogen; hydroxy; lower alkoxy; acyl; acyloxy; carboxy; lower alkoxycarbonyl; lower alkylthio; amino optionally substituted with hydroxy, lower alkyl or acyl; carbamoyl optionally substituted with lower alkyl or amino; cycloalkyl optionally substituted with lower alkyl or lower alkoxy; cycloalkenyl optionally substituted with lower alkyl; cyano; phenyl optionally substituted with 1 or more of hydroxy, lower alkyl, carboxy, lower alkoxycarbonyl or lower alkoxy; 5-membered or 6-membered heterocycle optionally substituted with lower alkyl)(hereinafter, Y and Y' are referred to as Y2), a compound wherein Y and Y' are each independently optionally substituted lower alkyl or optionally substituted lower alkenyl (wherein the substituent is halogen; hydroxy; lower alkoxy; acyl; carboxy; lower alkoxycarbonyl; amino optionally substituted with lower alkyl; carbamoyl optionally substituted with lower alkyl; cycloalkyl; phenyl; 5-membered or 6-membered heterocycle)(hereinafter, Y and Y' are referred to as Y3), a compound wherein Y and Y' are each independently lower alkyl or lower alkenyl (hereinafter, Y and Y' are referred to as Y4), a compound wherein Y and Y' are each independently lower alkenyl (hereinafter, Y and Y' are referred to as Y5), 3) a compound wherein ring A is optionally substituted benzene ring or optionally substituted 6-membered heterocycle (hereinafter, ring A is referred to as A1), a compound wherein ring A is optionally substituted benzene ring or 6-membered heterocycle containing 1 or 2 heteroatoms (hereinafter, ring A is referred to as A2), a compound wherein ring A is optionally substituted benzene ring (hereinafter, ring A is referred to as A3), a compound wherein ring A is

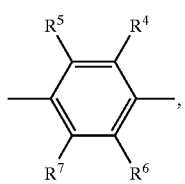

$R^4$, $R^5$, $R^6$ and $R^7$ are each independently hydrogen, halogen, hydroxy, optionally substituted lower alkyl, optionally substituted lower alkoxy, optionally substituted lower alkenyl, optionally substituted lower alkenyloxy, carboxy, optionally substituted lower alkoxycarbonyl or optionally substituted amino (hereinafter, ring A is referred to as A4), a compound wherein ring A is

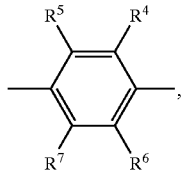

$R^4$, $R^5$, $R^6$ and $R^7$ are each independently hydrogen, halogen, lower alkyl, lower alkoxy or lower alkoxycarbonyl (hereinafter, ring A is referred to as A5), a compound wherein ring A is

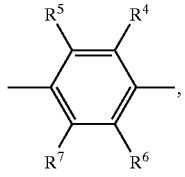

$R^4$ and $R^5$ are each independently hydrogen, halogen or lower alkoxy, $R^6$ and $R^7$ are each independently hydrogen, halogen or lower alkyl (hereinafter, ring A is referred to as A6), a compound wherein ring A is

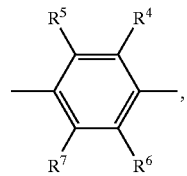

$R^4$, $R^5$, $R^6$ and $R^7$ are each independently hydrogen or halogen (hereinafter, ring A is referred to as A7), 4) a compound wherein ring B is benzene ring (hereinafter, ring B is referred to as B1), a compound wherein ring B is

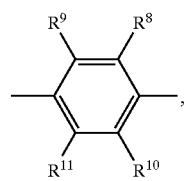

$R^8$, $R^9$, $R^{10}$ and $R^{11}$ are each independently hydrogen, halogen, hydroxy, optionally substituted lower alkyl, optionally substituted lower alkoxy, optionally substituted lower alkenyl, optionally substituted lower alkenyloxy, carboxy, optionally substituted lower alkoxycarbonyl or optionally substituted amino (hereinafter, ring B is referred to as B2), a compound wherein ring B is

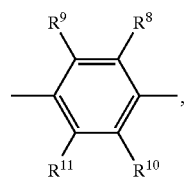

$R^8$, $R^9$, $R^{10}$ and $R^{11}$ are each independently hydrogen, halogen, hydroxy, lower alkyl, lower alkoxy or lower alkoxycarbonyl (hereinafter, ring B is referred to as B3), a compound wherein ring B is

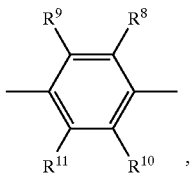

$R^8$, $R^9$, $R^{10}$ and $R^{11}$ are each independently hydrogen, hydroxy, lower alkyl or lower alkoxy (hereinafter, ring B is referred to as B4), a compound wherein ring B is

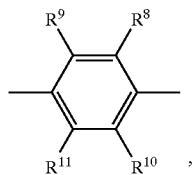

$R^8$ and $R^{11}$ are each independently hydrogen, hydroxy or lower alkyl, $R^9$ and $R^{10}$ are each independently lower alkyl, lower alkoxy or lower alkoxycarbonyl (hereinafter, ring B is referred to as B5), a compound wherein ring B is

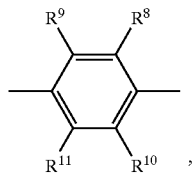

$R^8$ and $R^{11}$ are both lower alkyl, or one of them is lower alkyl and the other is hydrogen or lower alkoxy, and $R^9$ and $R^{10}$ are both hydrogen, lower alkyl or lower alkoxy (hereinafter, ring B is referred to as B6), a compound wherein ring B is

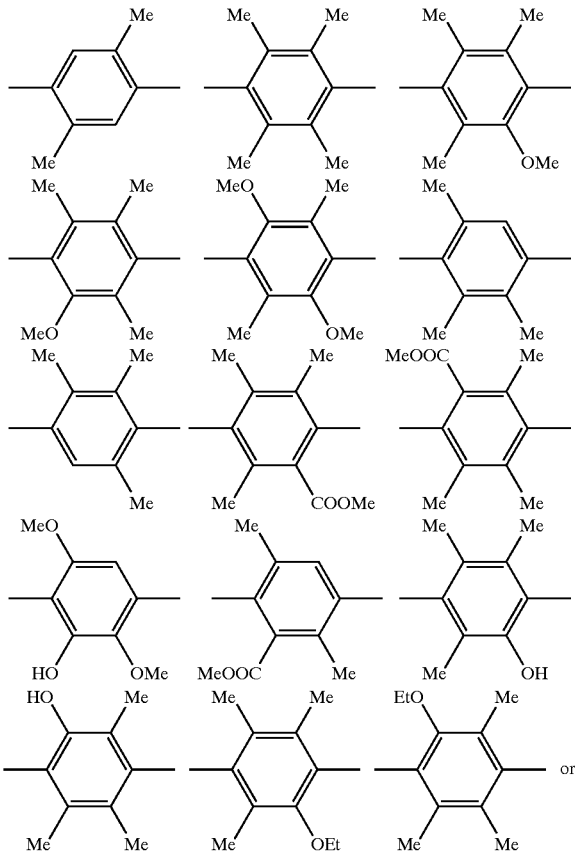

(hereinafter, ring B is referred to as B7), a compound wherein ring B is

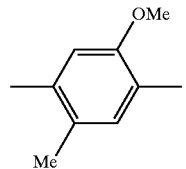

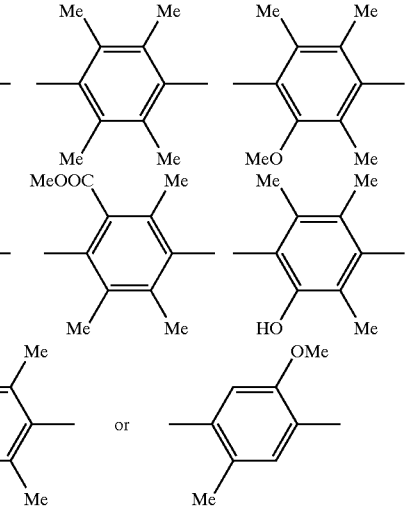

(hereinafter, ring B is referred to as B8), 5) a compound wherein ring C is optionally substituted benzene ring or optionally substituted 6-membered heterocycle (hereinafter, ring C is referred to as C1), a compound wherein ring C is optionally substituted benzene ring or optionally substituted 6-heterocycle containing 1 or 2 heteroatoms (hereinafter, ring C is referred to as C2), a compound wherein ring C is optionally substituted 6-membered heterocycle containing 1 or 2 N atoms (hereinafter, ring C is referred to as C3), a compound wherein ring C is 6-membered heterocycle optionally substituted with halogen, hydroxy, optionally substituted lower alkyl, optionally substituted lower alkoxy, optionally substituted lower alkenyl, optionally substituted lower alkenyloxy, carboxy, optionally substituted lower alkoxycarbonyl or 6-membered hetero cycle containing 1 or 2 N atoms which may be substituted with optionally substituted amino(hereinafter, ring C is referred to as C4), a compound wherein ring C is pyridine or pyrimidine optionally each substituted with halogen, hydroxy, lower alkyl, lower alkoxy or lower alkoxycarbonyl (hereinafter, ring C is referred to as C5), a compound wherein ring C is pyridine or pyrimidine optionally each substituted with lower alkyl (hereinafter, ring C is referred to as C6), a compound wherein ring C is non-substituted pyridine (hereinafter, ring C is referred to as C7), a compound wherein ring C is

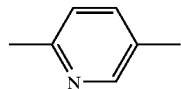

(hereinafter, ring C is referred to as C8),
6) a compound wherein $V^1$ and $V^2$ are both a single bond,
7) a compound wherein a combination of X and X', Y and Y', ring A, ring B and ring C is as follows, and $V^1$ and $V^2$ are both a single bond, (X2, Y3, A3, B2, C3), (X2, Y3, A3, B2, C5), (X2, Y3, A3, B2, C6), (X2, Y3, A3, B3, C3), (X2, Y3, A3, B3, C5), (X2, Y3, A3, B3, C6), (X2, Y3, A3, B5, C3), (X2, Y3, A3, B5, C5), (X2, Y3, A3, B6, C5), (X2, Y3, A3, B7, C5), (X2, Y3, A3, B5, C6), (X2, Y3, A3, B5, C7), (X2, Y3, A5, B2, C3), (X2, Y3, A5, B2, C5), (X2, Y3, A5, B2, C6), (X2, Y3, A5, B3, C3), (X2, Y3, A5, B3, C5), (X2, Y3, A5, B3, C6), (X2, Y3, A5, B5, C3), (X2, Y3, A5, B5, C5), (X2, Y3, A5, B6, C5), (X2, Y3, A5, B7, C5), (X2, Y3, A5, B5, C6), (X2, Y3, A5, B5, C7), (X2, Y3, A7, B2, C3), (X2, Y3, A7, B2, C5), (X2, Y3, A7, B2, C6), (X2, Y3, A7, B3, C3), (X2, Y3, A7, B3, C5), (X2, Y3, A7, B3, C6), (X2, Y3, A7, B5, C3), (X2, Y3, A7, B5, C5), (X2, Y3, A7, B6, C5), (X2, Y3, A7, B7, C5), (X2, Y3, A7, B5, C6), (X2, Y3, A7, B5, C7), (X2, Y4, A3, B2, C3), (X2, Y4, A3, B2, C5), (X2, Y4, A3, B2, C6), (X2, Y4, A3, B3, C3), (X2, Y4, A3, B3, C5), (X2, Y4, A3, B3, C6), (X2, Y4, A3, B5, C3), (X2, Y4, A3, B5, C5), (X2, Y4, A3, B6, C5), (X2, Y4, A3, B7, C5), (X2, Y4, A3, B5, C6), (X2, Y4, A3, B5, C7), (X2, Y4, A5, B2, C3), (X2, Y4, A5, B2, C5), (X2, Y4, A3, B2, C6), (X2, Y4, A5, B3, C3), (X2, Y4, A5, B3, C5), (X2, Y4, A5, B3, C6), (X2, Y4, A5, B5, C3), (X2, Y4, A5, B35, C5), (X2, Y4, A5, B6, C5), (X2, Y4, A5, B7, C5), (X2, Y4, A5, B5, C6), (X2, Y4, A5, B5, C7), (X2, Y4, A7, B2, C3), (X2, Y4, A7, B2, C5), (X2, Y4, A7, B2, C6), (X2, Y4, A7, B3, C3), (X2, Y4, A7, B3, C5), (X2, Y4, A7, B3, C6), (X2, Y4, A7, B5, C3), (X2, Y4, A7, B5, C5), (X2, Y4, A7, B6, C5), (X2, Y4, A7, B7, C5), (X2, Y4, A7, B5, C6), (X2, Y4, A7, B5, C7), (X3, Y3, A3, B2, C3), (X3, Y3, A3, B2, C5), (X3, Y3, A3, B2, C6), (X3, Y3, A3, B3, C3), (X3, Y3, A3, B3, C5), (X3, Y3, A3, B3, C6), (X3, Y3, A3, B5, C3), (X3, Y3, A3, B5, C5), (X3, Y3, A3, B5, C5), (X3, Y3, A3, B7, C5), (X3, Y3, A3, B5, C6), (X3, Y3, A3, B5, C7), (X3, Y3, A5, B2, C3), (X3, Y3, A5, B2, C5), (X3, Y3, A5, B2, C6), (X3, Y3, A5, B3, C3), (X3, Y3, A5, B3, C5), (X3, Y3, A5, B3, C6), (X3, Y3, A5, B5, C3), (X3, Y3, A5, B5, C5), (X3, Y3, A5, B6, C5), (X3, Y3, A5, B7, C5), (X3, Y3, A5, B5, C6), (X3, Y3, A5, B5, C7), (X3, Y3, A7, B2, C3), (X3, Y3, A7, B2, C5), (X3, Y3, A7, B2, C6), (X3, Y3, A7, B3, C3), (X3, Y3, A7, B3, C5), (X3, Y3, A7, B3, C6), (X3, Y3, A7, B5, C3), (X3, Y3, A7, B5, C5), (X3, Y3, A7, B6, C5), (X3, Y3, A7, B7, C5), (X3, Y3, A7, B5, C6), (X3, Y3, A7, B5, C7), (X3, Y4, A3, B2, C3), (X3, Y4, A3, B2, C6), (X3, Y4, A3, B2, C6), (X3, Y4, A3, B3, C3), (X3, Y4, A3, B3, C5), (X3, Y4, A3, B3, C6), (X3, Y4, A3, B5, C3), (X3, Y4, A3, B5, C5), (X3, Y4, A3, B6, C5), (X3, Y4, A3, B7, C5), (X3, Y4, A3, B5, C6), (X3, Y4, A3, B5, C7), (X3, Y4, A5, B2, C3), (X3, Y4, A5, B2, C5), (X3, Y4, A5, B2, C6), (X3, Y4, A5, B3, C3), (X3, Y4, A5, B3, C5), (X3, Y4, A5, B3, C6), (X3, Y4, A5, B5, C3), (X3, Y4, A5, B5, C5), (X3, Y4, A5, B6, C5), (X3, Y4, A5, B7, C5), (X3, Y4, A5, B5, C6), (X3, Y4, A5, B5, C7), (X3, Y4, A7, B2, C3), (X3, Y4, A7, B2, C5), (X3, Y4, A7, B2, C6), (X3, Y4, A7, B3, C3), (X3, Y4, A7, B3, C5), (X3, Y4, A7, B3, C6), (X3, Y4, A7, B5, C3), (X3, Y4, A7, B5, C5), (X3, Y4, A7, B6, C5), (X3, Y4, A7, B7, C5), (X3, Y4, A7, B5, C6), (X3, Y4, A7, B5, C7), (X4, Y3, A3, B2, C3), (X4, Y3, A3, B2, C5), (X4, Y3, A3, B2, C6), (X4, Y3, A3, B3, C3), (X4, Y3, A3, B3, C5), (X4, Y3, A3, B3, C6), (X4, Y3, A3, B5, C3), (X4, Y3, A3, B5, C5), (X4, Y3, A3, B6, C5), (X4, Y3, A3, B7, C5), (X4, Y3, A3, B5, C6), (X4, Y3, A3, B5, C7), (X4, Y3, A5, B2, C3), (X4, Y3, A5, B2, C5), (X4, Y3, A5, B2, C6), (X4, Y3, A5, B3, C3), (X4, Y3, A5, B3, C5), (X4, Y3, A5, B3, C6), (X4, Y3, A5, B5, C3), (X4, Y3, A5, B5, C5), (X4, Y3, A5, B6, C5), (X4, Y3, A5, B7, C5), (X4, Y3, A5, B5, C6), (X4, Y3, A5, B5, C7), (X4, Y3, A7, B2, C3), (X4, Y3, A7, B2, C5), (X4, Y3, A7, B2, C6), (X4, Y3, A7, B3, C3), (X4, Y3, A7, B3, C5), (X4, Y3, A7, B3, C6), (X4, Y3, A7, B5, C3), (X4, Y3, A7, B5, C5), (X4, Y3, A7, B6, C5), (X4, Y3, A7, B7, C5), (X4, Y3, A7, B5, C6), (X4, Y3, A7, B5, C7), (X4, Y4, A3, B2, C3), (X4, Y4, A3, B2, C5), (X4, Y4, A3, B2, C6), (X4, Y4, A3, B3, C3), (X4, Y4, A3, B3, C5), (X4, Y4, A3, B3, C6), (X4, Y4, A3, B5, C3), (X4, Y4, A3, B5, C5), (X4, Y4, A3, B6, C5), (X4, Y4, A3, B7, C5), (X4, Y4, A3, B5, C6), (X4, Y4, A3, B5, C7), (X4, Y4, A5, B2, C3), (X4, Y4, A5, B2, C5), (X4, Y4, A5, B2, C6), (X4, Y4, A5, B3, C3), (X4, Y4, A5, B3, C5), (X4, Y4, A5, B3, C6), (X4, Y4, A5, B5, C3), (X4, Y4, A5, B5, C5), (X4, Y4, A5, B6, C5), (X4, Y4, A5, B7, C5), (X4, Y4, A5, B5, C6), (X4, Y4, A5, B5, C7), (X4, Y4, A7, B2, C3), (X4, Y4, A7, B2, C5), (X4, Y4, A7, B2, C6), (X4, Y4, A7, B3, C3), (X4, Y4, A7, B3, C5), (X4, Y4, A7, B3, C6), (X4, Y4, A7, B5, C3), (X4, Y4, A7, B5, C5), (X4, Y4, A7, B6, C5) (X4, Y4, A7, B7, C5), (X4, Y4, A7, B5, C6), (X4, Y4, A7, B5, C7), (X5, Y5, A3, B2, C3), (X5, Y5, A3, B2, C5), (X5, Y5, A3, B2, C6), (X5, Y5, A3, B2, C7), (X5, Y5, A3, B2, C8), (X5, Y5, A3, B3, C3), (X5, Y5, A3, B3, C5), (X5, Y5, A3, B3, C6), (X5, Y5, A3, B3, C7), (X5, Y5, A3, B3, C8), (X5, Y5, A3, B5, C3), (X5, Y5, A3, B5, C5), (X5, Y5, A3, B5, C6), (X5, Y5, A3, B5, C7), (X5, Y5, A3, B5, C8), (X5, Y5, A3, B6, C3), (X5, Y5, A3, B6, C5), (X5, Y5, A3, B6, C6), (X5, Y5, A3, B6, C7), (X5, Y5, A3, B6, C8), (X5, Y5, A3, B7, C3), (X5, Y5, A3, B7, C5), (X5, Y5, A3, B7, C6), (X5, Y5, A3, B7, C7), (X5, Y5, A3, B7, C8), (X5, Y5, A3, B8, C3), (X5, Y5, A3, B8, C5), (X5, Y5, A3, B8, C6), (X5, Y5, A3, B8, C7), (X5, Y5, A3, B8, C8), (X5, Y5, A5, B2, C3), (X5, Y5, A5, B2, C5), (X5, Y5, A5, B2, C6), (X5, Y5, A5, B2, C7), (X5, Y5, A5, B2, C8), (X5, Y5, A5, B3, C3), (X5, Y5, A5, B3, C5), (X5, Y5, A5, B3, C6), (X5, Y5, A5, B3, C7), (X5, Y5, A5, B3, C8), (X5, Y5, A5, B5, C3), (X5, Y5, A5, B5, C5), (X5, Y5, A5, B5, C6), (X5, Y5, A5, B5, C7), (X5, Y5, A5, B5, C8), (X5, Y5, A5, B6, C3), (X5, Y5, A5, B6, C5), (X5, Y5, A5, B6, C6), (X5, Y5, A5, B6, C7), (X5, Y5, A5, B6, C8), (X5, Y5, A5, B7, C3), (X5, Y5, A5, B7, C5), (X5, Y5, A5, B7, C6), (X5, Y5, A5, B7, C7), (X5, Y5, A5, B7, C8), (X5, Y5, A5, B8, C3), (X5, Y5, A5, B8, C5), (X5, Y5, A5, B8, C6), (X5, Y5, A5, B8, C7), (X5, Y5, A5, B8, C8), (X5, Y5, A7, B2, C3), (X5, Y5, A7, B2, C5), (X5, Y5, A7, B2, C6), (X5, Y5, A7, B2, C7), (X5, Y5, A7, B2, C8), (X5, Y5, A7, B3, C3), (X5, Y5, A7, B3, C5), (X5, Y5, A7, B3, C6), (X5, Y5, A7, B3, C7), (X5, Y5, A7, B3, C8), (X5, Y5, A7, B5, C3), (X5, Y5, A7, B5, C5), (X5, Y5, A7, B5, C6), (X5, Y5, A7, B5, C7), (X5, Y5, A7, B5, C8), (X5, Y5, A7, B6, C3), (X5, Y5, A7, B6, C5), (X5, Y5, A7, B6, C6), (X5, Y5, A7, B6, C7), (X5, Y5, A7, B6, C8), (X5, Y5, A7, B7, C3), (X5, Y5, A7, B7, C5), (X5, Y5, A7, B7, C6), (X5, Y5, A7, B7, C7), (X5, Y5, A7, B7, C8), (X5, Y5, A7, B8, C3), (X5, Y5, A7, B8, C5), (X5, Y5, A7, B8, C6), (X5, Y5, A7, B8, C7), (X5, Y5, A7, B8, C8), (X5, Y5, A8, B2, C3), (X5, Y5, A8, B2, C5), (X5, Y5, A8, B2, C6), (X5, Y5, A8, B2, C7), (X5, Y5, A8, B2, C8), (X5, Y5, A8, B3, C3), (X5, Y5, A8, B3, C5), (X5, Y5, A8, B3, C6), (X5, Y5, A8, B3, C7), (X5, Y5, A8, B3, C8), (X5, Y5, A8, B5, C3), (X5, Y5, A8, B5, C5), (X5, Y5, A8, B5, C6), (X5, Y5, A8, B5, C7), (X5, Y5, A8, B5, C8), (X5, Y5, A8, B6, C3), (X5, Y5, A8, B6, C5), (X5, Y5, A8, B6, C6), (X5, Y5, A8, B6, C7), (X5, Y5, A8, B6, C8), (X5, Y5, A8, B7, C3), (X5, Y5, A8, B7, C5), (X5, Y5, A8, B7, C6), (X5, Y5, A8, B7, C7), (X5, Y5, A8, B7, C8), (X5, Y5, A8, B8, C3), (X5, Y5, A8, B8, C5), (X5, Y5, A8, B8, C6), (X5, Y5, A8, B8, C7) or (X5, Y5, A8, B8, C8).

A method of preparing a compound (I) will be explained below.

(Method of Preparing Compound (I))

A compound (I) can be synthesized by α-haloalkoxycarbonizing —NH— of a compound represented by the formula (IV)(hereinafter, referred to as a compound (IV)):

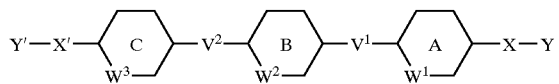

(IV)

wherein one of X and X' is —NH—, the other is —(CH$_2$)s— (wherein s is an integer of 0 to 2), —O, —NR$^A$— (wherein R$^A$ is hydrogen, optionally substituted lower alkyl, lower alkenyl or lower alkylcarbonyl) or —S(O)P— (wherein p is an integer of 0 to 2), and other symbols have the same meanings as those described above and, thereafter, reacting the carbonized compound with a suitable carboxylic acid under the suitable conditions. Such the method of synthesizing acyloxyalkyl carbamate may be carried out by a method described in WO96/18605 and the like.

(In the Case of Compound (IV) Wherein X=NH)

More specifically, a compound (IV) is reacted with chloroformic α-haloalkyl ester in an inert solvent such as diethyl ether, tetrahydrofuran, 1,4-dioxane, ethyl acetate or toluene in the presence of a base such as triethylamine or N-methylmorpholine at 0° C. to room temperature to obtain an intermediate compound represented by the above formula (V) (hereinafter, referred to as a compound (V)) quantitatively.

Then, the compound (V) is reacted with a salt (such as alkali metal salt, alkaline earth metal salt, silver salt, mercury salt or the like) of a carboxylic acid compound having a substituent R$^1$ of interest in a solvent such as N,N-dimethylformamide, N,N-dimethylacetamide, dimethylsulfoxide, sulfolane or the like at room temperature to under heating for hours to for days to obtain a compound (I). Alternatively, a free carboxylic acid may be used in the presence of an alkali metal salt, an alkaline earth metal salt, silver salt or the like of carbonate or bicarbonate to obtain a target compound. The present reaction can be carried out in the presence of KBr or NaI to substitute Cl of a compound (V) with more reactive Br or I.

Also in the case of a compound (IV) wherein X' is —NH—, a target compound can be obtained as described above. In addition, in the case wherein X and X' are both —NH—, a compound wherein X and/or X' is (are) modified for a prodrug can be obtained by adjusting an amount of chloroformic α-haloalkyl ester to be added.

A compound (IV) which is a secondary amine can be converted into a compound (I) also by a method using para-nitrophenyl acyloxyalkyl carbonate (P-NO$_2$C$_6$H$_4$OCOOC(R$^A$) (R$^B$)OCOR$^1$) described in U.S. Pat. No. 4,760,057.

Furthermore, as a method of synthesizing a compound (I), there is known a method using acyloxyalkyl carbochloridate (R$^1$COOC(R$^A$)(R$^B$)OCOCl) described in JP-A18747/1986.

A compound (IV) used in the above reaction can be synthesized by a method described in WO97/39999, or WO98/04508 or the following method.

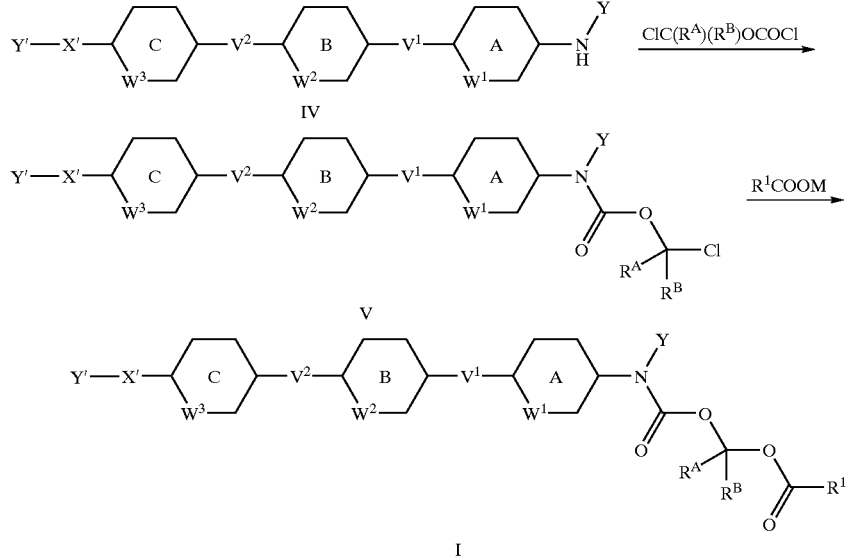

(Wherein Respective Symbols Have the Same Meanings as Those Described Above)

(Method of Preparing Compound (IV'))

A compound represented by the following formula (IV') (hereinafter, referred to as a compound (IV')) can be prepared by reacting a compound represented by the formula (VIa) (hereinafter, referred to as a compound (VIa)) with a bicyclic compound represented by the formula (VIIa) (hereinafter, referred to as a compound (VIIa)), or reacting a compound represented by the formula (VIb) (hereinafter, referred to as a compound (VIb)) with a bicyclic compound represented by the formula (VIIb) (hereinafter, referred to as a compound (VIIb))

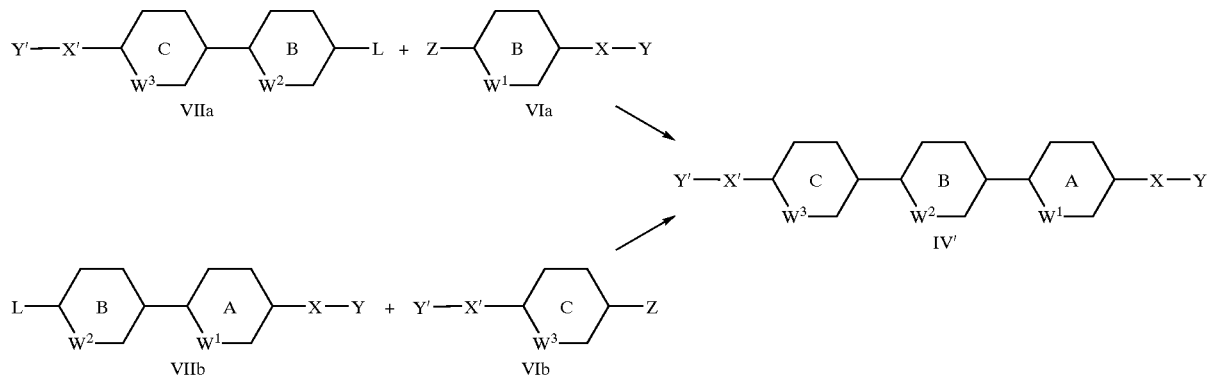

wherein one of L and Z is dihydroxyboryl, di-lower alkylboryl or di-lower alkoxyboryl, the other is halogen or $-OSO_2(C_qF_{2q+1})$ (q is an integer of 0 to 4), and other symbols have the same meanings as those described above.

A compound (VIa) and a compound (VIIa) or a compound (VIb) and a compound (VIIb) are reacted in a mixed system of a suitable solvent (such as benzene, toluene, N,N-dimethylformamide, dimethoxyethane, tetrahydrofuran, dioxane, ethanol or methanol) and water or a non-aqueous system in the presence of a palladium catalyst (such as $Pd(PPh_3)_4$, $PdCl_2(PPh_3)_2$, $PdCl_2(OAc)_2$ and $PdCl_2(CH_3CN)_2$, preferably $Pd(PPh_3)_4$) under the basic conditions (examples of the base are $K_3PO_4$, $NaHCO_3$, NaOEt, $Na_2CO_3$, $Et_4NCl$, $Ba(OH)_2$, $Cs_2CO_3$, CsF, NaOH and $Ag_2CO_3$) at room temperature to under heating for tens minutes to tens hours to obtain a compound (IV').

One of substituents L and Z in compounds to be reacted with each other may be any boryl group as far as it can be applied to a Suzuki reaction (Chemical Communication 1979, 866, Journal of Synthetic Organic Chemistry, Japan, 1993, vol. 51, No. 11, p91–100). Preferably, it is dihydroxyboryl. The other is any leaving group as far as it can be applied to a Suzuki reaction. For example, halogen or $-OSO_2(C_qF_{2q+1})$ (wherein q is an integer of 0 to 4) can be used. In particular, halogen and trifluoromethanesulfonyloxy (hereinafter, referred to as OTf) are preferable, and bromine, iodine and OTf are most preferable.

As other substituents, —X—Y and —X'—Y' for ring A, ring B and ring C of compounds (VIa), (VIIa), (VIb) and (VIIb), groups having no adverse influence on a Suzuki reaction, for example, groups other than halogen and $-OSO_2(C_qF_{2q+2})$ (wherein q is an integer of 0 to 4) are preferable.

For example, Y and Y' may be optionally substituted lower alkyl, optionally substituted lower alkenyl, optionally substituted lower alkynyl, optionally substituted cycloalkyl, optionally substituted cycloalkenyl, optionally substituted aryl or optionally substituted 5-membered or 6-membered heterocycle. In addition, when X is $-CH_2-$, Y may be optionally substituted lower alkoxy and, when X' is $-CH_2-$, Y' may be optionally substituted lower alkoxy. In addition, when X is —O— or $-NR^A-$, Y may be optionally substituted lower alkoxycarbonyl, optionally substituted lower alkylsulfonyl or optionally substituted arylsulfonyl and, when X' is —O— or $-NR^A-$, Y' may be optionally substituted lower alkoxycarbonyl, optionally substituted lower alkylsulfonyl or optionally substituted arylsulfonyl.

Even when any substituent of ring A, ring B and ring C is halogen, if the reactivity between a substituent L and a substituent Z is higher than that of halogen with either of substituents L and Z, the present reaction can proceed without any problem.

Even when any substituent —X—Y or —X'—Y' of ring A, ring B, ring C is hydroxy, the above reaction can be performed. In such the case, preferably, after protected with a hydroxy protecting group normally used (such as methoxymethyl, benzyl, t-butyldimethylsilyl, methanesulfonyl and p-toluenesulfonyl), the substituent is subjected to the above reaction and, thereafter, a normal deprotecting reaction is performed. Although as a method of synthesizing a compound (IV'), it is preferable to utilize the above Suzuki reaction for the best efficiency and more simplicity, a reaction may be performed using silicon, zinc, tin or the like in place of a boryl group in the above scheme.

For example, when one of A and Z is $-SiR^D_{3-r}(Hal)_r$ (wherein $R^D$ may be each different and is lower alkyl, Hal is halogen, and r is an integer of 1 to 3), and the other is halogen or $-OSO_2(C_qF_{2q+1})$ (wherein q is an integer of 0 to 4), a coupling reaction is performed using a normally used palladium catalyst (Synlett (1991) 845–853, J. Org. Chem. 1996, 61, 7232–7233). Examples of a preferable palladium catalyst include $(i-Pr_3P)_2PdCl_2$, $[(dcpe)PdCl_2]$(dcpe=1,2-bis(dicyclohexylphosphino)ethane and $(\eta^3-C_3H_5PdCl)_2$.

In addition, even when one of L and Z is $-SnR^E_3$ (wherein $R^E$ may be each different and is lower alkyl) and the other is halogen, acetyloxy or $-OSO_2(C_qF_{2q+1})$ (wherein q is an integer of 0 to 4), a target compound can be obtained using a normally used palladium catalyst (preferably, $Pd(PPh_3)_4$ and the like) (Angew. Chem. Int. Ed. Engl. 25 (1986) 508–524).

Even when a compound wherein one of L and Z is —Zn(Hal) (wherein Hal is halogen) and the other is halogen is reacted, a target compound can be synthesized (Acc. Chem. Res. 1982, 15, 340–348). Any palladium catalyst can be used as far as they are generally used. Preferable examples include $Pd(PPh_3)_4$, $PdCl_2(dppf)$ (dppf=1,1'-bis(diphenylphosphino) ferrocene), $PdCl_2(PPh_3)_2$, $PdCl_2(P(o-Tolyl)_3)_2$ and $Pd(OAc)_2$.

These reactions may be performed in a suitable solvent (such as N,N-dimethylformamide, tetrahydrofuran and the like) at room temperature to under heating for tens minutes to tens hours.

(Method of Preparing Compounds (VIIa) and (VIIb))

As the compounds (VIIa) and (VIIb) in the above reaction formula, the known compounds may be used, or compounds derived from a compound represented by the following formula (IXa) (hereinafter, referred to as a compound (IXa)) or a compound represented by the following formula (IXb) (hereinafter, referred to as a compound (IXb)) which is synthesized by the known method or the following method may be used:

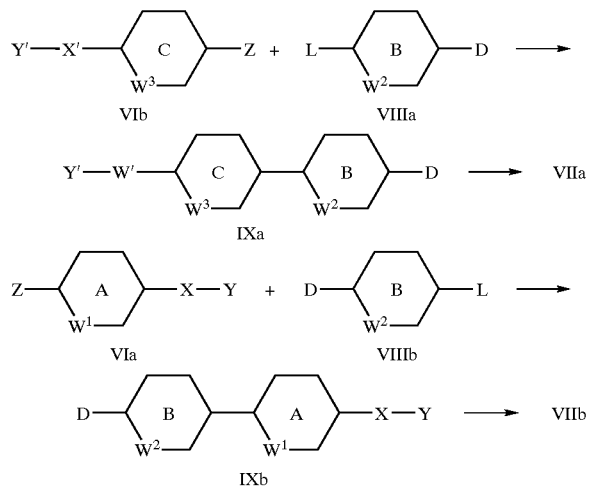

wherein D is a group having no influence on a Suzuki reaction of L and Z and, when a compound represented by the formula (VIIIa) or the formula (VIIIb) is a symmetric compound, it may be the same group as L, and other symbols have the same meanings as those described above.

First, a compound (VIb) and a compound (VIIIa) or a compound (VIa) and a compound (VIIIb) are reacted as in the above step to obtain a compound (IXa) or (IXb). When a compound (VIIIa) or (VIIIb) is not a symmetric compound, D is preferably a group which has no adverse influence on a Suzuki reaction of L and Z and can be simply derived into L. Examples of D include hydroxy, hydrogen, formyl and nitro. In L and Z, a reaction can be performed using silicon, zinc or tin in place of a boryl group as described above.

Then, D is converted into a substituent L which is applicable to a Suzuki reaction.

For example, when D is hydroxy, D is reacted with a trifluoromethanesulfonylating agent (such as trifluoromethanesulfonic anhydride, trifluoromethanesulfonyl chloride and N-phenyltrifluoromethanesulfonimide) in a suitable solvent (such as dichloromethane, chloroform, tetrahydrofuran, benzene and toluene) in the presence of a base (such as sodium hydride, pyridine, triethylamine and potassium carbonate) at −20° C. to under heating for tens minutes to tens hours to obtain a target compound wherein L is OTf.

In addition, when D is hydrogen, it is reacted with a halogenating agent (such as chlorine, bromine, iodine and N-bromosuccinic imide) in a suitable solvent (such as acetic acid, dichloromethane, chloroform, carbon tetrachloride, N,N-dimethylformamide and water) at −20° C. to under heating for tens minutes to tens hours to obtain a target compound wherein L is halogen.

When D is formyl, it is Baeyer-Villiger-oxidized to formyloxy by a normal method, which is further hydrolyzed to hydroxy. Thereafter, the same procedures as those described above can afford a compound wherein L is OTf.

When D is nitro, it may be reduced to amino which is subjected to a Sandmeyer reaction to obtain a compound wherein L is halogen.

Among a compound (VIIb), a compound represented by the following formula (VIIb');

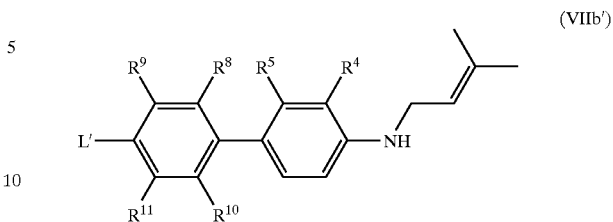

wherein one of $R^4$ and $R^5$ is hydrogen and the other is halogen, $R^8$ and $R^{10}$ are each independently hydrogen, hydroxy or lower alkyl, $R^9$ and $R^{10}$ are each independently lower alkyl, lower alkoxy or lower alkoxycarbonyl, L' is dihydroxyboryl, di-lower alkylboryl or di-lower alkoxyboryl, is particularly preferable. Most preferable L' is dihydroxyboryl. By using this intermediate, it can be directly subjected to a Suzuki reaction to synthesize a target compound (IV') without troublesome protection and deprotection reaction.

This compound (VIIb') can be also synthesized by the following method:

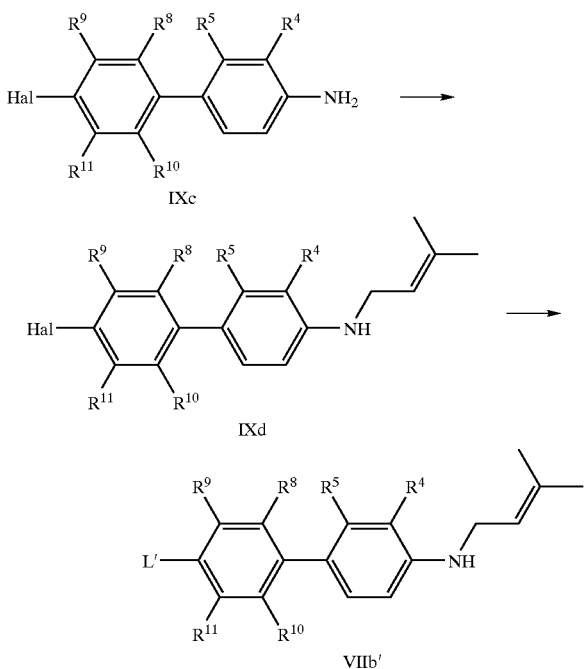

wherein respective symbols have the same meanings as those described above.

First, the known compound (IXc) or a compound (IXc) obtained by a normal method and 3-methyl-2-butenal are reacted with a reducing agent such as sodium borohydride, sodium cyanotrihydroborohydride, sodium triacetoxyborohydride, sodium trimethoxyborohydride and diisopropoxyboron chloride in a suitable solvent such as dichloromethane, dichloroethane, tetrahydrofuran, dimethoxyethane, dioxane, toluene or benzene in the presence of a neutral to acidic compound, preferably an acidic compound such as acetic acid at 0C to under heating for tens minutes to tens hours to obtain a compound (IXd). The resulting compound is reacted with n-butyllithium, sec-butyllithium, phenyllithium or the like in a suitable solvent such as tetrahydrofuran, diethylether, dimethoxyethane or the like at −100° C. to room temperature to obtain a lithium salt which can be reacted with a borate ester such as triisopropyl borate, trimethyl borate, tributyl borate or the like to obtain a compound (VIIb').

(Method of Preparing Compound (IV''))

A compound represented by the following formula (IV'') (hereinafter, referred to as a compound (IV'')) can be prepared by a Suzuki reaction of a compound represented by the formula (X) (hereinafter, referred to as a compound (X)) and a compound represented by the formula (VIa) (hereinafter, referred to as a compound (VIa)) or condensation of a compound represented by the formula (XI) (hereinafter, referred to as a compound (XI)) and a compound represented by the formula (XII) (hereinafter, referred to as a compound (XII))

In addition, a compound wherein $V^2$ for a target compound is —CO— may be also obtained by reacting a compound wherein $V^2$ is —CH(OH)— using an oxidizing agent such as chromic anhydride and a Jones regent in a solvent such as t-butyl alcohol and acetone at 0° C. to under heating for hours. A compound wherein $V^2$ for a target compound is —CH(OH)— may be also prepared by reducing a compound wherein $V^2$ is —CO— with sodium borohydride or aluminium lithium hydride in a suitable solvent (such as diethyl ether, tetrahydrofuran, dimethoxyethane, dioxane, methanol and ethanol).

When $V^2$ for a target compound is —CH=CH—, one of substituents M and Q is formyl and the other is halomethyl (wherein the halogen is, for example, chlorine, bromine or

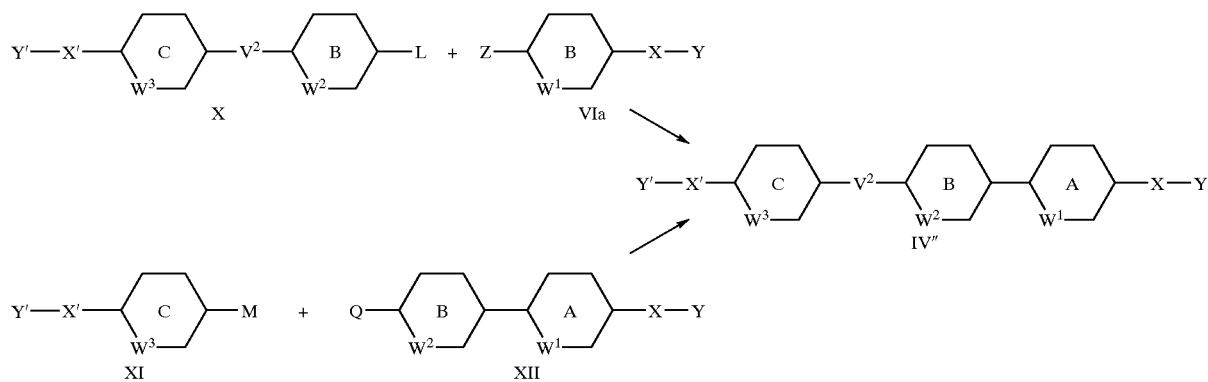

wherein one of M and Q is hydroxy or amino and the other is halogen, lower alkylsulfonyloxy, arylsulfonyloxy, lower alkylsulfonyl or arylsulfonyl or methyl having these as a substituent, or one of them is lithium or Mg(Hal) (wherein Hal is halogen) and the other is carboxy, lower alkoxycarbonyl, carbamoyl or formyl, or one of them is formyl and the other is halomethyl, or one of them is ethynyl and the other is halogen, and other symbols have the same meanings as those described above.

The various conditions in a reaction of a compound (X) and a compound (VIa) are the same as those for preparation of the compound (IV').

In a reaction of a compound (XI) and a compound (XII), when $V^2$ in a target compound is —O—, —NH—, —OCH$_2$—, —CH$_2$O— or —NHCH$_2$—, one of substituents M and Q is hydroxy or amino, and the other is a leaving group such as halogen, lower alkylsulfonyloxy, arylsulfonyloxy, lower alkylsulfonyl and arylsulfonyl or methyl having these leaving groups as a substituent. These two compounds are reacted in a suitable solvent (such as benzene, toluene, acetone, acetonitrile, N,N-dimethylformamide, dimethyl sulfoxide, pyridine, methanol and ethanol) in the presence of a base (such as sodium hydride, pyridine, triethylamine, potassium carbonate, sodium hydroxide and potassium hydroxide) and, if necessary, by adding a copper catalyst (such as copper powder, CuCl and CuO) at 0° C. to under heating for tens minutes to tens hours to obtain a target compound.

In a reaction of a compound (XI) and a compound (XII), when $V^2$ in a target compound is —CO— or —CH(OH)—, one of substituents M and Q is an organic metal such as lithium or Mg(Hal)(wherein Hal is halogen), and the other is carboxy, lower alkoxycarbonyl, carbamoyl or formyl. These two compounds are reacted in a suitable solvent (such as diethyl ether, tetrahydrofuran, dimethoxyethane and dioxane) at −78° C. to under heating for tens minutes to tens hours to obtain a target compound.

When $V^2$ for a target compound is —CH(OH)— (wherein R is lower alkyl), a compound wherein $V^2$ is —CH(OH)— is first obtained, which may be then alkylated.

iodine). In this case, a target compound can be obtained by a Wittig reaction (Organic Reaction, 1965, VOL.14, p270).

When $V^2$ for a target compound is —CH≡CH—, one of substituents M and Q is ethynyl and the other is halogen (preferably, bromine or iodine). A target compound can be synthesized by performing a coupling reaction using a normally used palladium catalyst (Synthesis (1980) 627, Tetrahedron, 1982, 38, 631).

Other substituents, —X—Y— and —X'—Y' for ring A, ring B and ring C in compounds (X), (VIa), (XI) and (XII) may be any group as far as they have no adverse influence on a Suzuki reaction of L and Z or a condensation reaction of M and Q. However, even when any substituent is halogen in a reaction of a compound (X) and a compound (VIa), if the reactivity of a substituent L and a substituent Z is higher than that of halogen with either of substituents L and Z, the present reaction can proceed without any problem. Even when any substituent is hydroxy, the above reaction can proceed. In such the case, hydroxy is preferably protected in advance and, after subjected to the above reaction, a normal deprotection reaction is performed.

As a compound (X) in the above reaction formula, the known compound may be used, or a compound synthesized by using a compound represented by the formula (XIV) (hereinafter, referred to as a compound (XIV)) by the known method or the following method may be used:

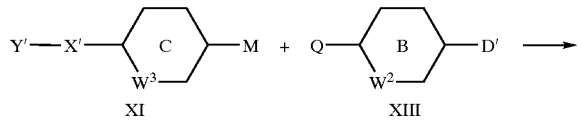

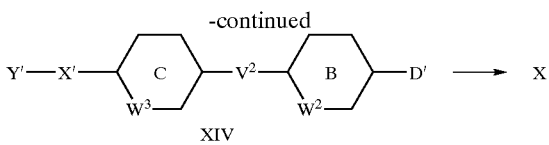

wherein D' is a group having no adverse influence on a condensation reaction of M and Q and, when, a compound represented by the formula (XIII) is a symmetric compound, D' may be the same group as Q, and other symbols have the same meanings as those described above.

When a compound (XIII) is not a symmetric compound, more specifically, D' is preferably a group which has no adverse influence on a condensation reaction of M and Q and can be simply derived into L. Examples thereof include hydrogen, formyl, and protected hydroxy and nitro. Examples of a group for protecting hydroxy include benzyl, t-butyldimethylsilyl and methoxymethyl. A method of converting D' into L is the same for conversion of D into L. Other various conditions are the same as those for a reaction of a compound (XI) and a compound (XII).

(Method of Preparing Compound (IV'''))

A compound represented by the formula (IV'''):

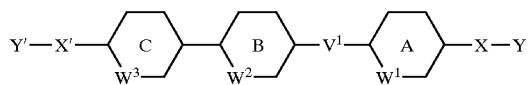

wherein respective symbols have the same meanings as those described above, can be synthesized as in the above compound (IV'').

(Method of Preparing Compound (IV) (Alternative Method))

As an alternative method of synthesizing a compound (IV), a target compound (IV) can be obtained by first constructing a tricyclic structure and, thereafter, introducing a side chain —X'—Y'. An example of a compound (IV') will be explained below:

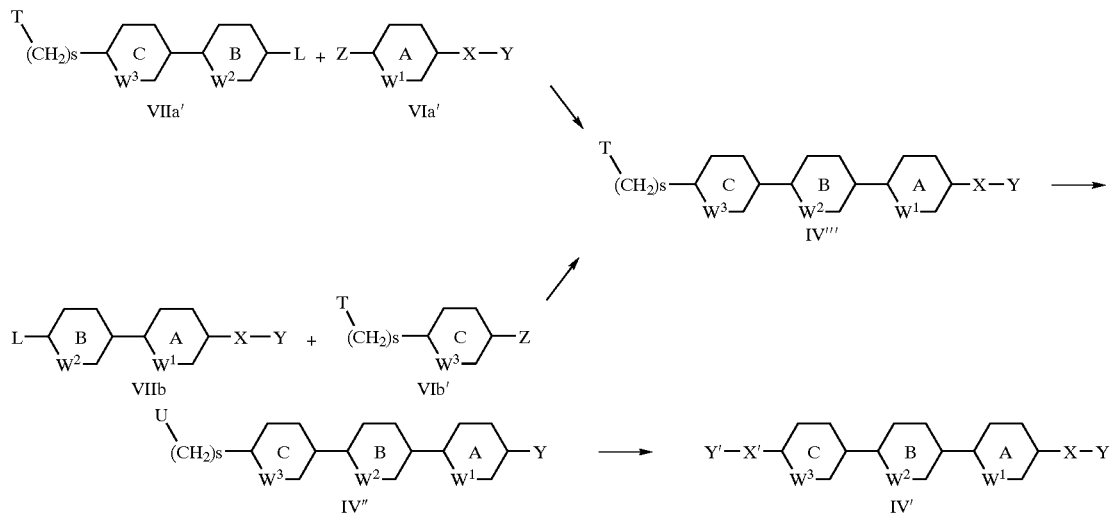

wherein T is $NH_2$, or a group which has no adverse influence on a Suzuki reaction and can be converted into U by a normal method (such as optionally protected hydroxy, lower alkylthio and arylthio), U is a leaving group (such as halogen, lower alkylsulfonyl, arylsulfonyl, lower alkylsulfonyloxy and arylsulfonyloxy), s is an integer of 0 to 2, and other symbols have the same meanings as those described above.

First, a compound represented by the formula (VIIa') (hereinafter, referred to as a compound (VIIa')) and a compound (VIa), or a compound (VIIb) and a compound represented by the formula (VIb') (hereinafter, referred to as a compound (VIb')) are reacted by the aforementioned Suzuki reaction to obtain a compound (IV'''). The present reaction may be performed as in the aforementioned reaction of a compound (VIa) and a compound (VIIa) or a compound (VIb) and a compound (VIIb).

Then, T of the resulting compound (IV''') is converted into U according to the conventional method.

For example, when T is hydroxy, it can be converted into halogen under the normal conditions, or a sulfonyl compound can be obtained by using a suitable sulfonating agent (such as methanesulfonyl chloride, p-toluenesulfonyl chloride and trifluoromethanesulfonic anhydride). When T is hydroxy which has been protected with a protecting group such as benzyl, t-butyldimethylsilyl and methoxymethyl in advance, the protected group is deprotected to hydroxy by a normal method and, thereafter, the aforementioned procedures can afford a target compound.

In addition, when T is lower alkylthio or optionally substituted arylthio, it may be converted into a corresponding sulfonyl compound using a suitable oxidizing agent (such as hydrogen peroxide, peracetic acid, m-chloroperbenzoic acid and OXON (monopersulfate compound).

Then, a compound (IV'') is subjected to a substitution reaction to obtain a compound (IV'). For example, an alcohol (Y'—OH) or an amine (Y'—$NHR^A$) and a compound wherein S=0 are reacted in a suitable solvent such as tetrahydrofuran, N,N-dimethylformamide, dioxane and diethyl ether in the presence of a base such as sodium hydride, sodium methylate and sodium bentoxide at room temperature to under heating for tens minutes to tens hours to obtain a compound (IV') wherein X' is O or $NR^A$. In addition, in order to obtain a compound (IV') wherein X is $(CH_2)s$, a nucleophilic compound having a substituent Y' of interest and a compound (IV''') wherein s=1 or 2 may be reacted under similar conditions.

(Method of Preparing Compound (VIb')]

A compound represented by the formula (VIb') (hereinafter, referred to as a compound (VIb')) in the above scheme can be synthesized, for example, by the following method. 1) In the case where Z=halogen, dihydroxyboryl, di-lower alkylboryl or di-lower alkoxyboryl

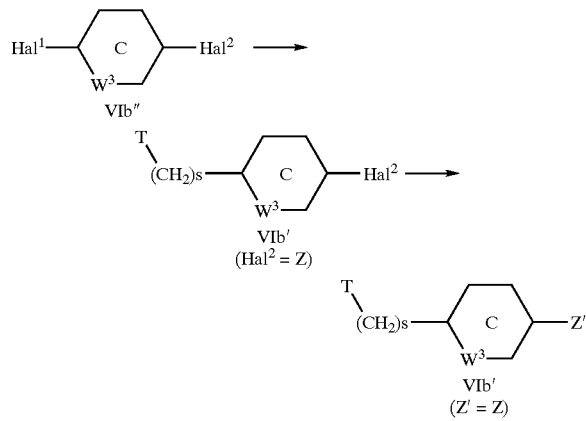

wherein $Hal^1$ and $Hal^2$ are halogen, Z' is dihydroxyboryl, di-lower alkylboryl or di-lower alkoxyboryl, and other symbols have the same meanings as those described above.

First, the known compound or a compound represented by the formula (VIb'') (hereinafter, referred to as a compound (VIb')) obtained by the conventional method is subjected to a normal substitution reaction to obtain compound (VIb':Z=halogen). The thus obtained compound can be reacted with a boric ester such as triisopropyl borate, trimethyl borate, tributyl borate and diisopropoxyboran chloride in a solvent such as tetrahydrofuran, dioxane and hexane in the presence of a base such as n-butyllithium and sec-butyllithium to obtain a compound (VIb':Z=Z').

2) In the case where Z is $OSO_2(C_qF_{2q+1})$

A compound (VIb':Z=$OSO_2(C_qF_{2q+1})$) is obtained by reacting the known compound or a compound (VIb''') obtained by the known method with fluoroalkanesulfonic acid such as trifluoromethanesulfonic anhydride in a solvent such as dichloromethane in the presence of a base such as pyridine.

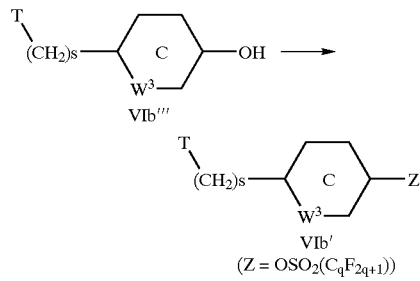

Among the above compound (VIb'), in particular, a compound wherein ring C is pyridine ring optionally substituted with lower alkyl or pyrimidine ring optionally substituted with lower alkyl, T is protected hydroxy, lower alkylthio or arylthio and Z' is dihydroxyboryl, di-lower alkylboryl or di-lower alkoxyboryl is preferable as an intermediate for a compound (IV) and a compound (I). A more preferable compound is a compound wherein T is lower alkylthio or phenylthio, Z' is dihydroxyboryl and s is 0.

Hitherto, since pyridineboronic acid has the too high water-solubility, it has been very difficult to synthesize (particularly, isolation and purification). However, by introducing a substituent T—(CH$_2$)s-, synthesis has become easy, allowing it to be prepared at a higher yield. In addition, when T is converted into a leaving group, it is possible to substitution-react with various nucleophilic regents, leading a useful intermediate for synthesizing medicines, agricultural chemicals and liquid crystal compounds having the 2,5-di-substituted pyridine and pyrimidine skeleton as a partial structure.

Regarding compounds having a substituent interfering with the above reaction, the group may be protected with a suitable protecting group in advance, and the protected group may be deprotected by the conventional method at a suitable stage. For example, when hydroxy interferes with the reaction, it may be protected with a protecting group such as methoxymethyl, methanesulfonyl, benzyl, trifluoromethanesulfonyl or t-butyldimethylsilyl and, when amino interferes with the reaction, it may be protected with a protecting group such as lower alkoxycarbonyl, lower alkenyloxycarbonyl, halogenoalkoxycarbonyl or aralkyloxycarbonyl, and the suitable protecting group may be eliminated at a suitable stage.

For example, when hydroxy is protected with methanesulfonyl, hydroxy may be reacted with methanesulfonyl chloride in a solvent such as dichloromethane, chloroform or carbon tetrachloride in the presence of a base such as triethylamine or pyridine at under ice-cooling to room temperature for several hours. When the protected hydroxy is subjected to a deprotection reaction, it may be reacted by adding 1 to 4 N sodium hydroxide, potassium hydroxide, an aqueous solution thereof, sodium methoxide or ethylmagnesium bromide in a solvent such as dimethylsulfoxide, N,N-dimethylformamide, tetrahydrofuran, dioxane and dimethoxyethane at room temperature to under heating for tens minutes to tens hours.

When methoxymethyl is used as a group for protecting hydroxy, hydroxy can be reacted with chloromethyl=methyl=ether in a solvent such as tetrahydrofuran, dioxane and dimethoxyethane in the presence of sodium hydride, diisopropylethylamine to obtain protected hydroxy. When the protected hydroxy is deprotected, a normal deprotection reaction may be carried out using hydrochloric acid or sulfuric acid in a solvent such as methanol, tetrahydrofuran and acetic acid.

When t-butyldimethylsilyl is used as a protecting group, hydroxy may be reacted with t-butyldimethylsilyl chloride or t-butyldimethylsilyltriflate in a solvent such as N,N-dimethylformamide, acetonitrile, tetrahydrofuran and dichloromethane in the presence of imidazole, triethylamine or 2,6-lutidine. When a deprotection reaction is performed by reacting with tetrabutylammonium fluoride in a solvent such as tetrahydrofuran, a protecting group can be eliminated.

A compound (I) is degraded in the living body and can be converted into a compound (IV) which is an active form. Since a compound (I) shows the extremely good oral absorbability under non-fasting or fasting as compared with a compound (IV), the high pharmacological effects can be obtained and, thus, the compound (I) is useful as a prodrug. In addition, the compound (I) has physical advantages that it has a high melting point and it does not generate static electricity and, thus, it can be simply formulated into preparations.

A compound (IV) inhibits the mitogen reaction and/or cytokine reaction, and shows the strong immunosuppressive activity and antiallergic activity. More specifically, the active compound has the very strong growth inhibiting activity against both T and B cells, and/or the antibody production inhibiting activity against IgE, IgG and the like. Accordingly, the present compound can be administered as a medicine for inhibiting immunoreaction or treating or preventing allergic diseases in an animal including human being.

An immunosuppressive agent or an antiallergic agent containing the present compound is useful for preventing or treating an rejection reaction against organs or tissues transplantation and a graft-versus-host reaction caused by bone marrow transplantation as well as allergic diseases such as rheumatoid arthritis, systemic lupus erythematosus, asthma, inflammatory colitis, injury in ischemia-reperfusion, allergic rhinitis, allergic conjunctivitis, atopy, urticaria and psoriasis.

When an immunosuppressive agent and/or an antiallergic agent containing the present compound is administered, administration can be performed by orally or parenterally. Oral administration may be performed by preparing into normally used dosage forms such as tablets, granules, powders, capsules, pills, solutions, syrups, buccals and sublingual tablets according to the conventional method. Parenteral administration may be suitably performed by any normally used dosage form such as injections (intramuscular or intravenous), suppositories, percutaneous absorption agents and inhalants. In particular, oral administration is preferable.

If necessary, various medical additives such as excipients, binders, wetting agents, disintegrating agents, lubricants and diluents suitable for the dosage form can be mixed with an appropriate amount of the present compound to obtain a pharmaceutical preparation. In the case of injections, the present compound may be sterilized with a suitable carrier to obtain a preparation.

More specifically, excipients include lactose, sucrose, glucose, starch, calcium carbonate and crystalline cellulose, binders include methylcellulose, carboxymethylcellulose, hydroxypropylcellulose, gelatin or polyvinylpyrrolidone, disintegrating agents include carboxymethylcellulose, sodium carboxymethylcellulose, starch, sodium alginate, agar powders and sodium lauryl sulfate, and lubricants include talc, magnesium stearate and macrogol. As a base for suppositories, cocoa butter, macrogol and methylcellulose can be used. Furthermore, when prepared into solutions or emulsified or suspended injections, normally used solubilizers, suspending agents, emulsifiers, stabilizers, preservatives and isotonic agents may be appropriately added and, when orally administered, sweetening agents and flavors may be added. A dose of an immunosuppressive agent and/or an antiallergic agent containing the present compound is desirably set considering age and weight of a patient, the type and degree of diseases, and a route of administration and, when orally administered to an adult, it is usually in a range of 0.05 to 100 mg/kg/day, preferably 0.1 to 10 mg/kg/day. When parenterally administered, a dose varies remarkably depending upon a route of administration and is usually in a range of 0.005 to 10 mg/kg/day, preferably 0.01 to 1 mg/kg/day. This may be administered by dividing into once to a few times per day.

The present invention will be explained in more detail by the following Examples but the present invention is not limited to them. The structural formulas of respective compounds in examples and reference examples are summarized in Table 1 to Table

EXAMPLES

Reference Example 1

Synthesis of Compound II-1

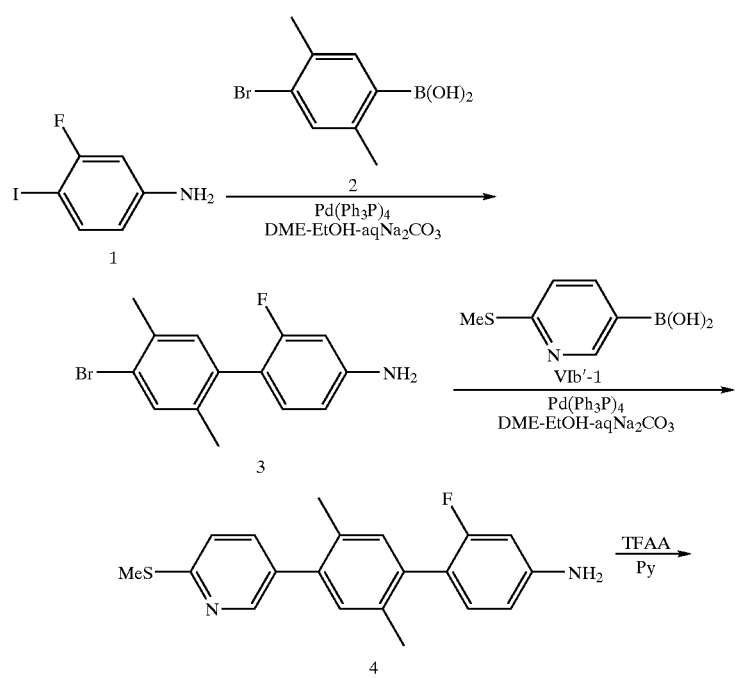

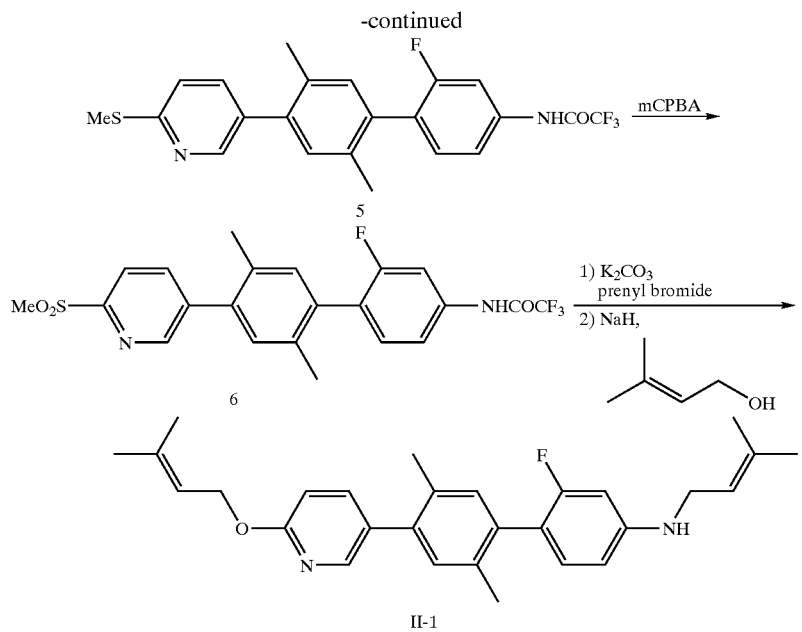

(First Step)

An aqueous solution (150 mL) of boronic acid(2) (22.88 g, 0.1 mol) and sodium carbonate (31.8 g, 0.3 mol) was added to a solution of a compound (1) (23.7 g, 0.1 mol) in dimethoxyethane (300 mL)-ethanol(150 mL), and the reaction solution was degassed. Tetrakis (triphenylphosphine) palladium (3.47 g, 3 mmol) was added, the mixture was heated at reflux for 2 hours under a nitrogen atmosphere. After diluted with water, the reaction was extracted with ethyl acetate. The extract was washed with a saturated brine, dried, concentrated, and the resulting residue was crystallized from hexane to obtain a compound (3) (24.92 g; yield 84%).

(Second Step)

According to the same manner as that of the first step, a compound (3) (20.0 g, 68.0 mmol) and boronic acid (VIb'-1) (14.94 g, 88.3 mmol) were reacted for 18 hours, and the extract residue was purified by silica gel chromatography (hexane-ethyl acetate 2:1) to obtain a compound (4) (19.24 g; yield 84%).

(Third Step)

Pyridine (6.6 mL, 81.2 mmol) followed by trifluoroacetic anhydride (10.6 mL, 75.0mmol) was added to a solution of acompound (4) (21.15 g, 62.5 mmol) in dichloromethane (200 mL) under ice-cooling, and the mixture was stirred at room temperature for 1 hour. The reaction solution was diluted with ethyl acetate. The organic layer was washed successively with water, 1N hydrochloric acid, a 5% aqueous sodium bicarbonate solution and a saturated brine, dried, and concentrated to obtain a compound (5) (22.80 g; yield 84%).

(Fourth Step)

m-Chloroperbenzoic acid (14.46 g, 83.8 mmol) was added to a solution of acompound (5) (14.0 g, 32.2 mmol) indichloromethane (300 mL) under ice-cooling, and the mixture was stirred at room temperature for 3 hours. After an aqueous solution of sodium thiosulfate was added to the reaction solution, the mixture was extracted with ethyl acetate. The organic layer was washed with an aqueous saturated sodium bicarbonate solution twice, dried and concentrated. The residue was washed with hexane to obtain a compound (6) (12.97 g; yield 86%).

(Fifth Step)

Potassium carbonate (6.67 g, 48.2 mmol) followed by prenyl bromide (4.8 mL, 41.8 mmol) was added to a solution of a compound (6) (15.0 g, 32.2 mmol) in N,N-dimethylformamide (65 mL), and the mixture was stirred at room temperature for 18 hours. The reaction solution was diluted with ethyl acetate, washed successively with water and a saturated brine, dried, concentrated, and the residue was dissolved in tetrahydrofuran (150 mL). A reaction solution prepared by adding sodium hydride (60% mineral oil, 3.85 g, 96.5 mmol) to a solution of prenol (9.8 mL, 96.5 mmol) in tetrahydrofuran (150 mL) was added under ice-cooling, and the mixture was further stirred at the same temperature for 2 hours. After the reaction mixture was diluted with ethyl acetate, the organic layer was washed successively with water and a saturated brine, dried and concentrated. The residue was purified by silica gel chromatography (hexane-ethyl acetate 7:1) to obtain a compound II-1 (12.5 g; yield 87%).

Mp: 87–88° C.

$^1$H NMR (CDCl$_3$) δ H 1.74 (s, 3H), 1.78 (s, 3H), 1.79 (s, 3H), 1.80 (s, 3H), 2.22 (s, 3H), 2.26 (s, 3H), 3.71 (d, J=6.9 Hz, 2H), 4.87 (d, J=7.2 Hz, 2H), 5.32–5.37 (m, 1H), 5.55–5.60 (m, 1H), 6.35–6.47 (m, 2H), 6.81 (dd, J=0.6, 8.4 Hz, 1H), 7.02–7.13 (m, 3H), 7.59 (dd, J=2.4, 8.4 Hz, 1H), 8.16 (dd, J=0.9, 5.7 Hz, 1H).

IR (Nujol): 3330, 2923, 2853, 1627, 1606, 1564, 1527, 1481, 1471, 1395, 1376, 1357, 1337, 1284, 1240, 1178, 1116, 990 cm$^{-1}$.

Reference Example 2 Synthesis of Compound (2)

A suspension of 1,4-dibromo-2,5-dimethylbenzene (154 g, 583 mmol) in tetrahydrofuran (1.3 L) was cooled to −78° C., and a 1.53 M butyllithium-hexane solution (400 mL, 612 mmol) was added over 30 minutes. The reaction solution was further stirred at the same temperature for 1 hour, triisopropyl borate (170 mL, 734 mmol) was added at once, and the mixture was stirred for 1 hour while the cooling bath was removed and the temperature was gradually risen. After water (300 mL) and 1N hydrochloric acid (650 mL) were added, the mixture was extracted with ethyl acetate. The extract was washed with water and a saturated brine, dried and concentrated. The crystalline residue was washed with hexane and filtered to obtain a compound (2)(115 g; yield 86%).

Example 1 Synthesis of dihydroxy-(2-methylthio-5-pyridyl)borane (VIb'-1)

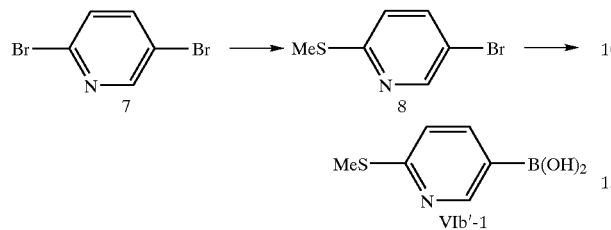

(First Step) Synthesis of 5-bromo-2-methylthio-pyridine (8)

A mixture of 2,5-dibromopyridine (7) (1100 g, 4.64 mol), tetrabutylammonium bromide (55 g, 0.037 equivalent) and a 15% aqueous sodium thiomethoxide solution (2387 g, 1.1 equivalent) was heated at 85 to 90° C. for 3.5 hours. After the reaction mixture was cooled to 10° C., the resulting solid was filtered off. The organic layer was washed with cold water (1 L) and concentrated to obtain the crude product (8) (985 g, yield 104%). The crude product (8) (908 g) was purified by recrystallization using 2-propanol (2.1 L) and water (4.2 L) to obtain a compound (8) as crystals (831 g, yield 91.5%).

Mp: 39–40° C.

$^1$H-NMR (CDCl$_3$) δ 2.54 (s, 3H), 7.07 (dd, 1H, J=0.7, 8.6 Hz), 7.58 (dd, 1H, J=2.4, 8.6 Hz), 8.49 (dd, 1H, J=0.7, 2.4 Hz).

Elemental Analysis for C$_6$H$_6$NSBr Calcd: C, 35.31; H, 2.96; N, 6.86; S, 15.71; Br, 39.15. Found: C, 35.18; H, 3.03; N, 6.95; S, 15.56; Br, 39.17; H$_2$O<0.2.

HPLC {Column: Cosmosil 5C18-AR 4.6×150 mm, Mobile phase: H$_2$O—CH$_3$CN-TFA=40-60-0.1, Rate: 1.0 mL/min, Detection (UV): 245 nm}. t$_R$ 5.4 min, (7) t$_R$ 4.3 min.

(Second Step) Synthesis of Compound VIb'-1

A solution of a 1.53 M butyllithium-hexane solution (500 mL, 765 mmol) in tetrahydrofuran (1.28 L) was cooled to −78° C., and a solution of the compound (8) (142 g, 695 mmol) obtained in the first step in tetrahydrofuran (400 mL) was added dropwise over 40 minutes. The reaction solution was stirred at the same temperature for 30 minutes, and triisopropyl borate (195 mL, 834 mmol) was added dropwise over 30 minutes. The mixture was stirred for 30 minutes while the cooling bath was removed and the reaction temperature was gradually risen. After water (320 mL) was added, the mixture was concentrated under reduced pressure, and the residue was diluted with water (710 mL) and isopropyl ether (210 mL). 3N hydrochloric acid (675 mL) was added dropwise while stirring the reaction solution at room temperature. The precipitated crystals were filtered, washed with water and isopropyl ether, and dried to obtain a compound VIb'-1 (111 g; yield 95%).

Mp: 151–154° C.

Elemental Analysis for C$_6$H$_8$BNO$_2$S Calcd: C, 42.64; H, 4.77; N, 8.29; S, 18.97 Found: C, 42.56; H. 4.88; N, 8.14; S, 18.79.

$^1$H-NMR(DMSO-d$_6$) δ 2.51 (s, 3H), 7.25 (dd, J=0.9, 8.1, 1H), 7.93 (dd, J=2.1, 8.1, 1H), 8.73 (dd, J=0.9, 2.1, 1H).

HPLC {Column: Cosmosil 5C18-AR 4.6X150 mm, Mobile phase: H$_2$O—CH$_3$CN-TFA=60-40-0.1, Rate: 1.0 mL/min, Detection (UV): 245 nm}.

t$_R$ 1.6 min, (8) t$_R$ 14.9 min, (VIb'-1) t$_R$ 2.8 min.

Example 2 Synthesis of Compound VIIb-1

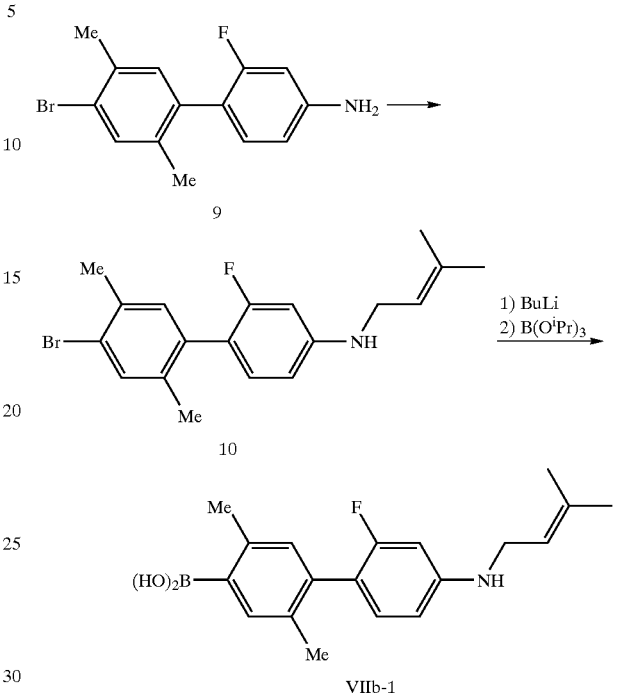

(First Step) Synthesis of Compound (10)

To a solution of a compound (9) (4.41 g, 15.0 mmol) in dichloromethane (45 mL) were successively added 3-methyl-3-butenal (1.74 mL, 18.0 mmol), acetic acid (1.8 g, 30.0 mmol) and sodium triacetoxyborohydride (6.36 g, 30.0 mmol), and the reaction solution was stirred for 15 hours. After the reaction solution was poured into water, extracted with ethyl acetate. The extract was washed with an aqueous sodium bicarbonate solution and a saturated brine, dried and concentrated. The residue was purified by silica gel chromatography (hexane-ethyl acetate 9:1) to obtain a compound (10) (4.09 g; yield 75%).

(Second Step) Synthesis of Compound VIIb-1

A solution of a compound (10) (2.4 g, 6.62 mmol) in tetrahydrofuran (24 mL) was cooled to −78° C., and 1.53 M butyllithium (10.4 mL, 15.9 mmol) was added dropwise over 30 minutes. The reaction solution was further stirred for 2 hours, triisopropyl borate (5.5 mL, 23.8 mmol) was added, and the mixture was stirred for 30 minutes while the cooling bath was removed and a temperature was gradually risen to room temperature. The reaction solution was poured into water and the mixture was extracted with ethyl acetate. The extract was washed with an aqueous ammonium chloride solution and a saturated brine, dried and concentrated. The crystalline residue was washed with hexane, and filtered to obtain a compound VIIb-1 (1.82 g; yield 87%).

$^1$H-NMR(DMSO-d$_6$) δ 1.70 (s, 3H), 1.72 (s, 3H), 2.12 (s, 3H), 2.63 (s, 3H), 3.63 (br t, 2H), 5.28 (br t, 1H), 6.01 (br t, 1H), 6.37 (dd, J=2.1, 13.2, 1H), 6.46 (dd, J=2.1, 8.4, 1H), 6.92 (s, 1H), 6.97 (t, J=8.4, 1H), 7.77 (s, 1H)

Reference Example 3 Synthesis of Compound II-10

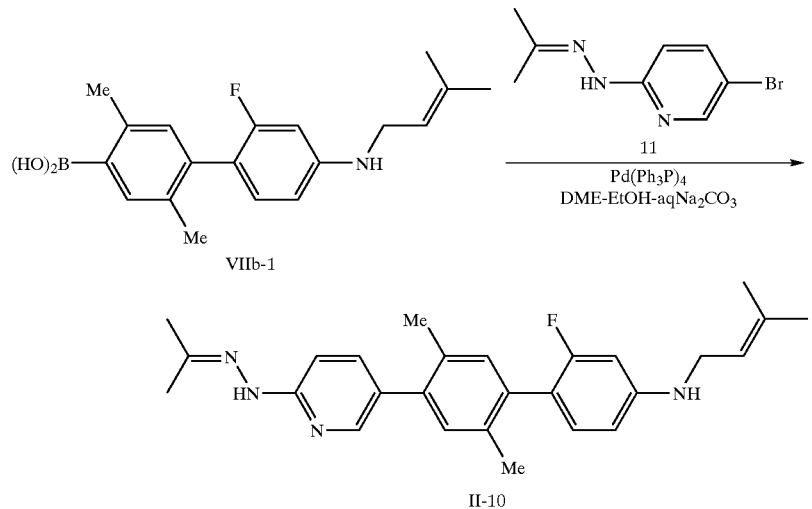

(First Step)
5-bromo-2-hydrazinopyridine (described in Journal of Heterocyclic Chemistry, 1986 (23) 1071) (376 mg, 2.0 mmol) was heated at reflux in acetone (1 mL) and ethanol (4 mL) for 15 minutes. The reaction solution was concentrated to obtain a compound (11) (456 mg, quantitative) as the crystalline residue.

(Second Step)
According to the same manner as that of Reference Example 1, a compound II-10 (268 mg; yield 83%) was obtained from the compound (11) (175 mg, 0.75 mmol) obtained in the first step and boronic acid (VIIb-1) (245 mg, 0.75 mmol).

Reference Example 4 Synthesis of {2-Fluoro-2',5'-dimethyl-4'-[6-(3-methyl-but-2-enyloxy)-pyridin-3-yl]-biphenyl-4-yl]}-(3-methyl-but-2-enyl)-carbamic acid chloromethyl ester (V-1)

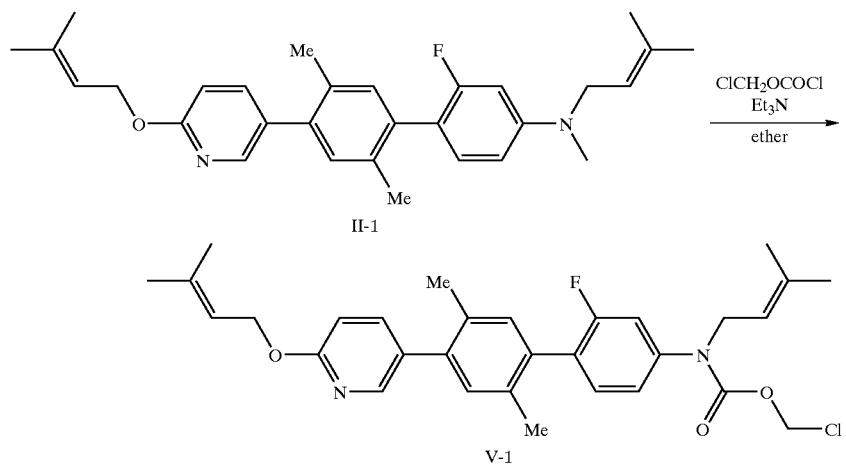

The compound II-1 (444 mg, 1 mmol) synthesized in Reference Example 1 was dissolved in anhydrous ether (40 mL) and ice-cooled, and chloromethyl chloroformate (194 mg, 1.5 mmol) and triethylamine (210 μL, 1.5 mmol) were successively added while stirring under a nitrogen atmosphere, the ice bath was removed and the mixture was continued to stir for 4 hours. The precipitates in the reaction were filtered off. The organic layer was washed with water, dried over anhydrous sodium sulfate, and the solvent was distilled off under reduced pressure to obtain a compound V-1 (540 mg) as an oil.

Elemental Analysis for $C_{31}H_{34}N_2O_3FCl$; Calcd: C, 69.33; H, 6.38; N, 5.22; F, 3.54; Cl, 6.60. Found: C, 68.85; H, 6.42; N, 5.21; F, 3.58; Cl, 7.06.

Reference Example 5 Synthesis of (3-methyl-but-2-enyl)-(5-[2,3,5,6-tetramethyl-4-[6-(3-methyl-but-2-enyloxy)-pyridin-3-yl]-phenyl]-pyridin-2-yl)-carbamic acid chloromethyl ester (V-2)

A compound II-2 (300 mg, 0.658 mmol) synthesized according to the same manner as that of Reference Example 1 was dissolved in anhydrous ether (30 mL) and ice-cooled, chloromethyl chloroformate (127 mg, 0.987 mmol) and triethylamine (128 μL, 0.921 mmol) were successively added while stirring under a nitrogen atmosphere. The ice bath was removed and the mixture was further stirred for 4 hours. The precipitates in the reaction mixture were filtered off. The organic layer was washed with water, dried over anhydrous sodium sulfate, and the solvent was distilled off under reduced pressure to obtain a compound V-2 (360 mg).

$^1$H NMR (CDCl$_3$): δ H 1.67 (3H, s), 1.71 (3H, s), 1.8 (3H, s), 1.83 (3H, s), 1.97 (6H, s), 1.99 (6H, s), 4.65 (2H, d, J=6.9 Hz), 4.89 (2H, d, J=6.9 Hz), 5.36 (1H, bt, J=6.9 Hz), 5.59 (1H, bt, J=6.9 Hz), 5.88, (2H, s), 6.86 (1H, d, J=8.4 Hz), 7.4 (1H, ddd, J=8.7 Hz, 3.3 Hz, 2.7 Hz), 7.52 (1H, ddd, J=8.4 Hz, 5.4 Hz, 2.4 Hz), 7.66 (1H, d, J=8.1 Hz), 7.97 (1H, t, J=2.7 Hz), 8.26 (1H, dd, J=3 Hz, 2.4 Hz).

Elemental Analysis for C$_{32}$H$_{38}$N$_3$O$_3$Cl; Calcd: C, 70.12; H, 6.99; N, 7.67; Cl, 6.47. Found: C, 69.72; H, 7.39; N, 7.42; Cl, 7.

Reference Example 6 Synthesis of {2-fluoro-2',5'-dimethyl-4'-[6-(3-methyl-but-2-enyloxy)-pyridin-3-yl]-biphenyl-4-yl]}-isopropyl-carbamic acid chloromethyl ester (V-3)

According to the same manner as that of Reference Example 4, a compound V-3 (271 mg) was obtained from a compound II-9 (220 mg, 0.525 mmol) and chloromethyl chloroformate (101 mg, 0.788 mmol).

$^1$H NMR (CDCl$_3$): δ H 1.22 (6H, d, J=6.6 Hz), 1.79 (3H, s), 1.82 (3H, s), 2.23 (3H, s), 2.29 (3H, s), 4.63 (1H, sep, J=6.6 Hz), 4.88 (2H, d, J=7.2 Hz), 5.58 (1H, bt, J=7.2 Hz), 5.76 (2H, bs), 6.83 (1H, d, J=8.4 Hz), 6.92–7.3 (5H, m), 7.61 (1H, dd, J=8.4 Hz, 2.4 Hz), 8.19 (1H, d, J=2.4 Hz).

Elemental Analysis for C$_{29}$H$_{32}$N$_2$O$_3$FCl; Calcd: C, 68.16; H, 6.31; N, 5.48; F, 3.72; Cl, 6.94. Found: C, 66.81; H, 6.36; N, 5.44; F, 3.51; Cl, 7.82.

Reference Example 7 Synthesis of {3'-methoxy-2',5',6'-trimethyl-4'-[6-(3-metyl-but-2-enyloxy)-pyridin-3-yl]-biphenyl-4-yl]}-(3-methyl-but-2-enyl)-carbamic acid chloromethyl ester (V-4)

According to the same manner as that of Reference Example 4, a compound V-4 (258 mg) was obtained from a compound II-4 (220 mg, 0.467 mmol) and chloromethyl chloroformate (90 mg, 0.7 mmol).

$^1$H NMR (CDCl$_3$): δ H 1.52 (3H, s), 1.72 (3H, s), 1.80 (3H, s), 1.83 (3H, s), 1.96 (6H, s), 2.07 (3H, s), 3.34 (3H, s), 4.32 (2H, d, J=7.2 Hz), 4.89 (2H, d, J=6.9 Hz), 5.34 (1H, bt, J=7.2 Hz), 5.59 (1H, bt, J=6.9 Hz), 5.81 (2H, bs), 6.84 (1H, d, J=8.7 Hz), 7.14–7.29 (4H, m), 7.55 (1H, dd, J=8.4 Hz, 2.4 Hz), 8.11 (1H, d, J=2.4 Hz).

Elemental Analysis for C$_{33}$H$_{39}$N$_2$O$_4$Cl; Calcd: C, 70.38; H, 6.98; N, 4.97; Cl, 6.3. Found: C, 69.76; H, 6.95; N, 5; Cl, 6.48.

Reference Example 8 Synthesis of {5-[3'-fluoro-2,5-dimethyoxy-3,6-dimethyl-4'-(3-methyl-but-2-enylamino)-biphenyl-4-yl]-pyridin-2-yl]}-(3-methyl-but-2-enyl-carbamic acid chloromethyl ester (V-6)

A compound II-3 (504 mg, 1 mmol) synthesized according to the same manner as that of Reference Example 1 was dissolved in anhydrous ether (100 mL) and ice-cooled, chloromethyl chloroformate (154 mg, 1.2 mmol) and triethylamine (140 μL, 1 mmol) were successively added while stirring under a nitrogen atmosphere, to react for 6 hours. The reaction was treated as in Reference Example 4, and the crude product was purified by silica gel chromatography (developing solvent: hexane-ethyl acetate (1:2)) to obtain a compound V-6 (490 mg).

$^1$H NMR (CDCl$_3$): δ H 1.67 (3H, s), 1.7 (3H, s), 1.76 (3H, s), 1.79 (3H, s), 2.06 (3H, s), 2.07 (3H, s), 3.32 (3H, s), 3.35 (3H, s), 3.78 (2H, d, J=6.6 Hz), 3.88 (1H, bs,), 4.65 (2H, d, J=7.2 Hz), 5.36 (1H, bt, J=6.6 Hz), 5.4 (1H, bt, J=6.9 Hz), 5.88 (2H, s), 6.77 (1H, t, J=8.1 Hz), 6.9–7 (2H, m), 7.66 (2H, s), 8.39 (1H, s).

Elemental Analysis for C$_{33}$H$_{39}$N$_3$O$_4$FCl; Calcd: C, 66.49; H, 6.59; N, 7.05; F, 3.19, Cl, 5.95. Found: C, 66.24; H, 6.66; N, 7.13; F, 3.11; Cl, 6.28.

Reference Example 9 Synthesis of (5-{4'-[chloromethoxycarbonyl-(3-methyl-but-2-enyl)-amino]-3'-fluoro-2,5-dimethoxy-3,6-dimethyl-dimethyl-biphenyl-4-yl]}-pyridin-2-yl)-(3-methyl-but-2-enyl)-carbamic acid chloromethyl ester (V-7)

A compound II-3 (50 mg, 0.1 mmol) was dissolved in anhydrous ether (15 mL) under a nitrogen atmosphere, chloromethyl chloroformate (51 mg, 0.5 mmol) and triethylamine (66 μL, 0.475 mmol) were successively added, which was stirred at room temperature for 24 hours. The reaction was treated as in Reference Example 4 to obtain a compound V-7 (58 mg).

$^1$H NMR (CDCl$_3$): δ H 1.51 (3H, s), 1.68 (6H, s), 1.7 (3H, s), 2.05 (3H, s), 2.07 (3H, s), 3.33 (3H, s), 3.36 (3H, s), 4.32 (2H, d, J=6.9 Hz), 4.7 (2H, d, J=6.6 Hz), 5.3 (1H, bt, J=6.6 Hz), 5.36 (1H, bt, J=6.6 Hz), 5.85 (2H, bs), 5.89 (2H, s), 7.06–7.3 (3H, m), 7.68 (2H, s), 8.4 (1H, s).

Elemental Analysis for C$_{35}$H$_{40}$N$_3$O$_6$FCl$_2$; Calcd: C, 61.05; H, 5.85; N, 6.1. Found: C, 60.98; H, 5.68; N, 6.09.

Example 3 Synthesis of succinamic acid-[{2-fluoro-2',5'-dimethyl-4'-[6-(3-methyl-but-2-enyloxy)-pyridin-3-yl]-biphenyl-4-yl]}-(3-methyl-but-2-enyl)-carbamoyloxy]-methyl ester (I-1)

A suspension of succinamic acid (105 mg, 0.9 mmol) and potassium carbonate (62 mg, 0.45 mmol) in N,N-dimethylformamide (2 mL) was stirred at room temperature for 10 minutes. Then, a compound V-1 (161 mg, 0.3 mmol) and potassium bromide (36 mg, 0.3 mmol) were successively added, which was vigorously stirred for 20 hours under an argon atmosphere. The reaction mixture was diluted with ether (20 mL) and the insoluble material was filtered off. The organic layer was washed with water, dried with anhydrous sodium sulfate, the solvent was distilled off under reduced pressure, and the material was purified by silica gel column chromatography (hexane-ethyl acetate (4:1→1:2)) to obtain a compound I-1 (116 mg, 63%).

The resulting compound has a higher melting point than that of a parent compound II-1 and improvement in the physical properties was observed.

Mp: 107–109° C.

$^1$H NMR (CDCl$_3$): δ H 1.59 (3H, s), 1.73 (3H, s), 1.79 (3H, S), 1.82 (3H, s), 2.2 (3H, s), 2.29 (3H, s), 2.55 (2H, t, J=6.6 Hz), 2.76 (2H, t, J=6.6 Hz), 4.30 (2H, d, J=7.2 Hz), 4.88 (2H, d, J=7.2 Hz), 5.31 (1H, bt, J=7.2 Hz), 5.59 (2H, bt, J=7.2 Hz), 5.81 (2H, bs), 6.82 (1H, d, J=8.1 Hz), 6.97–7.30 (5H, m), 7.6 (1H, dd, J=8.1 Hz, 2.4 Hz), 8.19 (1H, d, J=2.4 Hz).

Elemental Analysis for C$_{35}$H$_{40}$N$_3$O$_6$F; Calcd: C, 68.05; H, 6.53; N, 6.8; F, 3.08. Found: C, 67.92; H, 6.49; N, 6.96; F, 3.13.

LSIMS: m/z 618 [M+H]$^+$.

Example 4 Synthesis of carbamoyloxy-acetic acid [{2-fluoro-2',5'-dimethyl-4'-[6-(3-methyl-but-2-enyloxy)-pyridin-3-yl]-biphenyl-4-y]}-(3-methyl-but-2-enyl)-carbamoyloxy]-methyl ester (I-3)

According to the same manner as that of Example 3, a compound V-1 (161 mg, 0.3 mmol) and carbamoyloxyacetic acid (179 mg, 1.5 mmol) were reacted to obtain a compound I-3 (98 mg, 53%).

¹H NMR (CDCl₃): δ H 1.58 (3H, s), 1.73 (3H, s), 1.79 (3H, s), 1.82 (3H, s), 2.2 (3H, s), 2.28 (3H, s), 4.3 (2H, d, J=7.2 Hz), 4.66 (2H, s), 4.79 (2H, bs), 4.88 (2H, d, J=6.9 Hz), 5.31 (1H, bt, J=7.2 Hz), 5.57 (1H, bt, J=6.9 Hz), 5.87 (2H, bs), 6.82 (1H, d, J=8.7 Hz), 7–7.30 (5H, m), 7.59 (1H, dd, J=8.4, 2.4 Hz), 8.18 (1H, d, J=2.4 Hz).

Elemental Analysis for C₃₄H₃₈N₃O₇F; Calcd: C, 65.9; H, 6.18; N, 6.78; F, 3.07. Found: C, 65.14; H, 6.47; N, 6.39; F, 2.93.

LSIMS: m/z 620 [M+H]⁺, 642 [M+Na]⁺.

Example 5 Synthesis of acetylamino-acetic acid [{2-fluoro-2',5'-dimethyl-4'-[6-(3-methyl-but-2-enyloxy)-pyridin-3-yl]-biphenyl-4-yl]}-(3-methyl-but-2-enyl)-carbamoyloxy]-methyl ester (I-5)

According to the same manner as that of Example 3, a compound I-5 (305 mg, 70%) was obtained from a compound V-1 (380 mg, 0.707 mmol) and N-acetylglycine (410 mg, 3.5 mmol).

¹H NMR (CDCl₃): δ H 1.57 (3H, s), 1.73 (3H, s), 1.79 (3H, s), 1.82 (3H, s), 2.05 (3H, s), 2.2 (3H, s), 2.28 (3H, s), 4.12 (2H, d, J=5.4 Hz), 4.38 (2H, d, J=7.2 Hz), 4.88 (2H, d, J=6.9 Hz), 5.3 (1H, bt, J=7.2 Hz), 5.57 (1H, bt, J=7.2 Hz), 5.86 (2H, bs), 5.93 (1H, bs), 6.82 (1H, d, J=8.1 Hz), 7–7.3 (5H, m), 7.59 (1H, dd, J=8.4, 2.4 Hz), 8.17 (1H, d, J=2.1 Hz).

Elemental Analysis for C₃₅H₄₀N₃O₆F; Calcd: C, 68.06; H, 6.53; N, 6.8; F, 3.08. Found: C, 67.91; H, 6.58; N, 7; F, 2.91.

LSIMS: m/z 617 M⁺, 640 [M+Na]⁺.

Example 6 Synthesis of 4-acetylamino-4-carbamoyl-butyric acid [{2-fluoro-2',5'-dimethyl-4'-[6-(3-methyl-but-2-enyloxy)-pyridin-3-yl]-biphenyl-4-yl}-(3-methyl-but-2-enyl)-carbamoyloxy]-methyl ester (I-6)

According to the same manner as that of Example 3, a compound I-6 (225 mg, 65%) was obtained from a compound V-1 (269 mg, 0.5 mmol) and N-acetyl-L-isoglutamine (470 mg, 2.5 mmol).

Mp: 85–87° C.

¹H NMR (CDCl₃): δ H 1.57 (3H, s), 1.73 (3H, s), 1.8 (3H, s), 1.83 (3H, s), 1.95 (1H, m), 2.02 (3H, s), 2.19 (1H, M), 2.2 (3H, s), 2.28 (3H, s), 2.49 (1H, m), 2.63 (1H, m), 4.12 (2H, d, J=5.4 Hz), 4.3(2H, d, J=7.2 Hz), 4.54 (1H, td, J=8.1 Hz, 5.1 Hz), 4.89(2H, d, J=7.2 Hz), 5.31 (1H, bt, J=7.2 Hz), 5.33 (1H, bs), 5.58 (1H, bt, J=7.2 Hz), 5.8 (2H, bs), 6.35 (1H, d, J=5.1 Hz), 6.37 (1H, bs), 6.84 (1H, d, J=8.4 Hz), 7.03–7.3 (5H, m), 7.62 (1H, dd, J=8.4, 2.4 Hz), 8.18 (1H, d, J=2.4 Hz).

Elemental Analysis for C₃₈H₄₅N₄O₇F; Calcd: C, 66.26; H, 6.59; N, 8.13; F, 2.76. Found: C, 65.99; H, 6.59; N, 8.18; F, 2.71.

LSIMS: m/z 688 M⁺, 611 [M+Na]⁺.

Example 7 Synthesis of succinamic acid [(3-methyl-but-2-enyl)-(5-{2,3,5,6-tetramethyl-4-[6-(3-methyl-but-2-enyloxy)-pyridin-3-yl]-phenyl}-pyridin-2-yl)-carbamoyloxy]-methyl ester (I-19)

According to the same manner as that of Example 3, a compound I-13 (211 mg, 74%) was obtained from a compound V-2 (250 mg, 0.456 mmol) and succinamic acid (267 mg, 2.28 mmol).

Mp: 124–126° C.

¹H NMR (CDCl₃): δ H 1.67 (3H, 5), 1.7 (3H, s), 1.8 (3H, s), 1.83 (3H, s), 1.97 (6H, s), 1.99 (6H, s), 2.56 (2H, t, J=6.6 Hz), 2.77 (2H, t, J=6.6 Hz), 4.63 (2H, d, J=6.9 Hz), 4.89 (2H, d, J=6.9 Hz), 5.31 (1H, bt, J=7.2 Hz), 5.35 (1H, bt, J=6.6 Hz), 5.37 (1H, bs), 5.59 (1H, bt, J=6.9 Hz), 5.61 (1H, bs), 5.89 (2H, b), 6.86 (1H, d, J=8.7 Hz), 7.37–7.67 (3H, m), 7.97 (1H, s), 8.25 (1H, bs).

Elemental Analysis for C₃₆H₄₄N₄O₆; Calcd: C, 68.77; H, 7.05; N, 8.41. Found: C, 68.52; H, 7.04; N, 8.79.

Example 8 Synthesis of succinamic acid [{5-[3'-fluoro-2,5-dimethoxy-3,6-dimethyl-4'-(3-methyl-but-2-enylamino)-biphenyl-4-yl]-pyridin-2-yl}-(3-methyl-but-2-enyl)-carbamoyloxy]-methyl ester (I-37)

According to the same manner as that of Example 3, a compound I-25 (295 mg, 69%) was obtained from a compound V-6 (375 mg, 0.63 mmol) and succinamic acid (368 mg, 3.15 mmol).

Mp: 136–138° C.

¹H NMR (CDCl₃): δ H 1.66 (3H, s), 1.69 (3H, s), 1.75 (3H, s), 1.79 (3H, s), 2.06 (3H, s), 2.07 (3H, s), 2.55 (2H, t, J=6.6 Hz), 2.76 (2H, t, J=6.6 Hz), 3.31 (3H, s), 3.35 (3H, s), 3.78 (2H, d, J=6.6 Hz), 4.63 (2H, d, J=6.9 Hz), 5.34 (1H, bt, J=6.6 Hz), 5.35 (1H, bs), 5.4 (1H, bt, J=6.6 Hz), 5.61 (1H, bs), 5.88 (2H, s), 6.78 (1H, t, J=8.4 Hz), 6.93–6.97 (2H, m), 7.65 (2H, bs), 8.38 (1H, bs).

Elemental Analysis for C₃₇H₄₅N₄O₇F; Calcd: C, 65.66; H, 6.7; N, 8.28; F, 2.81. Found: C, 65.39; H, 6.7; N, 8.07; F, 2.75.

Example 9 Synthesis of succinamic acid [(5-{4'-[(3-carbamoyl-propionyloxymethoxycarbonyl)-(3-methyl-but-2-enyl)-amino]3'-fluoro-3,6-dimethoxy-2,5-dimethyl-biphenyl-4-yl}-pyridin-2-yl)-(3-methyl-but-2-enyl)-carbamoyloxy]-methyl ester (I-55)

According to the same manner as that of Example 3, a compound I-37 (52 mg, 76%) was obtained from a compound V-7 (55 mg, 0.08 mmol) and succinamic acid (94 mg, 0.8 mmol).

¹H NMR (CDCl₃): δ H 1.5 (3H, s), 1.67 (3H, s), 1.69 (3H, s), 1.7 (3H, s), 2.05 (3H, s), 2.06 (3H, s), 2.58 (4H, m), 2.77 (2H, m), 3.32 (3H, s), 3.35 (3H, s), 4.29 (2H, d, J=6.9 Hz), 4.64 (2H, d, J=6.9 Hz), 5.32 (2H, m), 5.4 (2H, bs), 5.68 (2H, bs), 5.75 (2H, bs), 5.89 (2H, s), 7.05–7.25 (3H, m), 7.67 (2H, s), 8.38 (1H, s).

Elemental Analysis for C₄₃H₅₂N₅O₁₂F; Calcd: C, 60.77; H, 6.17; N, 8.24; F, 2.24. Found: C, 59.57; H, 6.18; N, 7.98; F, 2.18.

Example 10 Synthesis of succinamic acid [{3'-methoxy-2',5',6'-trimethyl-4'-[6-(3-methyl-but-2-enyloxy)-pyridin-3-yl]-biphenyl-4-yl}-(3-methyl-but-2-enyl)-carbamoyloxy]-methyl ester (I-163)

According to the same manner as that of Example 3, a compound I-109 (218 mg, 78%) was obtained from a compound V-4 (243 mg, 0.432 mmol) and succinamic acid (253 mg, 2.16 mmol).

Mp: 107–108° C.

¹H NMR (CDCl₃): δ H 1.53 (3H, s), 1.71 (3H, s), 1.83 (3H, s), 1.95 (6H, s), 2.06 (3H, s), 2.54 (2H, t, J=6.3 Hz), 2.75 (2H, t, J=6.3 Hz), 3.33 (3H, s), 4.3 (2H, d, J=6.6 Hz), 4.88 (2H, d, J=6.9 Hz), 5.32 (1H, bt, J=6.6 Hz), 5.35 (1H, bs), 5.59 (1H, bt, J=6.9 Hz), 5.6 (1H, bs), 5.82 (2H, bs), 6.84 (1H, d, J=8.7 Hz), 7.13–7.3 (4H, m), 7.55 (1H, dd, J=8.7 Hz, 2.4 Hz), 8.11 (1H, d, J=2.4 Hz).

Elemental Analysis for $C_{37}H_{45}N_3O_7$; Calcd: C, 69.03; H, 7.05; N, 6.53. Found: C, 68.95; H, 7.02; N, 6.57.

Example 11 Synthesis of succinamic acid ({2-fluoro-2',5'-dimethyl-4'-[6-(3-methyl-but-2-enyloxy)-pyridin-3-yl]biphenyl-4-yl}-isopropyl-carbamoyloxy)-methyl ester (I-121)

According to the same manner as that of Example 3, a compound I-121 (122 mg, 42%) was obtained from a compound V-3 (250 mg, 0.489 mmol) and succinamic acid (286 mg, 2.45 mmol).

$^1$H NMR (CDCl$_3$): δ H 1.21 (6H, d, J=6.6 Hz), 1.79 (3H, s), 1.82 (3H, s), 2.22 (3H, s), 2.29 (3H, s), 2.54 (2H, t, J=6.3 Hz), 2.74 (2H, t, J=6.3 Hz), 4.6 (1H, sep, J=6.6 Hz), 4.88 (2H, d, J=7.2 Hz), 5.58 (1H, bt, J=7.2 Hz), 5.35 (1H, bs), 5.6 (1H, bs), 5.76 (2H, bs), 6.82 (1H, d, J=8.4 Hz), 6.9–7.32 (5H, m), 7.6 (1H, dd, J=8.4 Hz, 2.4 Hz), 8.19 (1H, d, J=2.4 Hz).

Elemental Analysis for $C_{33}H_{38}N_3O_6F$; Calcd: C, 66.99; H, 6.47; N, 7.1; F, 3.21. Found: C, 66.2; H, 6.58; N, 7; F, 3.05.

Example 12 Synthesis of 2-acetylamino-succinamic acid [{2-fluoro-2',5'-dimethyl-4'-[6-(3-methyl-but-2-enyloxy)-pyridin-3-yl]-biphenyl-4-yl}-((E)-3-methyl-but-2-enyl)-carbamoyloxy]-methylester (I-13)

According to the same manner as that of Example 3, a compound I-13 (201 mg, 50%) was obtained from a compound V-1 (322 mg, 0.6 mmol) and N-acetyl-L-aspartic acid (523 mg, 3 mmol).

Mp: 130–133° C.

$^1$H-NMR (CDCl$_3$): δ H 1.58 (3H, s), 1.74 (3H, s), 1.79 (3H, s), 1.83 (3H, s), 2.05 (3H, s), 2.21 (3H, s), 2.28 (3H, s), 2.77 (1H, dd, J=15.9, 4.2 Hz), 3.01 (1H, dd, J=15.9, 4.5 Hz), 4.3 (2H, d, J=6.6 Hz), 4.86 (1H, t, J=4.2 Hz), 4.88 (2H, d, J=6.9 Hz), 5.31 (1H, bt, J=6.6 Hz), 5.48 (1H, bs), 5.58 (1H, bt, J=6.9 Hz), 5.75–5.92 (3H, bm), 6.8 (1H, d, J=7.5 Hz), 6.83 (1H, d, J=8.7 Hz), 7.05–7.3 (5H, m), 7.61 (1H, dd, J=8.7, 2.1 Hz), 8.18 (1H, d, J=2.1 Hz).

Elemental Analysis for $C_{37}H_{43}N_4O_7F$; Calcd: C, 65.86; H, 6.42; N, 8.3; F, 2.82. Found: C, 65.57; H, 6.42; N, 8.27; F, 2.75.

ESIMS: m/z 675 [M+H]$^+$, 697 [M+Na]$^+$, 713 [M+K]$^+$.

Example 13 Synthesis of 3-acetylamino-succinamic acid [{2-fluoro-2',5'-dimethyl-4'-[6-(3-methyl-but-2-enyloxy)-pyridin-3-yl]-biphenyl-4-yl}-((E)-3-methyl-but-2-enyl)-carbamoyloxy]-methyl ester (I-14)

According to the same manner as that of Example 3, a compound I-14 (255 mg, 67%) was obtained from a compound V-1 (300 mg, 0.56 mmol)and N-acetyl-L-isoasparagine(117 mg, 0.67 mmol).

Mp: 137–140° C.

$^1$H-NMR (CDCl$_3$): δ H 1.58 (3H, s), 1.73 (3H, s), 1.79 (3H, s), 1.82 (3H, s), 2.03 (3H, s), 2.2 (3H, s), 2.28 (3H, s), 2.69 (1H, dd, J=17.1, 6.9 Hz), 3.05 (1H, dd, J=17.1, 4.5 Hz), 4.3 (2H, d, J=7.2 Hz), 4.85 (1H, t, J=4.2 Hz), 4.88 (2H, d, J=6.9 Hz), 5.31 (1H, bt, J=7.2 Hz), 5.55 (1H, bs), 5.57 (1H, bt, J=6.9 Hz), 5.8 (1H, bs), 5.82 (1H, bs), 6.55 (1H, bs), 6.82 (1H, d, J=8.4 Hz), 6.88 (1H, d, J=7.5 Hz), 7.01–7.3 (5H, m), 7.6 (1H, dd, J=8.4, 2.4 Hz), 8.17 (1H, d, J=2.4 Hz).

Elemental Analysis for $C_{37}H_{43}N_4O_7F$; Calcd: C, 65.86; H, 6.42; N, 8.3; F, 2.82. Found: C, 65.75; H, 6.4; N, 8.54; F, 2.74.

ESIMS: m/z 674 [M]$^+$, 675 [M+H]$^+$, 697 [M+Na]$^+$.

Example 14 Synthesis of 2-acetylamino-4-carbamoyl-butyric acid [{2-fluoro-2',5'-dimethyl-4'-[6-(3-methyl-but-2-enyloxy)-pyridin-3-yl]-biphenyl-4-yl}-((E)-3-methyl-but-2-enyl)-carbamoyloxy]-methyl ester (I-15)

According to the same manner as that of Example 6, a compound I-15 (156 mg, 61%) was obtained from a compound V-1 (200 mg, 0.372 mmol) and N-acetyl-L-glutamine (351 mg, 1.86 mmol).

Mp: 110–113° C.

PMR (CDCl$_3$): δ H 1.58 (3H, s), 1.74 (3H, s), 1.8 (3H, s), 1.83 (3H, s), 2.04 (3H, s), 2.2 (3H, s), 2.01–2.4 (4H, m), 4.29 (2H, d, J=7.2 Hz), 4.62 (1H, td, J=8.1 Hz, 5.1 Hz), 4.88 (2H, d, J=7.2 Hz), 5.3 (1H, bt, J=7.2 Hz), 5.36 (1H, bs), 5.58 (1H, bt, J=7.2 Hz), 5.78 (1H, bs), 5.91 (1H, bs), 6.1 (1H, bs), 6.81 (1H, d, J=8.4 Hz), 7.01–7.3 (5H, m), 7.6 (1H, dd, J=8.4, 2.4 Hz), 8.18 (1H, d, J=2.4 Hz).

Elemental Analysis for $C_{38}H_4N_{45}O_7F$; Calcd: C, 66.26; H, 6.59; N, 8.13; F, 2.76. Found: C, 66.03; H, 6.62; N, 8.09; F, 2.7.

ESIMS: m/z 688 [M]$^+$, 689 [M+H]$^+$.

Example 15 Synthesis of (2-acetylamino-ethanoylamino)-acetic acid [{2-fluoro-2',5'-dimethyl-4'-[6-(3-methyl-but-2-enyloxy)-pyridin-3-yl]-biphenyl-4yl]}-((E)-3-methyl-but-2-enyl)-carbamoyloxy]-methyl ester (I-16)

According to the same manner as that of Example 3, a compound I-16 (255 mg, 63%) was obtained from a compound V-1 (322 mg, 0.6 mmol) and N-acetyl-glycylglycine (523 mg, 3 mmol).

The present compound has a higher melting point as compared with a parent compound II-1 and improvement in the physical properties was also observed. In addition, the present compound has the advantage that it can be simply formulated into a preparation because it does not generate static electricity.

Mp: 103–106° C.

$^1$H-NMR (CDCl$_3$): δ H 1.58 (3H, s), 1.73 (3H, s), 1.79 (3H, s), 1.82 (3H, s), 2.05 (3H, s), 2.2 (3H, s), 2.28 (3H, s), 3.98 (2H, d, J=5.4 Hz), 4.12 (2H, d, J=5.4 Hz), 4.29 (2H, d, J=7.5 Hz), 4.88 (2H, d, 6.6 Hz), 5.3 (1H, bt, J=7.5 Hz), 5.57 (1H, bt, J=6.6 Hz), 5.85 (2H, bs), 6.3 (1H, b), 6.62 (1H, b), 6.83 (1H, d, J=8.4 Hz), 6.95–7.3 (5H, m), 7.61 (1H, dd, J=8.4, 2.4 Hz), 8.18 (1H, d, J=2.4 Hz).

Elemental Analysis for $C_{37}H_{43}N_4O_7F$; Calcd: C, 65.86; H, 6.42; N, 8.3; F, 2.82. Found: C, 65.5; H, 6.39; N, 8.22; F, 2.76.

ESIMS: m/z 675 [M+H]$^+$, 697 [M+Na]$^+$, 713 [M+K]$^+$.

Example 16 Synthesis of 2-(2-acetylamino-propanoylamino)-acetic acid [{2-fluoro-2',-5'-dimethyl-4'-[6-(3-methyl-but-2-enyloxy)-pyridin-3-yl]-biphenyl-4-yl}-((E)-3-methyl-but-2-enyl)-carbamoyloxy]-methyl ester (I-17)

According to the same manner as that of Example 3, a compound I-17 (262 mg, 76%) was obtained from a compound V-1 (269 mg, 0.5 mmol) and N-acetyl-DL-alanylglycine(108 mg, 0.6 mmol).

Mp: 79–82° C.

$^1$H-NMR (CDCl$_3$): δ H 1.38 (3H, d, J=7.2 Hz), 1.58 (3H, s), 1.74 (3H, s), 1.79 (3H, s), 1.82 (3H, s), 2.02 (3H, S), 2.2 (3H, s), 2.28 (3H, s), 4.05 (1H, dd, J=18.3, 4.5 Hz), 4.15 (1H, dd, J=18.3, 4.5 Hz), 4.3 (2H, d, J=7.2 Hz), 4.55 (1H, dq, J=7.5, 7.2 Hz), 4.88 (2H, d, 7.2 Hz), 5.3 (1H, bt, J=7.2 Hz), 5.58 (1H, bt, J=7.2 Hz), 5.83 (2H, bs), 6.1 (1H, d, J=7.5 Hz), 6.72 (1H, t, J=4.5 Hz), 6.82 (1H, d, J=8.7 Hz), 7.02–7.3 (5H, m), 7.61 (1H, dd, J=8.7, 1.8 Hz), 8.17 (1H, d, J=1.8 Hz).

Elemental Analysis for C$_{38}$H$_{45}$N$_4$O$_7$F; Calcd: C, 66.26; H, 6.59; N, 8.13; F, 2.76. Found: C, 66.44; H, 6.73; N, 8.06; F, 2.6.

ESIMS: m/z 689 [M+H]$^+$, 711 [M+Na]$^+$, 727 [M+K]$^+$.

Example 17 Synthesis of [2-(2-acetylamino-ethanoylamino)-ethanoylamino]-acetic acid [{2-fluoro-2',5'-dimethyl-4'-[6-(3-methyl-but-2-enyloxy)-pyridin-3-yl]-biphenyl-4-yl}-((E)-3-methyl-but-2-enyl)-carbamoyloxy]-methyl ester (I-18)

According to the same manner as that of Example 3, a compound I-18 (314 mg, 77%) was obtained from a compound V-1 (301 mg, 0.56 mmol) and N-acetyl-glycylglycylglycine (259 mg, 1.1 mmol).

Mp: 171–173° C.

$^1$H-NMR (CDCl$_3$): δ H 1.58 (3H, s), 1.74 (3H, s), 1.79 (3H, s), 1.83 (3H, s), 2.04 (3H, s), 2.2 (3H, s), 2.28 (3H, s), 3.94 (2H, d, J=5.7 Hz), 4.01 (2H, d, J=6 Hz), 4.11 (2H, d, J=5.7 Hz), 4.29 (2H, d, J=6.9 Hz), 4.88 (2H, d, J=7.2 Hz), 5.3 (1H, bt, J=6.9 Hz), 5.57 (1H, bt, J=7.2 Hz), 5.82 (2H, bs), 6.4 (1H, b), 6.83 (1H, d, J=8.4 Hz), 6.85 (1H, b), 7.01–7.3 (5H, m), 7.6 (1H, dd, J=8.4, 2.4 Hz), 8.18 (1H, d, J=2.4 Hz).

Elemental Analysis for C$_{39}$H$_{46}$N$_5$O$_8$F; Calcd: C, 64.01; H, 6.34; N, 9.57; F, 2.6. Found: C, 63.88; H, 6.32; N, 9.74; F, 2.52.

ESIMS: m/z 732 [M+H]$^+$, 754 [M+Na]$^+$.

According to the same manner, compounds (I) were synthesized below. The structural formulas of intermediate compounds (II) and (V) and the present compounds (I) are shown below. Respective symbols in the Table mean as follows:

Me: methyl
Et: ethyl
Ac: acetyl
nPr: n-propyl
iPr: i-propyl

TABLE 1

| No | W$^1$ | R$^8$ | R$^9$ | R$^{10}$ | R$^{11}$ | X' |
|---|---|---|---|---|---|---|
| II-1 | 2-F-4-Me-phenyl | H | Me | Me | H | O |
| II-2 | pyridyl | Me | Me | Me | Me | O |
| II-3 | 3-F-4-Me-phenyl | Me | MeO | MeO | Me | NH |
| II-4 | 4-Me-phenyl | Me | MeO | Me | Me | O |
| II-5 | 4-Me-phenyl | Me | Me | Me | H | O |

TABLE 2

| No | R$^4$ | R$^5$ | R$^6$ | R$^7$ | R$^8$ | R$^9$ | R$^{10}$ | R$^{11}$ | C | X' | Y | Y' |
|---|---|---|---|---|---|---|---|---|---|---|---|---|
| II-6 | H | F | H | H | H | Me | Me | H | 2,5-pyrimidinyl | O | CH$_2$CH=CMe$_2$ | CH$_2$CH=CMe$_2$ |

TABLE 2-continued

| No | $R^4$ | $R^5$ | $R^6$ | $R^7$ | $R^8$ | $R^9$ | $R^{10}$ | $R^{11}$ | C | X' | Y | Y' |
|---|---|---|---|---|---|---|---|---|---|---|---|---|
| II-7 | H | H | H | H | H | H | Me | Me | H | 2,4,5,6-tetramethylpyrimidin-2-yl | O | $CH_2CH=CMe_2$ | $CH_2CH=CMe_2$ |
| II-8 | H | H | H | H | Me | MeO | Me | Me | pyridin-2,5-diyl | O | $CH_2CH=CMe_2$ | $CH_2CF_3$ |
| II-9 | H | F | H | H | H | Me | Me | H | pyridin-2,5-diyl | O | iPr | $CH_2CH=CMe_2$ |
| II-10 | H | F | H | H | H | Me | Me | H | pyridin-2,5-diyl | NH | $CH_2CH=CMe_2$ | $N=CMe_2$ |

II-7 . . . 1.75(3H, s), 1.78(3H, s), 1.79(3H, s), 1.80(3H, s), 1.98(3H, s), 2.18(6H, s), 2.28(3H, s), 3.75(2H, d, J=6.9), 4.91(2H, d, J=6.9), 5.38(1H, m), 5.58(1H, m), 6.69(2H, d, J=8.4), 6.87(1H, s), 7.15(1H, s), 7.21(2H, d, J=8.4)

II-10 . . . foam; $^1$H-NMR δ 1.74(s, 3H), 1.78(s, 3H), 1.93(s, 3H), 2.08(s, 3H), 2.22(s, 3H), 2.27(s, 3H), 3.72(br d, J=5.4, 2H), 3.77(br s, 1H), 5.35(m, 1H), 6.38(dd, J=2.4, 12.3, 1H), 6.45(dd, J=2.4, 8.4, 1H), 7.06(t, J=8.4, 1H), 7.12(s, 1H), 7.13(s, 1H), 7.27(d, J=8.4, 1H), 7.61(dd, J=2.1, 8.4, 1H), 7.68(br s, 1H), 8.13(d, J=2.1, 1H)

TABLE 3

| No | $R^2$ | $R^3$ | A, $W^1$ | $R^8$ | $R^9$ | $R^{10}$ | $R^{11}$ | X' | Y | Y' |
|---|---|---|---|---|---|---|---|---|---|---|
| V-1 | H | H | 3-fluoro-1,4-phenylene | H | Me | Me | H | O | $CH_2CH=CMe_2$ | $CH_2CH=CMe_2$ |

TABLE 3-continued

| No | R² | R³ | A/W¹ | R⁸ | R⁹ | R¹⁰ | R¹¹ | X' | Y | Y' |
|---|---|---|---|---|---|---|---|---|---|---|
| V-2 | H | H | pyridine (2,5) | Me | Me | Me | Me | O | CH₂CH=CMe₂ | CH₂CH=CMe₂ |
| V-3 | H | H | 2-F-phenyl (1,4) | H | Me | Me | H | O | iPr | CH₂CH=CMe₂ |
| V-4 | H | H | phenyl (1,4) | Me | MeO | Me | Me | O | CH₂CH=CMe₂ | CH₂CH=CMe₂ |
| V-5 | H | H | 2-F-phenyl (1,4) | H | Me | Me | H | NH | CH₂CH=CMe₂ | N=CMe₂ |

TABLE 4

| No | R² | R³ | R⁴ | R⁵ | R⁶ | R⁷ | R⁸ | R⁹ | R¹⁰ | R¹¹ | X |
|---|---|---|---|---|---|---|---|---|---|---|---|
| V-6 | H | H | F | H | H | H | Me | MeO | MeO | Me | NH |
| V-7 | H | H | F | H | H | H | Me | MeO | MeO | Me | NCOOCH₂Cl |

TABLE 5

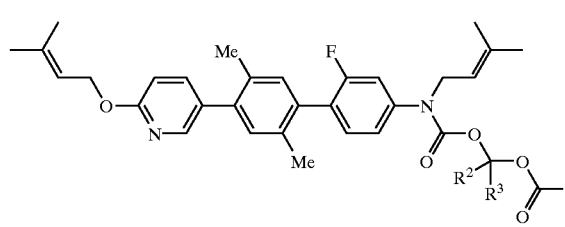

| No | R¹ | R² | R³ |
|---|---|---|---|
| I-1 | CH₂CH₂CONH₂ | H | H |
| I-2 | CH₂CH₂CONHMe | H | H |
| I-3 | CH₂OCONH₂ | H | H |
| I-4 | CH₂OCONHEt | H | H |
| I-5 | CH₂NHAc | H | H |
| I-6 | CH₂CH₂CH(CONH₂)NHAc | H | H |
| I-7 | CH₂CH(Me)CONH₂ | H | H |
| I-8 | CH₂CH₂CONHMe | Me | H |
| I-9 | CH(Me)OCONH₂ | H | H |
| I-10 | CH₂OCONHEt | Me | Me |
| I-11 | CH₂NHAc | Et | H |
| I-12 | CH(Me)CH₂CH(CONH₂)NHAc | Me | H |
| I-13 | CH(NHAc)CH₂CONH₂ | H | H |
| I-14 | CH₂CH(NHAc)CONH₂ | H | H |
| I-15 | CH(NHAc)(CH₂)₂CONH₂ | H | H |
| I-16 | CH₂NHCOCH₂NHAc | H | H |
| I-17 | CH₂NHCOCH(Me)NHAc | H | H |
| I-18 | CH₂(NHCOCH₂)₂NHAc | H | H |

TABLE 6

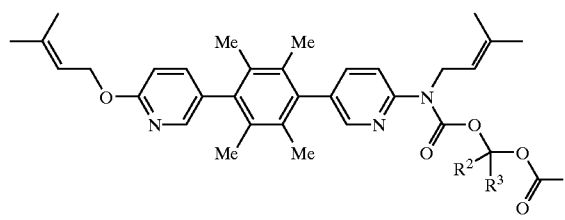

| No | R¹ | R² | R³ |
|---|---|---|---|
| I-19 | CH₂CH₂CONH₂ | H | H |
| I-20 | CH₂CH₂CONHMe | H | H |
| I-21 | CH₂OCONH₂ | H | H |
| I-22 | CH₂OCONHEt | H | H |
| I-23 | CH₂NHAc | H | H |
| I-24 | CH₂CH₂CH(CONH₂)NHAc | H | H |
| I-25 | CH₂CH(Me)CONH₂ | H | H |
| I-26 | CH₂CH₂CONHMe | Me | H |

TABLE 6-continued

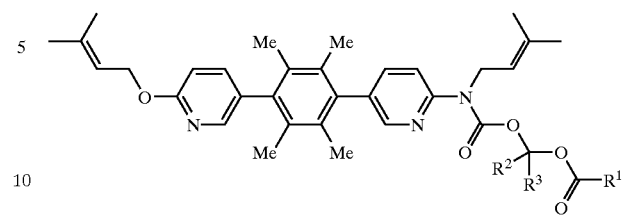

| No | R¹ | R² | R³ |
|---|---|---|---|
| I-27 | CH(Me)OCONH₂ | H | H |
| I-28 | CH₂OCONHEt | Me | Me |
| I-29 | CH₂NHAc | Et | H |
| I-30 | CH(Me)CH₂CH(CONH₂)NHAc | Me | H |
| I-31 | CH(NHAc)CH₂CONH₂ | H | H |
| I-32 | CH₂CH(NHAc)CONH₂ | H | H |
| I-33 | CH(NHAc)(CH₂)₂CONH₂ | H | H |
| I-34 | CH₂NHCOCH₂NHAc | H | H |
| I-35 | CH₂NHCOCH(Me)NHAc | H | H |
| I-36 | CH₂(NHCOCH₂)₂NHAc | H | H |

TABLE 7

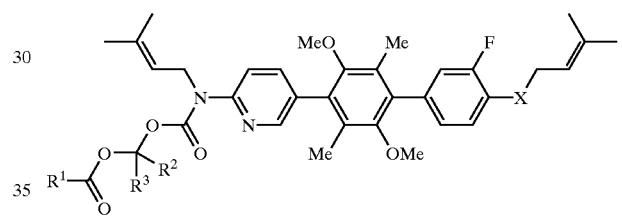

| No | R¹ | R² | R³ | X |
|---|---|---|---|---|
| I-37 | CH₂CH₂CONH₂ | H | H | NH |
| I-38 | CH₂CH₂CONHEt | H | H | NH |
| I-39 | CH₂OCONH₂ | H | H | NH |
| I-40 | CH₂OCONHMe | H | H | NH |
| I-41 | CH₂NHAc | H | H | NH |
| I-42 | CH₂CH₂CH(CONH₂)NHAc | H | H | NH |
| I-43 | CH₂CH(Me)CONH₂ | H | H | NH |
| I-44 | CH₂CH₂CONHMe | Me | H | NH |
| I-45 | CH(Me)OCONH₂ | H | H | NH |
| I-46 | CH₂OCONHEt | Me | Me | NH |
| I-47 | CH₂NHAc | Et | H | NH |
| I-48 | CH(Me)CH₂CH(CONH₂)NHAc | Me | H | NH |
| I-49 | CH(NHAc)CH₂CONH₂ | H | H | NH |
| I-50 | CH₂CH(NHAc)CONH₂ | H | H | NH |
| I-51 | CH(NHAc)(CH₂)₂CONH₂ | H | H | NH |
| I-52 | CH₂NHCOCH₂NHAc | H | H | NH |
| I-53 | CH₂NHCOCH(Me)NHAc | H | H | NH |
| I-54 | CH₂(NHCOCH₂)₂NHAc | H | H | NH |

TABLE 8

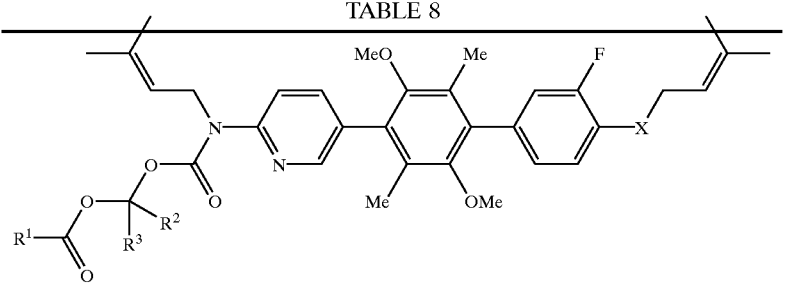

| No | R1 | R² | R³ | X |
|---|---|---|---|---|
| I-55 | CH₂CH₂CONH₂ | H | H | NCOOCH₂OCOCH₂CH₂CONH₂ |
| I-56 | CH₂CH₂CONHEt | H | H | NCOOCH₂OCOCH₂CH₂CONHEt |
| I-57 | CH₂OCONH₂ | H | H | NCOOCH₂OCOCH₂OCONH₂ |
| I-58 | CH₂OCONHMe | H | H | NCOOCH₂OCOCH₂OCONHMe |
| I-59 | CH₂NHAc | H | H | NCOOCH₂OCOCH₂NHAc |
| I-60 | CH₂CH₂CH(CONH₂)NHAc | H | H | NCOOCH₂OCOCH₂CH₂CH(CONH₂)NHAc |
| I-61 | CH₂CH(Me)CONH₂ | H | H | NCOOCH₂OCOCH₂CH(Me)CONH₂ |
| I-62 | CH₂CH₂CONHMe | Me | H | NCOOCH₂OCOCH₂CH₂CONHMe |
| I-63 | CH(Me)OCONH₂ | H | H | NCOOCH₂OCOCH(Me)OCONH₂ |
| I-64 | CH₂OCONHEt | Me | Me | NCOOCH₂OCOCH₂OCONHEt |
| I-65 | CH₂NHAc | Et | H | NCOOCH₂OCOCH₂NHAc |
| I-66 | CH(Me)CH₂CH(CONH₂)NHAc | Me | H | NCOOCH₂OCOCH(Me)CH₂CH(CONH₂)NHAc |
| I-67 | CH(NHAc)CH₂CONH₂ | H | H | NCOOCH₂OCOCH(NHCOCH₃)CH₂CONH₂ |
| I-68 | CH₂CH(NHAc)CONH₂ | H | H | NCOOCH₂OCOCH₂CH(NHCOCH₃)CONH₂ |
| I-69 | CH(NHAc)(CH₂)₂CONH₂ | H | H | NCOOCH₂OCOCH(NHCOCH₃)(CH₂)₂CONH₂ |
| I-70 | CH₂NHCOCH₂NHAc | H | H | NCOOCH₂OCOCH₂NHCOCH₂NHCOCH₃ |
| I-71 | CH₂NHCOCH(Me)NHAc | H | H | NCOOCH₂OCOCH₂NHCOCH(Me)NHCOCH₃ |
| I-72 | CH₂(NHCOCH₂)₂NHAc | H | H | NCOOCH₂OCOCH₂(NHCOCH₂)₂NHCOCH₃ |

TABLE 9

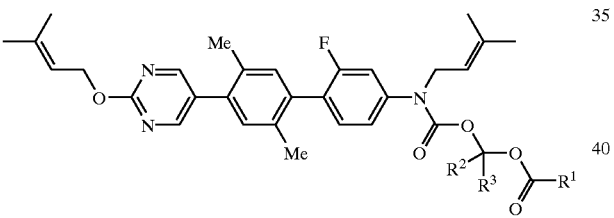

| No | R¹ | R² | R³ |
|---|---|---|---|
| I-73 | CH₂CH₂CONH₂ | H | H |
| I-74 | CH₂CH₂CONHMe | H | H |
| I-75 | CH₂OCONH₂ | H | H |
| I-76 | CH₂OCONHEt | H | H |
| I-77 | CH₂NHAc | H | H |
| I-78 | CH₂CH₂CH(CONH₂)NHAc | H | H |
| I-79 | CH₂CH(Me)CONH₂ | H | H |
| I-80 | CH₂CH₂CONHMe | Me | H |
| I-81 | CH(Me)OCONH₂ | H | H |
| I-82 | CH₂OCONHEt | Me | Me |
| I-83 | CH₂NHAc | Et | H |
| I-84 | CH(Me)CH₂CH(CONH₂)NHAc | Me | H |
| I-85 | CH(NHAc)CH₂CONH₂ | H | H |
| I-86 | CH₂CH(NHAc)CONH₂ | H | H |
| I-87 | CH(NHAc)(CH₂)₂CONH₂ | H | H |
| I-88 | CH₂NHCOCH₂NHAc | H | H |
| I-89 | CH₂NHCOCH(Me)NHAc | H | H |
| I-90 | CH₂(NHCOCH₂)₂NHAc | H | H |

TABLE 10

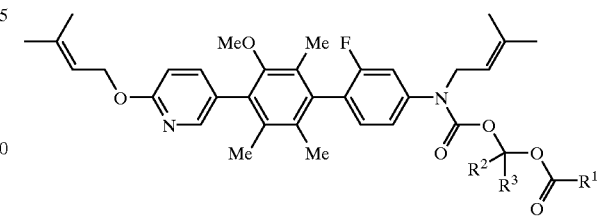

| No | R¹ | R² | R³ |
|---|---|---|---|
| I-91 | CH₂CH₂CONH₂ | H | H |
| I-92 | CH₂CH₂CONHMe | H | H |
| I-93 | CH₂OCONH₂ | H | H |
| I-94 | CH₂OCONHEt | H | H |
| I-95 | CH₂NHAc | H | H |
| I-96 | CH₂CH₂CH(CONH₂)NHAc | H | H |
| I-97 | CH₂CH(Me)CONH₂ | H | H |
| I-98 | CH₂CH₂CONHMe | Me | H |
| I-99 | CH(Me)OCONH₂ | H | H |
| I-100 | CH₂OCONHEt | Me | Me |
| I-101 | CH₂NHAc | Et | H |
| I-102 | CH(Me)CH₂CH(CONH₂)NHAc | Me | H |
| I-103 | CH(NHAc)CH₂CONH₂ | H | H |
| I-104 | CH₂CH(NHAc)CONH₂ | H | H |
| I-105 | CH(NHAc)(CH₂)₂CONH₂ | H | H |
| I-106 | CH₂NHCOCH₂NHAc | H | H |
| I-107 | CH₂NHCOCH(Me)NHAc | H | H |
| I-108 | CH₂(NHCOCH₂)₂NHAc | H | H |

TABLE 11

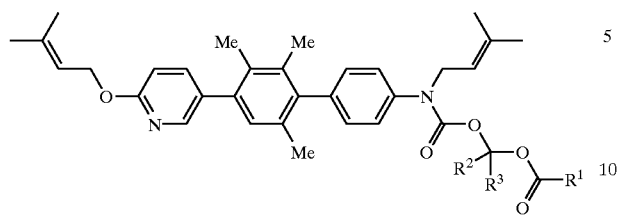

| No | R¹ | R² | R³ |
|---|---|---|---|
| I-109 | $CH_2CH_2CONH_2$ | H | H |
| I-110 | $CH_2CH_2CONHMe$ | H | H |
| I-111 | $CH_2OCONH_2$ | H | H |
| I-112 | $CH_2OCONHEt$ | H | H |
| I-113 | $CH_2NHAc$ | H | H |
| I-114 | $CH_2CH_2CH(CONH_2)NHAc$ | H | H |
| I-115 | $CH_2CH(Me)CONH_2$ | H | H |
| I-116 | $CH_2CH_2CONHMe$ | Me | H |
| I-117 | $CH(Me)OCONH_2$ | H | H |
| I-118 | $CH_2OCONHEt$ | Me | Me |
| I-119 | $CH_2NHAc$ | Et | H |
| I-120 | $CH(Me)CH_2CH(CONH_2)NHAc$ | Me | H |
| I-121 | $CH(NHAc)CH_2CONH_2$ | H | H |
| I-122 | $CH_2CH(NHAc)CONH_2$ | H | H |
| I-123 | $CH(NHAc)(CH_2)_2CONH_2$ | H | H |
| I-124 | $CH_2NHCOCH_2NHAc$ | H | H |
| I-125 | $CH_2NHCOCH(Me)NHAc$ | H | H |
| I-126 | $CH_2(NHCOCH_2)_2NHAc$ | H | H |

TABLE 12

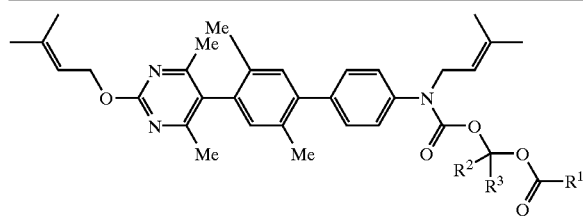

| No | R¹ | R² | R³ |
|---|---|---|---|
| I-127 | $CH_2CH_2CONH_2$ | H | H |
| I-128 | $CH_2CH_2CONHMe$ | H | H |
| I-129 | $CH_2OCONH_2$ | H | H |
| I-130 | $CH_2OCONHEt$ | H | H |
| I-131 | $CH_2NHAc$ | H | H |
| I-132 | $CH_2CH_2CH(CONH_2)NHAc$ | H | H |
| I-133 | $CH_2CH(Me)CONH_2$ | H | H |
| I-134 | $CH_2CH_2CONHMe$ | Me | H |
| I-135 | $CH(Me)OCONH_2$ | H | H |
| I-136 | $CH_2OCONHEt$ | Me | Me |
| I-137 | $CH_2NHAc$ | Et | H |
| I-138 | $CH(Me)CH_2CH(CONH_2)NHAc$ | Me | H |
| I-139 | $CH(NHAc)CH_2CONH_2$ | H | H |
| I-140 | $CH_2CH(NHAc)CONH_2$ | H | H |
| I-141 | $CH(NHAc)(CH_2)_2CONH_2$ | H | H |
| I-142 | $CH_2NHCOCH_2NHAc$ | H | H |
| I-143 | $CH_2NHCOCH(Me)NHAc$ | H | H |
| I-144 | $CH_2(NHCOCH_2)_2NHAc$ | H | H |

TABLE 13

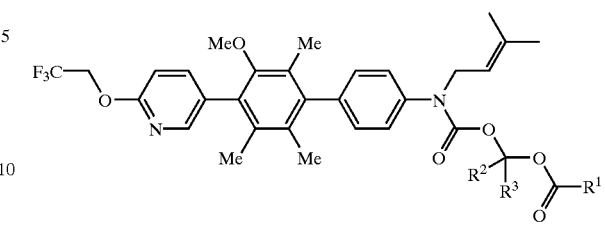

| No | R¹ | R² | R³ |
|---|---|---|---|
| I-145 | $CH_2CH_2CONH_2$ | H | H |
| I-146 | $CH_2CH_2CONHMe$ | H | H |
| I-147 | $CH_2OCONH_2$ | H | H |
| I-148 | $CH_2OCONHEt$ | H | H |
| I-149 | $CH_2NHAc$ | H | H |
| I-150 | $CH_2CH_2CH(CONH_2)NHAc$ | H | H |
| I-151 | $CH_2CH(Me)CONH_2$ | H | H |
| I-152 | $CH_2CH_2CONHMe$ | Me | H |
| I-153 | $CH(Me)OCONH_2$ | H | H |
| I-154 | $CH_2OCONHEt$ | Me | Me |
| I-155 | $CH_2NHAc$ | Et | H |
| I-156 | $CH(Me)CH_2CH(CONH_2)NHAc$ | Me | H |
| I-157 | $CH(NHAc)CH_2CONH_2$ | H | H |
| I-158 | $CH_2CH(NHAc)CONH_2$ | H | H |
| I-159 | $CH(NHAc)(CH_2)_2CONH_2$ | H | H |
| I-160 | $CH_2NHCOCH_2NHAc$ | H | H |
| I-161 | $CH_2NHCOCH(Me)NHAc$ | H | H |
| I-162 | $CH_2(NHCOCH_2)_2NHAc$ | H | H |

TABLE 14

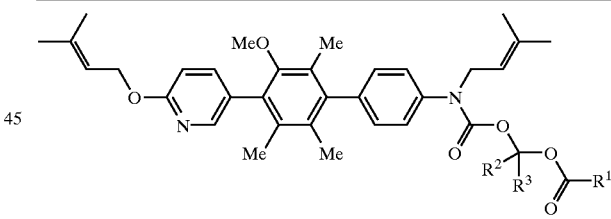

| No | R¹ | R² | R³ |
|---|---|---|---|
| I-163 | $CH_2CH_2CONH_2$ | H | H |
| I-164 | $CH_2CH_2CONHMe$ | H | H |
| I-165 | $CH_2OCONH_2$ | H | H |
| I-166 | $CH_2OCONHEt$ | H | H |
| I-167 | $CH_2NHAc$ | H | H |
| I-168 | $CH_2CH_2CH(CONH_2)NHAc$ | H | H |
| I-169 | $CH_2CH(Me)CONH_2$ | H | H |
| I-170 | $CH_2CH_2CONHMe$ | Me | H |
| I-171 | $CH(Me)OCONH_2$ | H | H |
| I-172 | $CH_2OCONHEt$ | Me | Me |
| I-173 | $CH_2NHAc$ | Et | H |
| I-174 | $CH(Me)CH_2CH(CONH_2)NHAc$ | Me | H |
| I-175 | $CH(NHAc)CH_2CONH_2$ | H | H |
| I-176 | $CH_2CH(NHAc)CONH_2$ | H | H |
| I-177 | $CH(NHAc)(CH_2)_2CONH_2$ | H | H |
| I-178 | $CH_2NHCOCH_2NHAc$ | H | H |
| I-179 | $CH_2NHCOCH(Me)NHAc$ | H | H |
| I-180 | $CH_2(NHCOCH_2)_2NHAc$ | H | H |

TABLE 15

| No | R¹ | R⁴ | R⁵ | R⁸ | R⁹ | R¹⁰ | R¹¹ | Y |
|---|---|---|---|---|---|---|---|---|
| I-181 | CH₂CH₂CONH₂ | H | F | H | Me | Me | H | iPr |
| I-182 | CH₂CH₂CONH₂ | F | H | Me | COOMe | Me | Me | CH₂CH=CMe₂ |
| I-183 | CH₂CH₂CONH₂ | H | H | H | Et | Et | H | CH₂CH=CMe₂ |
| I-184 | CH₂CH₂CONH₂ | H | Cl | H | OEt | OEt | H | CH₂CH=CMe₂ |
| I-185 | CH₂CH₂CONH₂ | Cl | H | H | COOMe | Me | H | iPr |
| I-186 | CH₂CH₂CONH₂ | H | H | Et | OMe | OMe | Et | CH₂CH=CMe₂ |
| I-187 | CH₂CH₂CONH₂ | H | F | Et | Et | Et | H | CH₂CH=CMe₂ |
| I-188 | CH₂CH₂CONH₂ | F | H | Me | Me | OMe | Me | CH₂CH=CMe₂ |
| I-189 | CH₂CH₂CONH₂ | H | H | Me | Me | COOMe | Me | CH₂CH=CMe₂ |
| I-190 | CH₂CH₂CONH₂ | H | Cl | H | OMe | OMe | OH | CH₂CH=CMe₂ |
| I-191 | CH₂CH₂CONH₂ | Cl | H | Me | Me | Me | OH | CH₂CH=CMe₂ |
| I-192 | CH₂CH₂CONH₂ | H | H | Me | Me | OH | Me | CH₂CH=CMe₂ |
| I-193 | CH₂CH₂CONHMe | H | F | H | OMe | OMe | H | iPr |
| I-194 | CH₂CH₂CONHMe | F | H | Me | COOMe | Me | Me | CH₂CH=CMe₂ |
| I-195 | CH₂CH₂CONHMe | H | H | H | Et | Et | H | CH₂CH=CMe₂ |
| I-196 | CH₂CH₂CONHMe | H | Cl | H | OEt | OEt | H | CH₂CH=CMe₂ |
| I-197 | CH₂CH₂CONHMe | Cl | H | H | COOMe | Me | H | CH₂CH=CMe₂ |
| I-198 | CH₂CH₂CONHMe | H | H | Et | OMe | OMe | Et | CH₂CH=CMe₂ |
| I-199 | CH₂CH₂CONHMe | H | F | Et | Et | Et | H | CH₂CH=CMe₂ |
| I-200 | CH₂CH₂CONHMe | F | H | Me | Me | OMe | Me | CH₂CH=CMe₂ |
| I-201 | CH₂CH₂CONHMe | H | H | Me | Me | COOMe | Me | iPr |
| I-202 | CH₂CH₂CONHMe | H | Cl | H | OMe | OMe | OH | CH₂CH=CMe₂ |
| I-203 | CH₂CH₂CONHMe | Cl | H | Me | Me | Me | OH | CH₂CH=CMe₂ |
| I-204 | CH₂CH₂CONHMe | H | H | Me | Me | OH | Me | CH₂CH=CMe₂ |

TABLE 16

| No | R¹ | R⁴ | R⁵ | R⁸ | R⁹ | R¹⁰ | R¹¹ |
|---|---|---|---|---|---|---|---|
| I-205 | CH₂OCONH₂ | H | F | H | OMe | OMe | H |
| I-206 | CH₂OCONH₂ | F | H | Me | COOMe | Me | Me |
| I-207 | CH₂OCONH₂ | H | H | H | Et | Et | H |
| I-208 | CH₂OCONH₂ | H | Cl | H | OEt | OEt | H |
| I-209 | CH₂OCONH₂ | Cl | H | H | COOMe | Me | H |
| I-210 | CH₂OCONH₂ | H | H | Et | OMe | OMe | Et |
| I-211 | CH₂OCONH₂ | H | F | Et | Et | Et | H |
| I-212 | CH₂OCONH₂ | F | H | Me | Me | OMe | Me |
| I-213 | CH₂OCONH₂ | H | H | Me | Me | COOMe | Me |
| I-214 | CH₂OCONH₂ | H | Cl | H | OMe | OMe | OH |
| I-215 | CH₂OCONH₂ | Cl | H | Me | Me | Me | OH |
| I-216 | CH₂OCONH₂ | H | H | Me | Me | OH | Me |
| I-217 | CH₂NHAc | H | F | H | OMe | OMe | H |
| I-218 | CH₂NHAc | F | H | Me | COOMe | Me | Me |
| I-219 | CH₂NHAc | H | H | H | Et | Et | H |
| I-220 | CH₂NHAc | H | Cl | H | OEt | OEt | H |
| I-221 | CH₂NHAc | Cl | H | H | COOMe | Me | H |

TABLE 16-continued

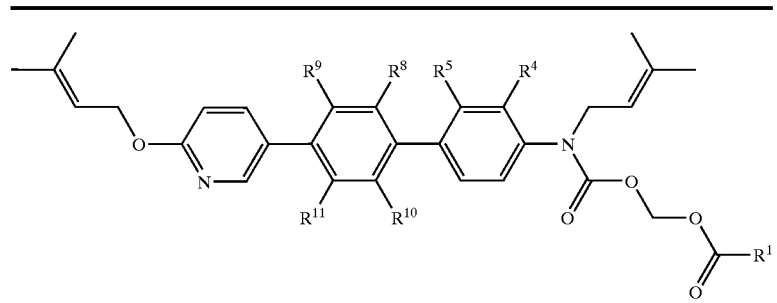

| No | R¹ | R⁴ | R⁵ | R⁸ | R⁹ | R¹⁰ | R¹¹ |
|---|---|---|---|---|---|---|---|
| I-222 | CH₂NHAc | H | H | Et | OMe | OMe | Et |
| I-223 | CH₂NHAc | H | F | Et | Et | Et | H |
| I-224 | CH₂NHAc | F | H | Me | Me | OMe | Me |
| I-225 | CH₂NHAc | H | H | Me | Me | COOMe | Me |
| I-226 | CH₂NHAc | H | Cl | H | OMe | OMe | OH |
| I-227 | CH₂NHAc | Cl | H | Me | Me | Me | OH |
| I-228 | CH₂NHAc | H | H | Me | Me | OH | Me |

TABLE 17

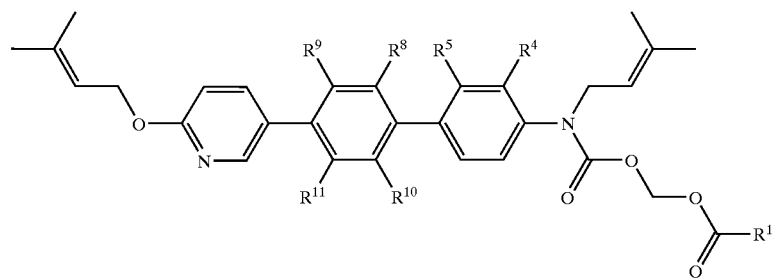

| No | R¹ | R⁴ | R⁵ | R⁸ | R⁹ | R¹⁰ | R¹¹ |
|---|---|---|---|---|---|---|---|
| I-229 | CH₂NHCOC₂H₅ | H | F | H | OMe | OMe | H |
| I-230 | CH₂CSNH₂ | F | H | Me | COOMe | Me | Me |
| I-231 | CH₂OCH₂CH₂OH | H | H | H | Et | Et | H |
| I-232 | CH₂OMe | H | F | H | OEt | OEt | H |
| I-233 | CH₂OCH₂CH₂OMe | F | H | H | COOMe | Me | H |
| I-234 | CH₂COCH₃ | H | H | Et | OMe | OMe | Et |
| I-235 | CH₂COC₂H₅ | H | F | Et | Et | Et | H |
| I-236 | CH₂OCOCH₃ | F | H | Me | Me | OMe | Me |
| I-237 | CH₂OCOC₂H₅ | H | H | Me | Me | COOMe | Me |
| I-238 | CH₂NHOH | H | F | H | OMe | OMe | OH |
| I-239 | CH₂NHCONH₂ | F | H | Me | Me | Me | OH |
| I-240 | CH₂NHCSNH₂ | H | H | Me | Me | OH | Me |
| I-241 | CH₂NHSO₂Me | H | F | H | OMe | OMe | H |
| I-242 | CH₂N(SO₂Me)₂ | F | H | Me | COOMe | Me | Me |
| I-243 | CH₂SO₂NH₂ | H | H | H | Et | Et | H |
| I-244 | CH₂SOMe | H | F | H | OEt | OEt | H |
| I-245 | CH₂SO₂Me | F | H | H | COOMe | Me | H |
| I-246 | CH₂OCH₂CONH₂ | H | H | Et | OMe | OMe | Et |
| I-247 | CH₂OCH₂CONMe₂ | H | F | Et | Et | Et | H |
| I-248 | CH₂SO₂NMe₂ | F | H | Me | Me | OMe | Me |
| I-249 | CH₂PO(OMe)₂ | H | H | Me | Me | COOMe | Me |
| I-250 | CH₂NHCSNHEt | H | F | H | OMe | OMe | OH |
| I-251 | CH₂CH=NNHCONH₂ | F | H | Me | Me | Me | OH |
| I-252 | CH₂CH=NNHCSNH₂ | H | H | Me | Me | OH | Me |
| I-253 | CH₂CH=NNHSO₂Me | H | F | H | OMe | OMe | H |
| I-254 | CH₂-1,2,3-Triazol-5-yl | F | H | Me | COOMe | Me | Me |
| I-255 | CH₂-Tetrazol-1-yl | H | H | H | Et | Et | H |

TABLE 18

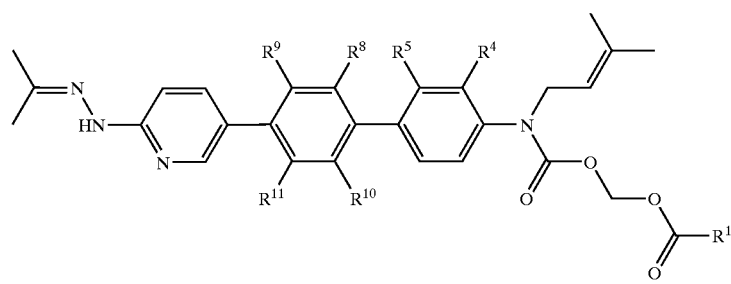

| No | R¹ | R⁴ | R⁵ | R⁸ | R⁹ | R¹⁰ | R¹¹ |
|---|---|---|---|---|---|---|---|
| I-256 | $CH_2NHCOC_2H_5$ | H | F | H | Me | Me | H |
| I-257 | $CH_2CSNH_2$ | F | H | Me | COOMe | Me | Me |
| I-258 | $CH_2OCH_2CH_2OH$ | H | H | H | Et | Et | H |
| I-259 | $CH_2OMe$ | H | F | H | OEt | OEt | H |
| I-260 | $CH_2OCH_2CH_2OMe$ | F | H | H | COOMe | Me | H |
| I-261 | $CH_2COCH_3$ | H | H | Et | OMe | OMe | Et |
| I-262 | $CH_2COC_2H_5$ | H | F | Et | Et | Et | H |
| I-263 | $CH_2OCOCH_3$ | F | H | Me | Me | OMe | Me |
| I-264 | $CH_2OCOC_2H_5$ | H | H | Me | Me | COOMe | Me |
| I-265 | $CH_2NHOH$ | H | F | H | OMe | OMe | OH |
| I-266 | $CH_2NHCONH_2$ | F | H | Me | Me | Me | OH |
| I-267 | $CH_2NHCSNH_2$ | H | H | Me | Me | OH | Me |
| I-268 | $CH_2NHSO_2Me$ | H | F | H | OMe | OMe | H |
| I-269 | $CH_2N(SO_2Me)_2$ | F | H | Me | COOMe | Me | Me |
| I-270 | $CH_2SO_2NH_2$ | H | H | H | Et | Et | H |
| I-271 | $CH_2SOMe$ | H | F | H | OEt | OEt | H |
| I-272 | $CH_2SO_2Me$ | F | H | H | COOMe | Me | H |
| I-273 | $CH_2OCH_2CONH_2$ | H | H | Et | OMe | OMe | Et |
| I-274 | $CH_2OCH_2CONMe_2$ | H | F | Et | Et | Et | H |
| I-275 | $CH_2SO_2NMe_2$ | F | H | Me | Me | OMe | Me |
| I-276 | $CH_2PO(OMe)_2$ | H | H | Me | Me | COOMe | Me |
| I-277 | $CH_2NHCSNHEt$ | H | F | H | OMe | OMe | OH |
| I-278 | $CH_2CH=NNHCONH_2$ | F | H | Me | Me | Me | OH |
| I-279 | $CH_2CH=NNHCSNH_2$ | H | H | Me | Me | OH | Me |
| I-280 | $CH_2CH=NNHSO_2Me$ | H | F | H | OMe | OMe | H |
| I-281 | $CH_2CH_2$-1,2,3-Triazol-5-yl | F | H | Me | COOMe | Me | Me |
| I-282 | $CH_2CH_2$-Tetrazoly-1-yl | H | H | H | Et | Et | H |

Test Example 1 IgE Antibody Production Inhibiting Effects Against Anti-ovalbumin (OVA)

1) Animal

BALB/c mice (female, 8–10 weeks old) and Wistar rats (female, 8–10 weeks old) purchased from Japan SLC (Shizuoka) were used.

2) Method of Immunization 0.2 mL of a solution obtained by suspending 2 μg of ovalbumin (OVA) and 2 mg of aluminium hydroxide gel in a physiological saline was injected in a BALB/c mouse intraperitoneally to immunize it. After ten days, blood was taken from the heart, serum was separated, and stored at −40° C. until the IgE antibody titer was measured.

3) Compound

The present compound and its parent compound (II-1) were dissolved or suspended in methylcellulose, and diluted 20-fold with a neutral oil Migriol 812 to obtain a solution, which was orally administered at an amount of 0.1 mL per mouse (dose 10, 40 mg/kg). Administration was carried out for consecutive 10 days from an immunization day to the day before a blood collection day.

4) Measurement of Anti-OVA IgE Antibody Titer (PCA Titer)

The resulting mouse serum was prepared into a 2-fold dilution series using a physiological saline, each 50 μl of which was injected to a pre-haircut Wistar rat intracutaneously at a back. After 24 hours, 0.5 mL of a physiological saline containing 1 mg of OVA and 5 mg of Evans Blue pigment was injected intravenously to induce passive cutaneous anaphylaxis reaction (PCA). After 30 minutes, a maximum dilution rate of the serum showing PCA positive reaction of a pigment spot having a diameter of 5 mm or more was determined, and $Log_2$ of its dilution rate was adopted as a PCA titer. For example, when a serum becomes PCA reaction positive until $2^7$-fold dilution, an anti-OVA IgE antibody titer of the mouse is 7. The results are shown in Table 19.

TABLE 19

|  | 3 mg/Kg | 10 mg/Kg | 40 mg/Kg |
|---|---|---|---|
| II-1 | — | 6.7 | 0.8 |
| I-1 | 7.0 | 0.8 | — |
| I-6 | — | 1.8 | — |
| I-13 | — | <0 | — |
| I-15 | — | 0 | — |
| I-16 | — | <0 | — |

The present compound exhibits the higher activity as compared with a compound (II-1), and it can be seen that the present compound effectively acts as a prodrug.

Test Example 2 Oral Absorption Test

The present compound (I-1) was ground with an agate mortar, which was prepared into an aqueous suspension having the concentration of 10 mg/mL using a 0.5% aqueous methylcellulose solution as a vehicle. Each compound was orally administered to a Jcl:SD male rat (10 weeks old, 18 hours fasting) as a parent compound at a rate of 20 mg/kg. 0.5, 1, 2, 4, 6, 8 and 24 hours after administration, 0.3 mL of blood was taken from a cannula inserted in rat jugular in advance. The blood was centrifuged to obtain a plasma. 0.5 mL of a mixed solution of methanol and acetonitrile (1/1 (w/w)) was added to 0.1 mL of the plasma, proteins were removed therefrom, followed by centrifugation. The supernatant was used as a HPLC sample. The HPLC conditions for the compound are shown in Table 20.

TABLE 20

| Column | Develosil ODS-UG-5 |
| --- | --- |
|  | (4.6 × 150 mm) |
| Mobile phase | 0.1 M NaClO$_4$:MeOH = 12:88 |
| Rate (mL/min) | 1.0 mL/min |
| Detection | UV:255 nm |
| Retention time (min) | 15.5 min |

The $C_{max}$ was 2.50 μg/mL, and the AUC was 32.03 μg·hr/mL. The time course of the plasma concentration after oral administration is shown in FIG. 1.

The present compound (I-1) was not detected in the circulating plasma of (I-1)-orally administered rat, and only a parent compound (II-1) was observed, exhibiting the high concentration in the plasma. The compound (I-1) has the high oral absorbability, and it can be seen that it is useful as a prodrug. Further, as described above, a melting point thereof was elevated and improvement in the physical properties was attained.

Test Example 3 Oral Absorption Test

The oral absorbabilities of the present compound (I-163) and its parent compound (II-4) were measured as in Test Example 2. The HPLC conditions are shown in Table 21.

TABLE 21

|  | I-163 | II-4 |
| --- | --- | --- |
| Column | Develosil ODS-UG-5 | Develosil ODS-UG-5 |
|  | (2.0 × 150 mm) | (2.0 × 150 mm) |
| Mobile phase | H$_2$O:MeOH = 12:88 | H$_2$O:MeOH = 12:88 |
| Rate (mL/min) | 0.2 mL/min | 1.0 mL/min |
| Detection | UV:255 nm | UV:255 nm |
| Retention time (min) | 14.5 min | 6.6 min |

Figure 2:
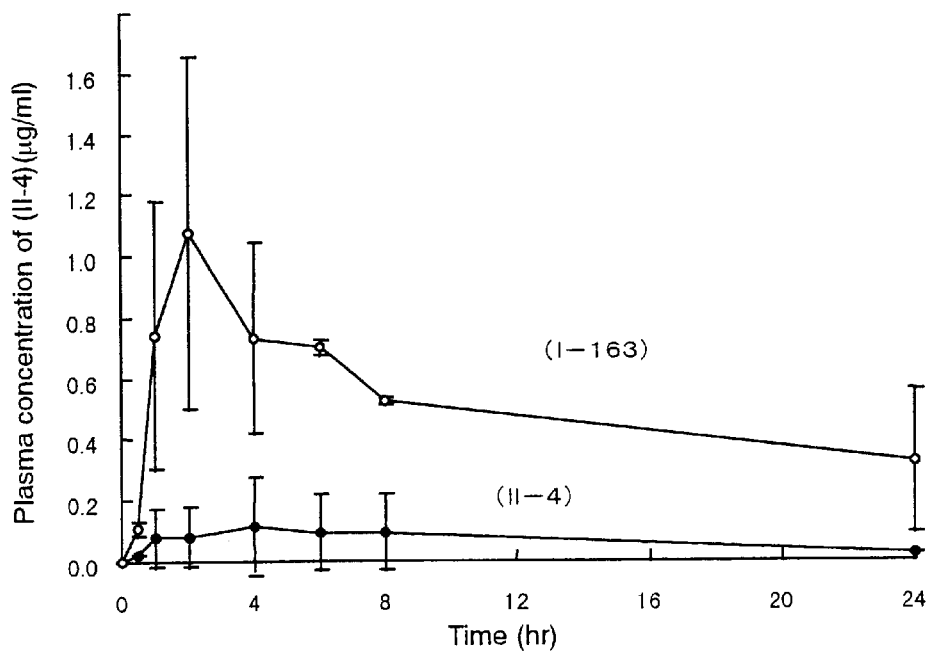
FIG. 2 is a view showing the concentration of a parent compound (II-4) in plasma when a compound (I-163) or a parent compound (II-4) is administered.

The $C_{max}$ of the parent compound (II-4) was 0.11 μg/mL, and the AUC was 1.64 μg·hr/mL. The $C_{max}$ of the present compound (I-163) was 1.08 μg/mL, and the AUC was 12.38 μg·hr/mL. The time course of the plasma concentration after oral administration is shown in FIG. 2. The present compound showed the extremely high oral absorbability as compared with the parent compound.

Test Example 4 Oral Absorption Test

The oral absorbabilities of the present compound (I-16) and its parent compound (II-1) were measured as in Test Example 2 using a non-fasting rat. The HPLC conditions are shown in Table 22.

TABLE 22

|  | I-16 | II-1 |
| --- | --- | --- |
| Column | Develosil ODS-UG-5 | Develosil ODS-UG-5 |
|  | (2.0 × 150 mm) | (2.0 × 150 mm) |
| Mobile phase | H$_2$O/MeOH = 12/88 | H$_2$O/MeOH = 12/88 |
| Rate (mL/min) | 0.2 mL/min | 0.2 mL/min |
| Detection | UV:255 nm | UV:255 nm |
| Retention time (min) | 6.7 min | 16.0 min |

Figure 3:
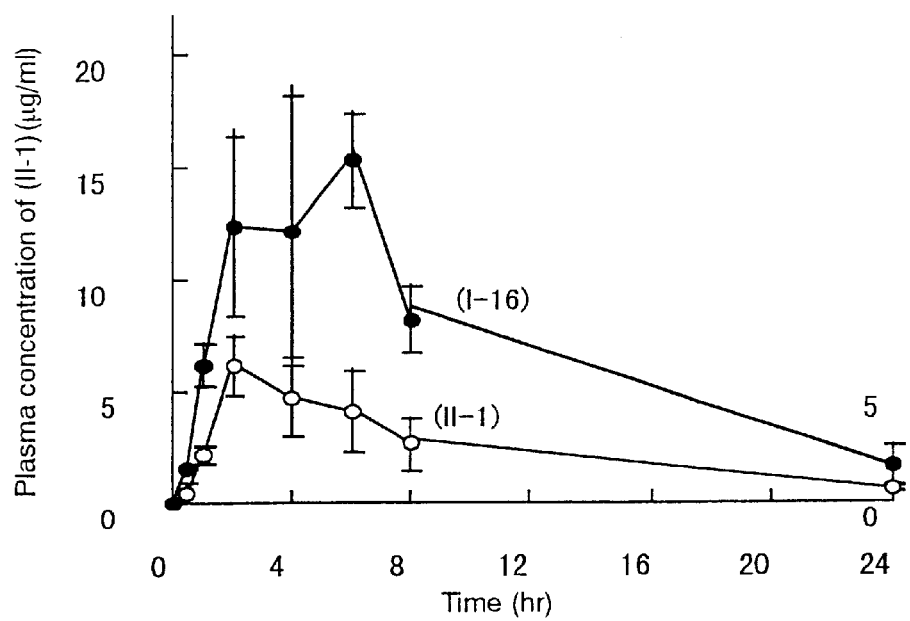
FIG. 3 is a view showing the concentration of a parent compound (II-1) in plasma when a compound (I-16) or a parent compound (II-1) is administered.

The compound (I-16) was not detected in the circulating plasma of the present compound (I-16)-orally administered rat, only the parent compound (II-1) was observed, exhibiting the high concentration in the plasma. The $C_{max}$ of the (II-1) was 6.13 μg/mL, and the AUC was 57.31 μg·hr/mL. The $C_{max}$ of the (I-16) was 16.02 μg/mL, and the AUC was 165.52 μg·hr/mL. The time course of the plasma concentration after oral administration is shown in FIG. 3.

| Preparation Example 1 Tablets | |
| --- | --- |
| Compound (I) | 15 mg |
| Starch | 15 mg |
| Lactose | 15 mg |
| Crystalline cellulose | 19 mg |
| Polyvinyl alcohol | 3 mg |
| distilled water | 30 ml |
| Calcium stearate | 3 mg |

Ingredients other than calcium stearate were mixed uniformly, ground and granulated, dried, and prepared into granules having a suitable size. Then, calcium stearate was added, which was compression-molded to obtain tablets.

Industrial Applicability

The compound (I) shows the high oral absorbability and its active form of a compound (II) show the strong immunosuppressive activity and/or antiallergic activity. Accordingly, the present compound is very useful as an immunosuppressive agent and/or an antiallergic agent.

What is claimed is:

1. A compound represented by the formula (I):

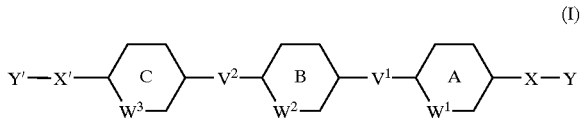

wherein is —N(COOCR$^3$R$^2$OCOR$^1$)—, and X' is —O—,
R$^1$ is lower alkyl sustituted with 1 or 2 groups selected from the group consisting of —CONH$_2$, —CONHCH$_3$, —CONHC$_2$H$_5$, —OCONH$_2$, —OCONHCH$_3$, —OCONHC$_2$H$_5$, —(NHCOCRR')mNHCOCH$_3$, —(NHCOCRR')mNHCOC$_2$H$_5$, —CSNH$_2$, —(OCH$_2$CH$_2$)nOH, —OCH$_3$, —(OCH$_2$CH$_2$)nOCH$_3$, —COCH$_3$, —COC$_2$H$_5$, —OCOCH$_3$, —OCOC$_2$H$_5$, —NHOH, —NHCONH$_2$, —NHCSNH$_2$, —NHSO$_2$CH$_3$, —N(CO$_2$CH$_3$)$_2$, —SO$_2$NH$_2$, —SOCH$_3$, —SO$_2$CH$_3$, —OCH$_2$CONH$_2$, —OCH$_2$CON(CH$_3$)$_2$, —SO$_2$N(CH$_3$)$_2$, —PO(OCH$_3$)$_2$, —NHCSNHC$_2$H$_5$, —CH=NNHCONH$_2$, —CH=NNHCSNH$_2$, or —CH=NNHSO$_2$CH$_3$, triazolyl and tetrazolyl (wherein R and R' are each independently hydrogen or lower alkyl, m is an integer of 0 to 2, and n is an integer of 1 or 2), $R^2$ and $R^3$ are each independently hydrogen or lower alkyl, Y and Y' are each independently hydrogen, optionally substituted lower alkyl, optionally substituted lower alkenyl, optionally substituted lower alkynyl, optionally substituted cycloalkyl, optionally substituted cycloalkenyl, optionally substituted lower alkoxycarbonyl, optionally substituted, sulfamoyl, optionally substituted amino, optionally substituted aryl or optionally substituted 5-membered or 6-membered heterocycle, ring A, and ring B are each an optionally substituted benzene ring, and ring C is pyridine, both $V^1$ and $V^2$ are a single bond, or a pharmaceutically acceptable salt or a solvate thereof.

2. A compound represented by the formula (II):

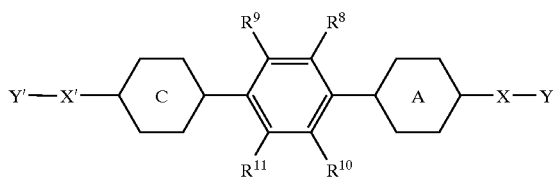

(II)

wherein X is —N(COOCR$^3$R$^2$OCOR$^1$)—, and X' is —O—,

Y and Y' are each independently optionally substituted lower alkyl, optionally substituted lower alkenyl or optionally substituted lower alkynyl, $R^1$, $R^2$ and $R^3$ have the same meanings as those for claim 1, ring A is optionally substituted benzene ring and ring C is pyridine, $R^8$, $R^9$, $R^{10}$ and $R^{11}$, are each independently hydrogen, halogen, hydroxy, optionally substituted lower alkyl, optionally substituted lower alkoxy, optionally substituted lower alkenyl, optionally substituted lower alkenyloxy, optionally substituted cycloalkyloxy, optionally substituted acyloxy, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsultonyl or optionally substituted arylsulfonyloxy, or a pharmaceutically acceptable salt or a solvate thereof.

3. A compound represented by the formula (III):

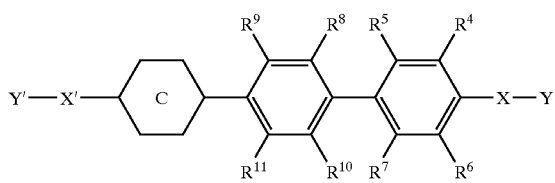

(III)

wherein X is —N(COOCR$^3$R$^2$OCOR$^1$)—, X' is —O—,

Y and Y' are each independently optionally substituted lower alkyl or optionally substituted lower alkenyl, $R^1$, $R^2$ and $R^3$ have the same meanings as those for claim 1, $R^4$, $R^5$, $R^6$, $R^7$, $R^8$, $R^9$, $R^{10}$ and $R^{11}$ are each independently hydrogen, halogen, hydroxy, optionally substituted lower alkyl, optionally substituted lower alkoxy, optionally substituted lower alkenyl, optionally substituted lower alkenyloxy, carboxy, optionally substituted lower alkoxycarbonyl or optionally substituted amino, ring C is pyridine, optionally substituted with lower alkyl, or a pharmaceutically acceptable salt or a solvate thereof.

4. The compound according to any one of claims 1 to 3, wherein $R^1$ is C1 to C3 alkyl substituted with 1 or 2 groups selected from the group consisting of —CONH$_2$, —OCONH$_2$ and —(NHCOCRR')mNHCOCH$_3$, a pharmaceutically salt or a solvate thereof.

5. The compound according to claim 3, wherein $R^4$ and $R^5$ are each independently hydrogen or halogen, or a pharmaceutically acceptable salt or a solvate thereof.

6. The compound according to claim 3, wherein $R^6$ and $R^7$ are both hydrogen, or a pharmaceutically acceptable salt or a solvate thereof.

7. The compound according to claim 2 or 3, wherein $R^8$ and $R^{11}$ are each independently hydrogen, hydroxy or lower alkyl, a pharmaceutically acceptable salt or a solvate thereof.

8. The compound according to claim 2 or 3, wherein $R^9$ and $R^{10}$ are each independently lower alkyl, lower alkoxy or lower alkoxycarbonyl, or a pharmaceutically acceptable salt or a solvate thereof.

9. The compound according to claim 3, wherein X is —N(COOCHR$^2$OCOR$^1$)—, X' is —O—, $R^1$ is C1 to C3 alkyl substituted with 1 or 2 groups selected from the group consisting of —CONH$_2$, —OCONH$_2$ and —(NHCOCRR')mNHCOCH$_3$, $R^2$ and $R^3$ are hydrogen or C1 to C3 alkyl, Y and Y' are each independently lower alkyl optionally substituted with halogen or lower alkenyl optionally substituted with halogen, $R^4$ and $R^5$ are each independently hydrogen or halogen, $R^6$ and $R^7$ are both hydrogen, $R^8$ and $R^{11}$ are each independently hydrogen, hydroxy or lower alkyl, $R^9$ and $R^{10}$ are each independently lower alkyl, lower alkoxy or lower alkoxycarbonyl, and ring C is pyridine optionally substituted with lower alkyl, or a pharmaceutically acceptable salt or a solvate thereof.

10. The compound according to any one of claims 1, 2, 3 and 9, wherein Y and Y' are both prenyl, or a pharmaceutically acceptable salt or a solvate thereof.

11. The compound according to claim 3 or 4, wherein ring C is

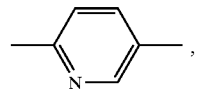

, $R^4$ and $R^5$ are each independently hydrogen, halogen or lower alkoxy, $R^6$ and $R^7$ are each independently hydrogen, halogen or lower alkyl, $R^8$ and $R^{11}$ are both lower alkyl, or one of them is lower alkyl and the other is hydrogen or lower alkoxy, $R^9$ and $R^{10}$ are both hydrogen, lower alkyl or lower alkoxy, and one of —X—Y and —X'—Y' is —N(COOCR$^3$R$^2$OCOR$^1$)-Alk(wherein Alk is optionally substituted lower alkyl or optionally substituted lower alkenyl), and the other is prenyloxy or prenylamino, or a pharmaceutically acceptable salt or a solvate thereof.

12. The compound according to claim 3 or 4, wherein ring C is
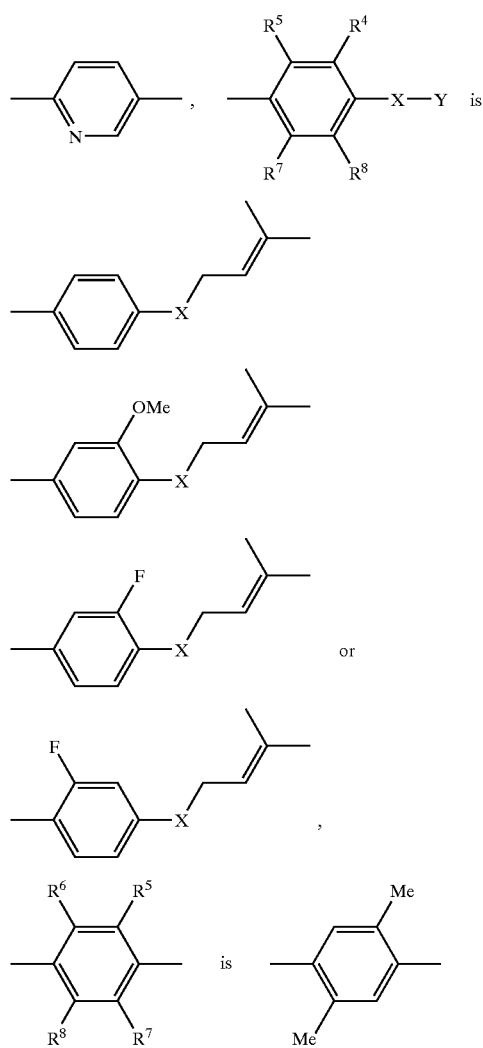
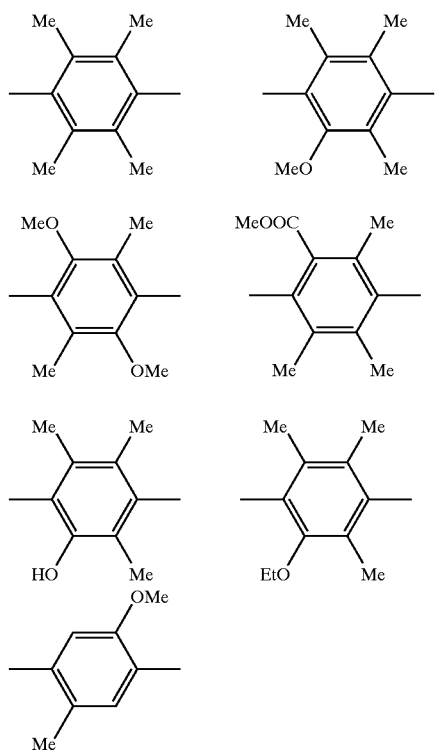
wherein X has the same meaning as that for claim 3, or a salt or a solvate thereof.
13. A pharmaceutical composition, which comprises a compound as defined in any one of claims 1 to 3, or a pharmaceutically acceptable salt or a solvate thereof.
* * * * *